US011692202B2

(12) United States Patent
Ikeda et al.

(10) Patent No.: US 11,692,202 B2
(45) Date of Patent: Jul. 4, 2023

(54) SCARLESS GENOME EDITING THROUGH TWO-STEP HOMOLOGY DIRECTED REPAIR

(71) Applicant: The Board of Trustees of the Leland Stanford Junior University, Stanford, CA (US)

(72) Inventors: Kazuya Ikeda, Koto (JP); Matthew H. Porteus, Stanford, CA (US)

(73) Assignee: THE BOARD OF TRUSTEES OF THE LELAND STANFORD JUNIOR UNIVERSITY, Stanford, CA (US)

(*) Notice: Subject to any disclaimer, the term of this patent is extended or adjusted under 35 U.S.C. 154(b) by 673 days.

(21) Appl. No.: 16/740,234

(22) Filed: Jan. 10, 2020

(65) Prior Publication Data
US 2020/0208172 A1    Jul. 2, 2020

Related U.S. Application Data

(63) Continuation of application No. PCT/US2018/042702, filed on Jul. 18, 2018.

(60) Provisional application No. 62/533,780, filed on Jul. 18, 2017.

(51) Int. Cl.
| | | |
|---|---|---|
| C07H 21/02 | (2006.01) |
| C07H 21/04 | (2006.01) |
| C12N 15/85 | (2006.01) |
| C12N 9/22 | (2006.01) |
| C12N 15/90 | (2006.01) |
| G01N 21/64 | (2006.01) |
| A61K 48/00 | (2006.01) |
| C12N 5/0735 | (2010.01) |
| C12N 5/074 | (2010.01) |

(52) U.S. Cl.
CPC ............... *C12N 15/85* (2013.01); *C12N 9/22* (2013.01); *C12N 15/902* (2013.01); *C12N 15/907* (2013.01); *G01N 21/6486* (2013.01); *A61K 48/00* (2013.01); *C12N 5/0606* (2013.01); *C12N 5/0607* (2013.01); *C12N 2310/122* (2013.01); *C12N 2310/531* (2013.01); *C12N 2510/04* (2013.01)

(58) Field of Classification Search
CPC . C12N 9/22; C12N 2310/20; C12N 2310/531
See application file for complete search history.

(56) References Cited

U.S. PATENT DOCUMENTS

2016/0024529 A1* 1/2016 Carstens .............. C12N 15/902
                                                            435/252.33
2017/0067078 A1    3/2017 Frendewey et al.

FOREIGN PATENT DOCUMENTS

CN         108085328 A     5/2018

OTHER PUBLICATIONS

Dever et al. (Nature, 539, 2016, 384-389).*
Chu et al. (Nature Biotechnology, 33, 5, 2015, 543-548).*
Chu et al., "Increasing the Efficiency of Homology-Directed Repair for CRISPR-Cas9-lnduced Precise Gene Editing in Mammalian Cells," Nature Biotechnology, vol. 33, No. 5, Mar. 24, 2015, pp. 543-548.
Dever et al., "CRISPR/Cas9 β-Globin Gene Targeting in Human Haematopoietic Stem Cells," Nature, vol. 539, No. 7629, Nov. 17, 2016, pp. 384-389.
PCT/US2018/042702, "International Preliminary Report on Patentability," dated Jan. 30, 2020, 10 pages.
PCT/US2018/042702, "International Search Report and Written Opinion," dated Nov. 26, 2018, 15 pages.
Xi et al., "A novel two-step genome editing strategy with CRISPR-Cas9 provides new insights into telomerase action and TERT gene expression," Genome Biology, 16:231 (2015), 43 pages.
Lamb et al., "Tools and strategies for scarless allele replacement in Drosophila using CRISPR/Cas9," Fly, 11:1,53-64 (2017), 23 pages.

* cited by examiner

*Primary Examiner* — Amy H Bowman
(74) *Attorney, Agent, or Firm* — Kilpatrick Townsend & Stockton LLP

(57) ABSTRACT

A method for scarless genome editing is disclosed. In particular, the method provides scarless genome modification by using homology directed repair (HDR) steps to genetically modify cells and remove unwanted sequences. This method can be used for genome editing, including introducing mutations, deletions, or insertions at any position in the genome without leaving silent mutations, selection marker sequences, or other additional undesired sequences in the genome.

22 Claims, 53 Drawing Sheets
Specification includes a Sequence Listing.

| Clone # | Donor | Total | WT | c. 928G>A Homo | Hetero |
|---|---|---|---|---|---|
| 2 | c. 928G>A | 7 | 0 | 7 | 0 |
| 2 | WT + c. 928G>A | 24 | 8 | 7 | 9 |
| 13 | c. 928G>A | 16 | 4 | 0 | 12 |

FIG. 2G

```
              11111111112
         12345678901234567890
         PAMXXXXXXXXXXXXXXXXXX GUIDE
LEFT ARM YYYYYYYCCNXXXXXXXXXXXXXXXX
         CNXXXXXXXXXXXXXXXXXXXYYYYY RIGHT ARM
         ━━━━━━━━━━━━━━━━━━━━━
         Microhomology (19 nt)
```

FIG. 5B

```
              11111111112
     12345678901234567890
     PAMXXXXXXXXXXXXXXXXXX GUIDE
LEFT ARM CCNXXXXXXXXXXXXXXXXXXXXYYYYYYYYYY
     CNXXXXXXXXXXXXXXXXXXXXXYYYYYYYYYYYY RIGHT ARM
         ════════════════════════════════
            Microhomology (32 nt)
```

FIG. 5C

GFI1 editing

Genome
AGGAAGGTGGACCTCCGAAGGCACCGGGAGACGCAGCAGCATGGGCTCAAATGAGCACCTGGCTGGCTGCAAGCAGCTACACAACACTAC
--------NGG  Guide 1                                                    GFI1 exon1
                                                  GFI1 editing region Same as 2nd gRNA for RUNX1 editing
                                  Guide 2

1st donor DNA
AGGAAGGTGGACCTCCGAAGGCACCGGGAGACGCAGCAGCATGGGCTCAAACCCTACCCTGCGATGAGCGGCAGTCCGCGCCGGGTTTTGGCGC
--------GGN                                                                    UbC promoter
         Left homology arm

FIG. 6C

| Clone # | Donor | Total | WT/insG | insG/insG | insG/c. 928 G>A |
|---|---|---|---|---|---|
| 14 | c. 928 G>A | 7 | 0 | 1 | 6 |
| 14 | WT | 13 | 10 | 3 | 0 |

FIG. 7B

SEQUENCE LISTING

<160> NUMBER OF SEQ ID NOS: 44

<210> SEQ ID NO 1
<211> LENGTH: 20
<212> TYPE: DNA
<213> ORGANISM: Artificial Sequence
<220> FEATURE:
<223> OTHER INFORMATION: primer 1
<220> FEATURE:

```
<221> NAME/KEY: source
<222> LOCATION: (1)..(20)
<223> OTHER INFORMATION: sequence is synthesized

<400> SEQUENCE: 1
cgtcagtttc tttggtcggt                                              20

<210> SEQ ID NO 2
<211> LENGTH: 18
<212> TYPE: DNA
<213> ORGANISM: Artificial Sequence
<220> FEATURE:
<223> OTHER INFORMATION: primer 2
<220> FEATURE:
<221> NAME/KEY: source
<222> LOCATION: (1)..(18)
<223> OTHER INFORMATION: sequence is synthesized

<400> SEQUENCE: 2
aaacacactc gccaaccc                                                18

<210> SEQ ID NO 3
<211> LENGTH: 26
<212> TYPE: DNA
<213> ORGANISM: Artificial Sequence
<220> FEATURE:
<223> OTHER INFORMATION: probe
<220> FEATURE:
<221> NAME/KEY: source
<222> LOCATION: (1)..(26)
<223> OTHER INFORMATION: sequence is synthesized

<400> SEQUENCE: 3
tcttcttaag tagctgaagc tccggt                                       26

<210> SEQ ID NO 4
<211> LENGTH: 21
<212> TYPE: DNA
<213> ORGANISM: Artificial Sequence
<220> FEATURE:
<223> OTHER INFORMATION: UbC promoter primer 1
<220> FEATURE:
<221> NAME/KEY: source
<222> LOCATION: (1)..(21)
<223> OTHER INFORMATION: sequence is synthesized

<400> SEQUENCE: 4
ctctcctctt tgatacggcc c                                            21

<210> SEQ ID NO 5
<211> LENGTH: 20
<212> TYPE: DNA
<213> ORGANISM: Artificial Sequence
<220> FEATURE:
<223> OTHER INFORMATION: UbC promoter primer 2
<220> FEATURE:
<221> NAME/KEY: source
<222> LOCATION: (1)..(20)
<223> OTHER INFORMATION: sequence is synthesized

<400> SEQUENCE: 5
agtgttgtcc cagacagtgc                                              20

<210> SEQ ID NO 6
<211> LENGTH: 26
<212> TYPE: DNA
<213> ORGANISM: Artificial Sequence
<220> FEATURE:
<223> OTHER INFORMATION: UbC promoter probe
```

```
<220> FEATURE:
<221> NAME/KEY: source
<222> LOCATION: (1)..(26)
<223> OTHER INFORMATION: sequence is synthesized

<400> SEQUENCE: 6
ctgccaagtt gtggcctctg tcaaag                                              26

<210> SEQ ID NO 7
<211> LENGTH: 7151
<212> TYPE: DNA
<213> ORGANISM: Artificial Sequence
<220> FEATURE:
<223> OTHER INFORMATION: Tbx1 1st donor vector

<400> SEQUENCE: 7
ccaatgctta atcagtgagg cacctatctc agcgatctgt ctatttcgtt catccatagt      60
tgcctgactc cccgtcgtgt agataactac gatacgggag ggcttaccat ctggccccag     120
tgctgcaatg ataccgcgag acccacgctc accggctcca gatttatcag caataaacca     180
gccagccgga agggccgagc gcagaagtgg tcctgcaact ttatccgcct ccatccagtc     240
tattaattgt tgccgggaag ctagagtaag tagttcgcca gttaatagtt tgcgcaacgt     300
tgttgccatt gctacaggca tcgtggtgtc acgctcgtcg tttggtatgg cttcattcag     360
ctccggttcc caacgatcaa ggcgagttac atgatccccc atgttgtgca aaaaagcggt     420
tagctccttc ggtcctccga tcgttgtcag aagtaagttg gccgcagtgt tatcactcat     480
ggttatggca gcactgcata attctcttac tgtcatgcca tccgtaagat gcttttctgt     540
gactggtgag tactcaacca agtcattctg agaatagtgt atgcggcgac cgagttgctc     600
ttgcccggcg tcaatacggg ataataccgc gccacatagc agaactttaa aagtgctcat     660
cattggaaaa cgttcttcgg ggcgaaaact ctcaaggatc ttaccgctgt tgagatccag     720
ttcgatgtaa cccactcgtg cacccaactg atcttcagca tcttttactt tcaccagcgt     780
ttctgggtga gcaaaaacag gaaggcaaaa tgccgcaaaa aagggaataa gggcgacacg     840
gaaatgttga atactcatac tcttcctttt tcaatattat tgaagcattt atcagggtta     900
ttgtctcatg agcggataca tatttgaatg tatttagaaa aataaacaaa tagggggttcc     960 gcgcacattt ccccgaaaag tgccacctga cgttaactcg agtcgacggc ccagtgaccc    1020
agcctcatct tggaattaag ggttttgccc aactcatcca ggaaactcat gccaactca    1080 gacctcagcc catttcctgg ctcccacccc agatcctcag cccagcccca ccgctggagc    1140
tgattcccca ccttgtcttc cagattattc tgaattccat gcacagatac cagccccgct    1200
tccacgtggt ctatgtggac ccacgcaaag atagcgagaa atatgccgag gagaacttca    1260
aaacctttgt gttcgaggag acacgattca ccgcggtcac tgcctaccag aaccatcggg    1320
tgagggcctg tggggaggac ctgagcggat tcaacgcctc tggaaaagcg ggtgtaattt    1380
tcagttgccg tttggggaca gtgggtccgc ttagacctgc aggctgtggt cccagtggag    1440
cccaacccaa ctggagcccc actcccaagg gcctcaggca gcccctcccc tctcgaggct    1500
ggccggccca gcctcctatc agcttgacct ctccagcggc aactgtcact tcgtcctgaa    1560 agtttgttt ccgaaccatt ccggaaactc cccatcaggg gcctgatctg aggtttaccc    1620
agattactag ggaacccgct ctgttcccca cccccacccc cactgcacgt ggggggtggt    1680
gaccacattc ctgtcccagc gaggagcaca gggcctccat ccccacccac ctgggggaca    1740
ccagagaggg gttccctagt gagagaggag gttcctcaga cccccgcccc cctgcaggag    1800
```

-continued

```
ggagcaccag ctccgtagag gaggggcaga cgtggactgg ttcttgtcag ggcagcagaa    1860
aggcccttgg tgcgcttctc ctaacactcc cctatcctcc gccgaggtcg ggtggcccag    1920
gctgcagggc tccagcggct tgctcacacc cacctccctg cagatcacgc agctcaagat    1980
tgccagcaat cccttcgcga aaggcttccg ggactgtgac cctgaggact ggtgagtgtc    2040
ctcccccgag agagtgagcg ccgggcgcct ggcgcaggcg ccgccctgat ccgcctcccg    2100
cccgcaggcc ccggaaccac cggcccagcg cactgccgct catcgaaggt ctagactccg    2160
cgccgggttt tggcgcctcc cgcgggcgcc cccctcctca cggcgagcgc tgccacgtca    2220
gacgaagggc gcagcgagcg tcctgatcct ccgcccgga cgctcaggac agcggcccgc    2280
tgctcataag actcggcctt agaacccag tatcagcaga aggacatttt aggacgggac    2340
ttgggtgact ctagggcact ggttttcttt ccagagagcg gaacaggcga ggaaaagtag    2400
tcccttctcg gcgattctgc ggagggatct ccgtggggcg gtgaacgccg atgattatat    2460
aaggacgcgc cgggtgtggc acagctagtt ccgtcgcagc cgggatttgg gtcgcggttc    2520
ttgtttgtgg atcgctgtga tcgtcacttg gtgagtagcg ggctgctggg ctggccgggg    2580
ctttcgtggc cgccgggccg ctcggtggga cggaagcgtg tggagagacc gccaagggct    2640
gtagtctggg tccgcgagca aggttgccct gaactggggg ttgggggag cgcagcaaaa    2700
tggcggctgt tcccgagtct tgaatggaag acgcttgtga ggcgggctgt gaggtcgttg    2760
aaacaaggtg gggggcatgg tgggcggcaa gaacccaagg tcttgaggcc ttcgctaatg    2820
cgggaaagct cttattcggg tgagatgggc tggggcacca tctgggacc ctgacgtgaa    2880
gtttgtcact gactggagaa ctcggtttgt cgtctgttgc gggggcggca gttatgcgg    2940
tgccgttggg cagtgcaccc gtaccttttgg gagcgcgcgc cctcgtcgtg tcgtgacgtc    3000
acccgttctg ttggcttata atgcaggggtg gggccacctg ccggtaggtg tgcggtaggc    3060
ttttctccgt cgcaggacgc agtgttcggg cctagggtag gctctcctga atcgacaggc    3120
gccggacctc tggtgagggg agggataagt gaggcgtcag tttctttggt cggttttatg    3180
tacctatctt cttaagtagc tgaagctccg gttttgaact atgcgctcgg ggttggcgag    3240
tgtgttttgt gaagttttttt aggcaccttt tgaaatgtaa tcatttgggt caatatgtaa    3300
ttttcagtgt tagactagta aattgtccgc taaattctgg ccgttttttgg ctttttttgtt    3360
agacggtacc gagctcttcg aaggatccat cgccaccatg gtgagcaagg gcgaggagga    3420
taacatggcc atcatcaagg agttcatgcg cttcaaggtg cacatggagg gctccgtgaa    3480
cggccacgag ttcgagatcg agggcgaggg cgagggccgc ccctacgagg cacccagac    3540
cgccaagctg aaggtgacca agggtggccc cctgcccttc gcctgggaca tcctgtcccc    3600
tcagttcatg tacggctcca aggcctacgt gaagcacccc gccgacatcc ccgactactt    3660
gaagctgtcc ttccccgagg gcttcaagtg ggagcgcgtg atgaacttcg aggacggcgg    3720
cgtggtgacc gtgacccagg actcctccct gcaggacggc gagttcatct acaaggtgaa    3780
gctgcgcggc accaacttcc cctccgacgg ccccgtaatg cagaagaaga ccatgggctg    3840
ggaggcctcc tccgagcgga tgtaccccga ggacggcgcc ctgaagggcg agatcaagca    3900
gaggctgaag ctgaaggacg gcggccacta cgacgctgag gtcaagacca cctacaaggc    3960
caagaagccc gtgcagctgc ccggcgccta aacgtcaac atcaagttgg acatcacctc    4020
ccacaacgag gactcacca tcgtggaaca gtacgaacgc gccgagggcc gccactccac    4080
cggcggcatg gacgagctgt acaaggaggg caggggcagc ctgctgacct gcggcgacgt    4140
ggaggagaac cccggccca tgccccccc caggctgctg ttcttcctgc tgttcctgac    4200
```

```
ccccatggag gtgaggcccg aggagcccct ggtggtgaag gtggaggagg gcgacaacgc    4260
cgtgctgcag tgcctgaagg gcaccagcga cggccccacc cagcagctga cctggagcag    4320
ggagagcccc ctgaagccct tcctgaagct gagcctgggc ctgcccggcc tgggcatcca    4380
catgaggccc ctggccatct ggctgttcat cttcaacgtg agccagcaga tgggcggctt    4440
ctacctgtgc cagcccggcc ccccagcga gaaggcctgg cagcccggct ggaccgtgaa    4500
cgtggagggc agcggcgagc tgttcaggtg aacgtgagc gacctgggcg gcctgggctg    4560
cggcctgaag aacaggagca gcgagggccc cagcagcccc agcggcaagc tgatgagccc    4620
caagctgtac gtgtgggcca aggacaggcc cgagatctgg gagggcgagc cccctgcct    4680 gcccccagg gacagcctga accagagcct gagccaggac ctgaccatgg cccccggcag    4740
caccctgtgg ctgagctgcg gcgtgccccc cgacagcgtg agcaggggcc cctgagctg    4800 gacccacgtg caccccaagg gccccaagag cctgctgagc ctggagctga aggacgacag    4860
gcccgccagg gacatgtggg tgatggagac cggcctgctg ctgcccaggg ccaccgccca    4920
ggacgccggc aagtactact gccacagggg caacctgacc atgagcttcc acctggagat    4980
caccgccagg cccgtgctgt ggcactggct gctgaggacc ggcggctgga aggtgagcgc    5040
cgtgaccctg gcctacctga tcttctgcct gtgcagcctg gtgggcatcc tgcacctgca    5100
gagggccctg gtgctgagga ggaagaggaa gaggatgacc gacccacca ggaggttctg    5160 aggcgcgccc cgctgatcag cctcgactgt gccttctagt tgccagccat ctgttgtttg    5220 ccctccccc gtgccttcct tgaccctgga aggtgccact cccactgtcc tttcctaata    5280
aaatgaggaa attgcatcgc attgtctgag taggtgtcat tctattctgg ggggtggggt    5340
ggggcaggac agcaagggg aggattggga agacaatagc aggcatgctg gggatgcggt    5400
gggctctatg gcgtacgcct cacgagcgcc ttcgcgcgct cgcggaaccc cgtggcttcc    5460
ccgacgcagc ccagcggcac ggagaaaggt agggccgggg tcgtgggatc cgggttccgg    5520
ccctgtgcgc gctctacccc gggccggcgg cctcgcccga cctcgcctgc gccccggggg    5580
cgctccaggc tttcgcgccg gttgcacaac ggccgcggcg gcgggcaagc gcgcactcgc    5640
ccgcccggcc cgacggctgc gccccgcccg ccgccgcgc cgcccgcaga ggggcgcggg    5700
cccgggggag ggctcgggc gccggcgact tggggtctcg ggcacgctgg caccgactgg    5760
tcggggaaca ccgagggcgg ccaagagcct tctctccgcc agggcctcgc atggggcgtc    5820
ggagctcctc ggcggccccg gccggccgcg ctcactcctc ggccctctcc gcagacgcgg    5880
ctgaggcccg gcgagaattc cagcgcgacg cgggcgggcc agcagtgctc ggggacccgg    5940
cgcatcctcc gcagctgctg gcccgggtgc taagcccctc gctgcccggg gccggcggcg    6000
ccggcggctt agtcccgctg cccggcgcgc ccggaggccg gccagtcccc cgaaccccg    6060 agctgcgcct ggaggcgccc ggcgcatcgg agccgctgca ccaccacccc tacaaatatc    6120
cggccgccgc ctacgaccac tatctcgggg ccaagagccg gccggcgccc tacccgctgc    6180
ccggcctgcg tggccacggc taccacccgc acgcgcatcc gcaccaccac caccaccccg    6240
tgagtccagc cgccgcggcc gccgccgccg ctgccgcagc tgccgcggcc gccaacaatt    6300
gtccggaatt ctgcagagtg gcggccgcac atgtgagcaa aaggccagca aaaggccagg    6360
aaccgtaaaa aggccgcgtt gctggcgttt ttccataggc tccgcccccc tgacgagcat    6420
cacaaaaatc gacgctcaag tcagaggtgg cgaaacccga caggactata agataccag    6480 gcgtttcccc ctggaagctc cctcgtgcgc tctcctgttc cgaccctgcc gcttaccgga    6540
```

| | |
|---|---:|
| tacctgtccg cctttctccc ttcgggaagc gtggcgcttt ctcatagctc acgctgtagg | 6600 |
| tatctcagtt cggtgtaggt cgttcgctcc aagctgggct gtgtgcacga accccccgtt | 6660 |
| cagcccgacc gctgcgcctt atccggtaac tatcgtcttg agtccaaccc ggtaagacac | 6720 |
| gacttatcgc cactggcagc agccactggt aacaggatta gcagagcgag gtatgtaggc | 6780 |
| ggtgctacag agttcttgaa gtggtggcct aactacggct acactagaag aacagtattt | 6840 |
| ggtatctgcg ctctgctgaa gccagttacc ttcggaaaaa gagttggtag ctcttgatcc | 6900 |
| ggcaaacaaa ccaccgctgg tagcggtggt ttttttgttt gcaagcagca gattacgcgc | 6960 |
| agaaaaaaag gatctcaaga agatcctttg atctttttcta cggggtctga cgctcagtgg | 7020 |
| aacgaaaact cacgttaagg gattttggtc atgagattat caaaaaggat cttcacctag | 7080 |
| atccttttaa attaaaaatg aagttttaaa tcaatctaaa gtatatatga gtaaacttgg | 7140 |
| tctgacagtt a | 7151 |

<210> SEQ ID NO 8
<211> LENGTH: 3872
<212> TYPE: DNA
<213> ORGANISM: Artificial Sequence
<220> FEATURE:
<223> OTHER INFORMATION: Tbx1 2nd donor vector

<400> SEQUENCE: 8

| | |
|---|---:|
| ccaatgctta atcagtgagg cacctatctc agcgatctgt ctatttcgtt catccatagt | 60 |
| tgcctgactc cccgtcgtgt agataactac gatacgggag ggcttaccat ctggccccag | 120 |
| tgctgcaatg ataccgcgag acccacgctc accggctcca gatttatcag caataaacca | 180 |
| gccagccgga agggccgagc gcagaagtgg tcctgcaact ttatccgcct ccatccagtc | 240 |
| tattaattgt tgccgggaag ctagagtaag tagttcgcca gttaatagtt tgcgcaacgt | 300 |
| tgttgccatt gctacaggca tcgtggtgtc acgctcgtcg tttggtatgg cttcattcag | 360 |
| ctccggttcc caacgatcaa ggcgagttac atgatccccc atgttgtgca aaaaagcggt | 420 |
| tagctccttc ggtcctccga tcgttgtcag aagtaagttg gccgcagtgt tatcactcat | 480 |
| ggttatggca gcactgcata attctcttac tgtcatgcca tccgtaagat gcttttctgt | 540 |
| gactggtgag tactcaacca agtcattctg agaatagtgt atgcggcgac cgagttgctc | 600 |
| ttgcccggcg tcaatacggg ataataccgc gccacatagc agaactttaa aagtgctcat | 660 |
| cattggaaaa cgttcttcgg ggcgaaaact ctcaaggatc ttaccgctgt tgagatccag | 720 |
| ttcgatgtaa cccactcgtg cacccaactg atcttcagca tcttttactt tcaccagcgt | 780 |
| ttctgggtga gcaaaaacag gaaggcaaaa tgccgcaaaa aagggaataa gggcgacacg | 840 |
| gaaatgttga atactcatac tcttcctttt tcaatattat tgaagcattt atcagggtta | 900 |
| ttgtctcatg agcggataca tatttgaatg tatttagaaa aataaacaaa tagggggttcc | 960 |
| gcgcacattt ccccgaaaag tgccacctga cgttaactcg agtcgacggc ccagtgaccc | 1020 |
| agcctcatct tggaattaag ggttttgccc aactcatcca ggaaactcat tgccaactca | 1080 |
| gacctcagcc catttcctgg ctcccacccc agatcctcag cccagcccca ccgctggagc | 1140 |
| tgattcccca ccttgtcttc cagattattc tgaattccat gcacagatac cagccccgct | 1200 |
| tccacgtggt ctatgtggac ccacgcaaag atagcgagaa atatgccgag gagaacttca | 1260 |
| aaacctttgt gttcgaggag acacgattca ccgcggtcac tgcctaccag aaccatcggg | 1320 |
| tgagggcctg tggggaggac ctgagcgat tcaacgcctc tggaaaagcg ggtgtaattt | 1380 |
| tcagttgccg tttggggaca gtgggtccgc ttagacctgc aggctgtggt cccagtggag | 1440 |

```
cccaacccaa ctggagcccc actcccaagg gcctcaggca gcccctccc tctcgaggct    1500 ggccggccca gcctcctatc agcttgacct ctccagcggc aactgtcact tcgtcctgaa   1560
agtttgtttt ccgaaccatt ccggaaactc cccatcaggg gcctgatctg aggtttaccc   1620
agattactag ggaacccgct ctgttcccca cccccaccc cactgcacgt ggggggtggt    1680
gaccacattc ctgtcccagc gaggagcaca gggcctccat ccccacccac ctgggggaca   1740
ccagagaggg gttccctagt gagagaggag gttcctcaga cccccgcccc cctgcaggag   1800
ggagcaccag ctccgtagag gaggggcaga cgtggactgg ttcttgtcag ggcagcagaa   1860
aggcccttgg tgcgcttctc ctaacactcc cctatcctcc gccgaggtcg ggtggcccag   1920
gctgcagggc tccagcggct tgctcacacc cacctccctg cagatcacgc agctcaagat   1980
tgccagcaat cccttcgcga aaggcttccg ggactgtgac cctgaggact ggtgagtgtc   2040
ctcccccgag agagtgagcg ccgggcgcct ggcgcaggcg ccgccctgat ccgcctcccg   2100
cccgcaggcc ccggaaccac cggcccgagc gcactgccgc tcatgagcgc cttcgcgcgc   2160
tcgcggaacc ccgtggcttc cccgacgcag cccagcggca cggagaaagg tagggccggg   2220
gtcgtgggat ccgggttccg gccctgtgcg cgctctaccc cgggccggcg gcctcgcccg   2280
acctcgcctg cgcccccggg gcgctccagg cttt cgcgcc ggttgcacaa cggccgcggc   2340
ggcgggcaag cgcgcactcg cccgcccggc ccgacggctg cgccccgccc gccgccgccg   2400
ccgcccgcag aggggcgcgg gccccgggga gggctcgggg cgccggcgac ttggggtctc   2460
gggcacgctg gcaccgactg gtcggggaac accgagggcg gccaagagcc ttctctccgc   2520
cagggcctcg catgggcgt cggagctcct cggcggcccc ggccggccgc gctcactcct    2580
cggccctctc cgcagacgcg gctgaggccc ggcgagaatt ccagcgcgac gcgggcgggc   2640
cagcagtgct cggggacccg gcgcatcctc cgcagctgct ggcccgggtg ctaagcccct   2700
cgctgcccgg ggccggcggc gccggcggct tagtcccgct gcccggcgcg cccggaggcc   2760
ggcccagtcc cccgaacccc gagctgcgcc tggaggcgcc cggcgcatcg gagccgctgc   2820
accaccaccc ctacaaatat ccggccgccg cctacgacca ctatctcggg gccaagagcc   2880
ggccggcgcc ctaccgctg cccggcctgc gtggccacgg ctaccacccg cacgcgcatc    2940
cgcaccacca ccaccacccc gtgagtccaa ccgccgcggc cgccgccgcc gctgccgcag   3000
ctgccgcggc cgccaacaat tgtccggaat tctgcagagt ggcggccgca catgtgagca   3060
aaaggccagc aaaaggccag gaaccgtaaa aaggccgcgt tgctggcgtt tttccatagg   3120
ctccgccccc ctgacgagca tcacaaaaat cgacgctcaa gtcagaggtg gcgaaacccg   3180
acaggactat aaagatacca ggcgtttccc cctggaagct ccctcgtgcg ctctcctgtt   3240
ccgaccctgc cgcttaccgg atacctgtcc gcctttctcc cttcgggaag cgtggcgctt   3300
tctcatagct cacgctgtag gtatctcagt tcggtgtagg tcgttcgctc caagctgggc   3360
tgtgtgcacg aaccccccgt tcagcccgac cgctgcgcct tatccggtaa ctatcgtctt   3420
gagtccaacc cggtaagaca cgacttatcg ccactggcag cagccactgg taacaggatt   3480
agcagagcga gtatgtagg cggtgctaca gagttcttga agtggtggcc taactacggc    3540
tacactagaa gaacagtatt tggtatctgc gctctgctga agccagttac cttcggaaaa   3600
agagttggta gctcttgatc cggcaaacaa accaccgctg gtagcggtgg ttttttgtt    3660 tgcaagcagc agattacgcg cagaaaaaaa ggatctcaag aagatccttt gatcttttct   3720
acggggtctg acgctcagtg gaacgaaaac tcacgttaag ggattttggt catgagatta   3780
```

| | |
|---|---|
| tcaaaaagga tcttcaccta gatccttta aattaaaaat gaagttttaa atcaatctaa | 3840 |
| agtatatatg agtaaacttg gtctgacagt ta | 3872 |

<210> SEQ ID NO 9
<211> LENGTH: 7132
<212> TYPE: DNA
<213> ORGANISM: Artificial Sequence
<220> FEATURE:
<223> OTHER INFORMATION: Runx1 1st donor vector

<400> SEQUENCE: 9

| | |
|---|---|
| ccaatgctta atcagtgagg cacctatctc agcgatctgt ctatttcgtt catccatagt | 60 |
| tgcctgactc cccgtcgtgt agataactac gatacgggag ggcttaccat ctggccccag | 120 |
| tgctgcaatg ataccgcgag acccacgctc accggctcca gatttatcag caataaacca | 180 |
| gccagccgga agggccgagc gcagaagtgg tcctgcaact ttatccgcct ccatccagtc | 240 |
| tattaattgt tgccgggaag ctagagtaag tagttcgcca gttaatagtt tgcgcaacgt | 300 |
| tgttgccatt gctacaggca tcgtggtgtc acgctcgtcg tttggtatgg cttcattcag | 360 |
| ctccggttcc caacgatcaa ggcgagttac atgatccccc atgttgtgca aaaaagcggt | 420 |
| tagctccttc ggtcctccga tcgttgtcag aagtaagttg gccgcagtgt tatcactcat | 480 |
| ggttatggca gcactgcata attctcttac tgtcatgcca tccgtaagat gcttttctgt | 540 |
| gactggtgag tactcaacca agtcattctg agaatagtgt atgcggcgac cgagttgctc | 600 |
| ttgcccggcg tcaatacggg ataataccgc gccacatagc agaactttaa aagtgctcat | 660 |
| cattggaaaa cgttcttcgg ggcgaaaact ctcaaggatc ttaccgctgt tgagatccag | 720 |
| ttcgatgtaa cccactcgtg cacccaactg atcttcagca tcttttactt tcaccagcgt | 780 |
| ttctgggtga gcaaaaacag gaaggcaaaa tgccgcaaaa aagggaataa gggcgacacg | 840 |
| gaaatgttga atactcatac tcttcctttt tcaatattat tgaagcattt atcagggtta | 900 |
| ttgtctcatg agcggataca tatttgaatg tatttagaaa aataaacaaa tagggggttcc | 960 |
| gcgcacattt ccccgaaaag tgccacctga cgttaactcg agtcgacaag cttccaatct | 1020 |
| tcctgggcgg taaattctga tagaaaccca tctccctgga cagtagcatc ctgggtgtcc | 1080 |
| cccgtcctcc taggcggtag catcctgggt ggtctccatc ctcccaggtg gtgtcatcct | 1140 |
| gggtggtctc cgtcctctca ggaggtggca tcctgagtgg tccccgacct cctgggcata | 1200 |
| gcatcatggg tagtccccat cctcttggga ggtgacatgc tgggtgatcc tcgtcatctc | 1260 |
| aggaggtggc atcctgggtg gtccctgtcc ccctgggtat agcatcctgg gtaatcctcg | 1320 |
| tcctcttggg agtagcatcc cgggtggtcc ccgtcctccc cagcagtagc atcctgggtg | 1380 |
| gcttcccatc ctcctaggcg gtatcatcct ggggtagcccc ctggggcaga gggaagagct | 1440 |
| gtggcctccg caacctccta ctcacttccg ctccgttctc ttgcccgccc tgcagcggca | 1500 |
| cccgacctga cagcgttcag cgacccgcgc cagttccccg cgctgccctc catctccgac | 1560 |
| ccccgcatgc actatccagg cgccttcacc tactccccga cgccggtcac ctcgggcatc | 1620 |
| ggcatcggca tgtcggccat gggctcggcc acgcgctacc acacctacct gccgccgccc | 1680 |
| taccccggct cgtcgcaagc gcagggaggc ccgttccaag ccagtcgcc ctcctaccac | 1740 |
| ctgtactacg gcgcctcggc cggctcctac cagttctcca tggtgggcgg cgagcgctcg | 1800 |
| ccgccgcgca tcctgccgcc ctgcaccaac gcctccaccg gctccgcgct gctcaaccc c | 1860 |
| agcctcccga accagagcga cgtggtggag gccgagggca gccacagcaa ctccccccac | 1920 |
| aacatggcgc cctccgcgcg cctggaggag gccgtgtgga ggcccctaccc tgcgatgagc | 1980 |

```
ggcagtgcgc tccgcgccgg gttttggcgc ctcccgcggg cgccccctc ctcacggcga    2040 gcgctgccac gtcagacgaa gggcgcagcg agcgtcctga tccttccgcc cggacgctca    2100
ggacagcggc ccgctgctca taagactcgg ccttagaacc ccagtatcag cagaaggaca    2160
ttttaggacg ggacttgggt gactctaggg cactggtttt ctttccagag agcggaacag    2220
gcgaggaaaa gtagtccctt ctcggcgatt ctgcggaggg atctccgtgg ggcggtgaac    2280
gccgatgatt atataaggac gcgccgggtg tggcacagct agttccgtcg cagccgggat    2340
ttgggtcgcg gttcttgttt gtggatcgct gtgatcgtca cttggtgagt agcgggctgc    2400
tgggctggcc ggggctttcg tggccgccgg gccgctcgt gggacggaag cgtgtggaga     2460
gaccgccaag ggctgtagtc tgggtccgcg agcaaggttg ccctgaactg ggggttgggg    2520
ggagcgcagc aaaatggcgg ctgttcccga gtcttgaatg gaagacgctt gtgaggcggg    2580
ctgtgaggtc gttgaaacaa ggtgggggc atggtgggcg gcaagaaccc aaggtcttga     2640
ggccttcgct aatgcgggaa agctcttatt cgggtgagat gggctgggc accatctggg     2700 gaccctgacg tgaagtttgt cactgactgg agaactcggt ttgtcgtctg ttgcggggc     2760 ggcagttatg gcggtgccgt tgggcagtgc accgtacct ttgggagcgc gcgccctcgt     2820
cgtgtcgtga cgtcacccgt tctgttggct tataatgcag ggtggggcca cctgccggta    2880
ggtgtgcggt aggcttttct ccgtcgcagg acgcagtgtt cgggcctagg gtaggctctc    2940
ctgaatcgac aggcgccgga cctctggtga ggggagggat aagtgaggcg tcagtttctt    3000
tggtcggttt tatgtaccta tcttcttaag tagctgaagc tccggttttg aactatgcgc    3060
tcggggttgg cgagtgtgtt ttgtgaagtt ttttaggcac cttttgaaat gtaatcattt    3120
gggtcaatat gtaattttca gtgttagact agtaaattgt ccgctaaatt ctggccgttt    3180
ttggcttttt tgttagacgg taccgagctc ttcgaaggat ccatcgccac catggtgagc    3240
aagggcgagg aggataacat ggccatcatc aaggagttca tgcgcttcaa ggtgcacatg    3300
gagggctccg tgaacggcca cgagttcgag atcgagggcg agggcgaggg ccgcccctac    3360
gagggcaccc cagaccgccaa gctgaaggtg accaagggtg gccccctgcc cttcgcctgg    3420
gacatcctgt cccctcagtt catgtacggc tccaaggcct acgtgaagca ccccgccgac    3480
atccccgact acttgaagct gtccttcccc gagggcttca gtgggagcg cgtgatgaac    3540 ttcgaggacg gcggcgtggt gaccgtgacc caggactcct ccctgcagga cggcgagttc    3600
atctacaagg tgaagctgcg cggcaccaac ttcccctccg acggccccgt aatgcagaag    3660
aagaccatgg gctgggaggc ctcctccgag cggatgtacc ccgaggacgg cgccctgaag    3720
ggcgagatca gcagaggct gaagctgaag gacggcggcc actacgacgc tgaggtcaag     3780
accacctaca aggccaagaa gcccgtgcag ctgcccggcg cctacaacgt caacatcaag    3840
ttggacatca cctcccacaa cgaggactac accatcgtgg aacagtacga acgcgccgag    3900
ggccgccact ccaccggcgg catggacgag ctgtacaagg agggcagggg cagcctgctg    3960
acctgcggcg acgtggagga gaaccccggc cccatgcccc ccccaggct gctgttcttc     4020 ctgctgttcc tgaccccat ggaggtgagg cccgaggagc cctggtggt gaaggtggag      4080 gagggcgaca acgccgtgct gcagtgcctg aagggcacca cgacggccc cacccagcag    4140 ctgacctgga gcagggagag cccctgaag cccttcctga agctgagcct gggcctgccc     4200
ggcctgggca tccacatgag gcccctgccc atctggctgt tcatcttcaa cgtgagccag    4260
cagatgggcg gcttctacct gtgccagccc ggccccccca gcgagaaggc ctggcagccc    4320
```

-continued

```
ggctggaccg tgaacgtgga gggcagcggc gagctgttca ggtggaacgt gagcgacctg    4380
ggcggcctgg gctgcggcct gaagaacagg agcagcgagg cccccagcag ccccagcggc    4440
aagctgatga gccccaagct gtacgtgtgg gccaaggaca ggcccgagat ctgggagggc    4500 gagccccccct gcctgccccc cagggacagc ctgaaccaga gcctgagcca ggacctgacc    4560
atggcccccg gcagcaccct gtggctgagc tgcggcgtgc cccccgacag cgtgagcagg    4620
ggccccctga gctggaccca cgtgcacccc aagggcccca agagcctgct gagcctggag    4680
ctgaaggacg acaggcccgc cagggacatg tgggtgatgg agaccggcct gctgctgccc    4740
agggccaccg cccaggacgc cggcaagtac tactgccaca ggggcaacct gaccatgagc    4800
ttccacctgg agatcaccgc caggcccgtg ctgtggcact ggctgctgag gaccggcggc    4860
tggaaggtga gcgccgtgac cctggcctac ctgatcttct gcctgtgcag cctggtgggc    4920
atcctgcacc tgcagagggc cctggtgctg aggaggaaga ggaagaggat gaccgacccc    4980
accaggaggt tctgaggcgc gccccgctga tcagcctcga ctgtgccttc tagttgccag    5040
ccatctgttg tttgccccctc ccccgtgcct tccttgaccc tggaaggtgc cactcccact    5100
gtcctttcct aataaaatga ggaaattgca tcgcattgtc tgagtaggtg tcattctatt    5160 ctgggggtg gggtggggca ggacagcaag ggggaggatt gggaagacaa tagcaggcat    5220
gctggggatg cggtgggctc tatggcgtac gccttgaggc gccaggcctg gcccggctgg    5280
gccacgcggg ccgccgcctt cgcctccggg cgcgcgggcc tcctgttcgc gacaagcccg    5340
ccgggatccc gggccctggg cccggccacc gtcctgggc cgagggcgcc cgacggccag    5400
gatctcgctg taggtcaggc ccgcgcagcc tcctgcgccc agaagcccac gccgccgccg    5460
tctgctggcg ccccggccct cgcggaggtg tccgaggcga cgcacctcga gggtgtccgc    5520 cggcccagc acccagggga cgcgctggaa agcaaacagg aagattcccg agggaaact    5580 gtgaatgctt ctgatttagc aatgctgtga ataaaaagaa agattttata cccttgactt    5640
aactttttaa ccaagttgtt tattccaaag agtgtgaat tttggttggg gtgggggag    5700 aggagggatg caactcgccc tgtttggcat ctaattctta ttttaatttt ttccgcacct    5760
tatcaattgc aaaatgcgta tttgcatttg ggtggttttt attttatat acgtttatat    5820 aaatatatat aaattgagct tgcttctttc ttgctttgac catggaaaga aatatgattc    5880
cctttctttt aagttttatt taactttcct tttggacttt tgggtagttg tttttttttg    5940
ttttgttttg ttttttttgag aaacagctac agctttgggt catttttaac tactgtattc    6000
ccacaaggaa tccccagata tttatgtatc ttgatgttca gacatttatg tgttgataat    6060
tttttaatta tttaaatgta cttatattaa gaaaaatatc aagtactaca ttttcttttg    6120
ttcttgatag tagccaaagt taaatgtatc acattgaaga aggctagaaa aaaagaatga    6180
gtaatgtgat cgcttggtta ccagaagta ttgtttacat taaactccct ttcatgttaa    6240
tcaaacaagt gagtagctca cgcatgacgt acgcgtcaat tgtccggaat tctgcagagt    6300
ggcggccgca catgtgagca aaaggccagc aaaaggccag gaaccgtaaa aaggccgcgt    6360
tgctggcgtt tttccatagg ctccgccccc ctgacgagca tcacaaaaat cgacgctcaa    6420
gtcagaggtg gcgaaacccg acaggactat aaagatacca ggcgtttccc cctggaagct    6480
ccctcgtgcg ctctcctgtt ccgaccctgc cgcttaccgg atacctgtcc gcctttctcc    6540
cttcgggaag cgtggcgctt tctcatagct cacgctgtag gtatctcagt tcggtgtagg    6600
tcgttcgctc caagctgggc tgtgtgcacg aaccccccgt tcagcccgac cgctgcgcct    6660
tatccggtaa ctatcgtctt gagtccaacc cggtaagaca cgacttatcg ccactggcag    6720
```

```
cagccactgg taacaggatt agcagagcga ggtatgtagg cggtgctaca gagttcttga    6780
agtggtggcc taactacggc tacactagaa gaacagtatt tggtatctgc gctctgctga    6840
agccagttac cttcggaaaa agagttggta gctcttgatc cggcaaacaa accaccgctg    6900
gtagcggtgg ttttttttgtt tgcaagcagc agattacgcg cagaaaaaaa ggatctcaag    6960
aagatccttt gatcttttct acggggtctg acgctcagtg gaacgaaaac tcacgttaag    7020
ggattttggt catgagatta tcaaaaagga tcttcaccta gatcctttta aattaaaaat    7080
gaagttttaa atcaatctaa agtatatatg agtaaacttg gtctgacagt ta            7132
```

<210> SEQ ID NO 10
<211> LENGTH: 4617
<212> TYPE: DNA
<213> ORGANISM: Artificial Sequence
<220> FEATURE:
<223> OTHER INFORMATION: Runx1 2nd donor vector

<400> SEQUENCE: 10

```
ccaatgctta atcagtgagg cacctatctc agcgatctgt ctatttcgtt catccatagt      60
tgcctgactc cccgtcgtgt agataactac gatacgggag ggcttaccat ctggccccag     120
tgctgcaatg ataccgcgag acccacgctc accggctcca gatttatcag caataaacca     180
gccagccgga agggccgagc gcagaagtgg tcctgcaact ttatccgcct ccatccagtc     240
tattaattgt tgccgggaag ctagagtaag tagttcgcca gttaatagtt tgcgcaacgt     300
tgttgccatt gctacaggca tcgtggtgtc acgctcgtcg tttggtatgg cttcattcag     360
ctccggttcc caacgatcaa ggcgagttac atgatccccc atgttgtgca aaaaagcggt     420
tagctccttc ggtcctccga tcgttgtcag aagtaagttg gccgcagtgt tatcactcat     480
ggttatggca gcactgcata attctcttac tgtcatgcca tccgtaagat gcttttctgt     540
gactggtgag tactcaacca agtcattctg agaatagtgt atgcggcgac cgagttgctc     600
ttgcccggcg tcaatacggg ataataccgc gccacatagc agaactttaa aagtgctcat     660
cattggaaaa cgttcttcgg ggcgaaaact ctcaaggatc ttaccgctgt tgagatccag     720
ttcgatgtaa cccactcgtg cacccaactg atcttcagca tcttttactt tcaccagcgt     780
ttctgggtga gcaaaaacag gaaggcaaaa tgccgcaaaa aagggaataa gggcgacacg     840
gaaatgttga atactcatac tcttcctttt tcaatattat tgaagcattt atcagggtta     900
ttgtctcatg agcggataca tatttgaatg tatttagaaa aataaacaaa taggggttcc     960
gcgcacattt ccccgaaaag tgccacctga cgttaactcg agtcgacaag cttccaatct    1020
tcctgggcgg taaattctga tagaacccca tctccctgga cagtagcatc ctgggtgtcc    1080
cccgtcctcc taggcggtag catcctgggt ggtctccatc ctccaggtg tgtcatcct     1140 gggtggtctc cgtcctctca ggaggtggca tcctgagtgg tccccgacct cctgggcata    1200
gcatcatggg tagtccccat cctcttggga ggtgacatgc tgggtgatcc tcgtcatctc    1260
aggaggtggc atcctgggtg gtccctgtcc ccctgggtat agcatcctgg gtaatcctcg    1320
tcctcttggg agtagcatcc cgggtggtcc ccgtcctccc cagcagtagc atcctgggtg    1380
gcttcccatc ctcctaggcg gtatcatcct gggtagcccc ctgggcaga gggaagagct    1440 gtggcctccg caacctccta ctcacttccg ctccgttctc ttgcccgccc tgcagcggca    1500
cccgacctga cagcgttcag cgaccgcgcg cagttcccg cgctgccctc catctccgac    1560
ccccgcatgc actatccagg cgccttcacc tactcccga cgccggtcac ctcgggcatc    1620
```

```
ggcatcggca tgtcggccat gggctcggcc acgcgctacc acacctacct gccgccgccc    1680
taccccggct cgtcgcaagc gcagggaggc ccgttccaag ccagctcgcc ctcctaccac    1740
ctgtactacg gcgcctcggc cggctcctac cagttctcca tggtgggcgg cgagcgctcg    1800
ccgccgcgca tcctgccgcc ctgcaccaac gcctccaccg gctccgcgct gctcaacccc    1860
agcctcccga accagagcga cgtggtggag gccgagggca gccacagcaa ctcccccacc    1920
aacatggcgc cctccgcgcg cctggaggag gccgtgtgga ggcctacgg atcaggagag    1980 gggagaggat ccctgctgac ttgcggggat gtggaagaga ccctggacc gatggtgagc    2040 aagggcgagg agaataacat ggccatcatc aaggagttca tgcgcttcaa ggtgcgcatg    2100
gagggctccg tgaacggcca cgagttcgag atcgagggcg agggcgaggg ccgcccctac    2160
gagggctttc agaccgctaa gctgaaggtg accaagggtg cccctgcc cttcgcctgg    2220 gacatcctgt cccctcagtt cacctacggc tccaaggcct acgtgaagca cccgccgac    2280 atccccgact acttcaagct gtccttcccc gagggcttca gtgggagcg cgtgatgaac    2340 ttcgaggacg gcggcgtggt gaccgtgacc caggactcct ccctgcagga cggcgagttc    2400
atctacaagg tgaagctgcg cggcaccaac ttcccctccg acggccccgt aatgcagaag    2460
aagaccatgg gctgggaggc ctcctccgag cggatgtacc ccgaggacgg cgccctgaag    2520
ggcgagatca agatgaggct gaagctgaag gacggcggcc actacacctc cgaggtcaag    2580
accacctaca aggccaagaa gcccgtgcag ctgcccggcg cctacatcgt cggcatcaag    2640
ttggacatca cctcccacaa cgaggactac accatcgtgg aacagtacga acgcgccgag    2700
ggccgccact ccaccggcgg catggacgag ctgtacaagt gaggcgccag gcctggcccg    2760
gctgggccac gcgggccgcc gccttcgcct ccgggcgcgc gggcctcctg ttcgcgacaa    2820
gcccgccggg atcccgggcc ctgggcccgg ccaccgtcct ggggccgagg gcgcccgacg    2880
gccaggatct cgctgtaggt caggcccgcg cagcctcctg cgcccagaag cccacgccgc    2940
cgccgtctgc tggcgccccg gccctcgcgg aggtgtccga ggcgacgcac ctcgagggtg    3000
tccgccggcc ccagcaccca ggggacgcgc tggaaagcaa acaggaagat tcccggaggg    3060
aaactgtgaa tgcttctgat ttagcaatgc tgtgaataaa agaaagatt ttataccctt    3120 gacttaactt tttaaccaag ttgtttattc caaagagtgt ggaattttgg ttggggtggg    3180
gggagaggag ggatgcaact cgccctgttt ggcatctaat tcttatttt aattttccg    3240 caccttatca attgcaaaat gcgtatttgc atttgggtgg ttttattt tatatacgtt    3300 tatataaata tatataaatt gagcttgctt ctttcttgct ttgaccatgg aaagaaatat    3360
gattcccttt tctttaagtt ttatttaact tttcttttgg acttttgggt agttgttttt    3420
ttttgttttg ttttgttttt ttgagaaaca gctacagctt tgggtcattt ttaactactg    3480
tattcccaca aggaatcccc agatatttat gtatcttgat gttcagacat ttatgtgttg    3540 ataattttt aattatttaa atgtacttat attaagaaaa atatcaagta ctacattttc    3600
ttttgttctt gatagtagcc aaagttaaat gtatcacatt gaagaaggct agaaaaaaag    3660
aatgagtaat gtgatcgctt ggttatccag aagtattgtt tacattaaac tccctttcat    3720
gttaatcaaa caagtgagta gctcacgcat gacgtacgcg tcaattgtcc ggaattctgc    3780
agagtggcgg ccgcacatgt gagcaaaagg ccagcaaaag gccaggaacc gtaaaaaggc    3840
cgcgttgctg gcgttttcc ataggctccg ccccctgac gagcatcaca aaatcgacg    3900 ctcaagtcag aggtggcgaa acccgacagg actataaga taccaggcgt tcccctgg    3960 aagctccctc gtgcgctctc ctgttccgac cctgccgctt accggatacc tgtccgcctt    4020
```

```
tctcccttcg ggaagcgtgg cgctttctca tagctcacgc tgtaggtatc tcagttcggt    4080
gtaggtcgtt cgctccaagc tgggctgtgt gcacgaaccc cccgttcagc ccgaccgctg    4140
cgccttatcc ggtaactatc gtcttgagtc caacccggta agacacgact tatcgccact    4200
ggcagcagcc actggtaaca ggattagcag agcgaggtat gtaggcggtg ctacagagtt    4260
cttgaagtgg tggcctaact acggctacac tagaagaaca gtatttggta tctgcgctct    4320
gctgaagcca gttaccttcg gaaaaagagt tggtagctct tgatccggca aacaaaccac    4380
cgctggtagc ggtggttttt tgtttgcaa gcagcagatt acgcgcagaa aaaaggatc    4440 tcaagaagat cctttgatct tttctacggg gtctgacgct cagtggaacg aaaactcacg    4500
ttaagggatt ttggtcatga gattatcaaa aaggatcttc acctagatcc ttttaaatta    4560
aaaatgaagt tttaaatcaa tctaaagtat atatgagtaa acttggtctg acagtta      4617
```

<210> SEQ ID NO 11
<211> LENGTH: 24
<212> TYPE: DNA
<213> ORGANISM: Artificial Sequence
<220> FEATURE:
<223> OTHER INFORMATION: forward primer for detection of marker-
      integrated Tbx1
<220> FEATURE:
<221> NAME/KEY: source
<222> LOCATION: (1)..(24)
<223> OTHER INFORMATION: sequence is synthesized

<400> SEQUENCE: 11
gaggattggg aagacaatag cagg                                            24

<210> SEQ ID NO 12
<211> LENGTH: 20
<212> TYPE: DNA
<213> ORGANISM: Artificial Sequence
<220> FEATURE:
<223> OTHER INFORMATION: reverse primer for detection of marker-
      integrated Tbx1
<220> FEATURE:
<221> NAME/KEY: source
<222> LOCATION: (1)..(20)
<223> OTHER INFORMATION: sequence is synthesized

<400> SEQUENCE: 12
gcctccgacc gggcgctttg                                                 20

<210> SEQ ID NO 13
<211> LENGTH: 23
<212> TYPE: DNA
<213> ORGANISM: Artificial Sequence
<220> FEATURE:
<223> OTHER INFORMATION: forward primer for detection and sequencing of
      marker-free Tbx1
<220> FEATURE:
<221> NAME/KEY: source
<222> LOCATION: (1)..(23)
<223> OTHER INFORMATION: sequence is synthesized

<400> SEQUENCE: 13
ggcccagtga cccagcctca tct                                             23

<210> SEQ ID NO 14
<211> LENGTH: 20
<212> TYPE: DNA
<213> ORGANISM: Artificial Sequence
<220> FEATURE:
<223> OTHER INFORMATION: reverse primer for detection and sequencing of

```
      marker-free Tbx1
<220> FEATURE:
<221> NAME/KEY: source
<222> LOCATION: (1)..(20)
<223> OTHER INFORMATION: sequence is synthesized

<400> SEQUENCE: 14
gcctccgacc gggcgctttg                                              20

<210> SEQ ID NO 15
<211> LENGTH: 21
<212> TYPE: DNA
<213> ORGANISM: Artificial Sequence
<220> FEATURE:
<223> OTHER INFORMATION: marker-free Tbx1 read sequence
<220> FEATURE:
<221> NAME/KEY: source
<222> LOCATION: (1)..(21)
<223> OTHER INFORMATION: sequence is synthesized

<400> SEQUENCE: 15
gctgcagggc tccagcggct t                                            21

<210> SEQ ID NO 16
<211> LENGTH: 20
<212> TYPE: DNA
<213> ORGANISM: Artificial Sequence
<220> FEATURE:
<223> OTHER INFORMATION: forward primer for detection of Runx1
<220> FEATURE:
<221> NAME/KEY: source
<222> LOCATION: (1)..(20)
<223> OTHER INFORMATION: sequence is synthesized

<400> SEQUENCE: 16
gggtggcaga ttctgggtag                                              20

<210> SEQ ID NO 17
<211> LENGTH: 20
<212> TYPE: DNA
<213> ORGANISM: Artificial Sequence
<220> FEATURE:
<223> OTHER INFORMATION: reverse primer for detection of Runx1
<220> FEATURE:
<221> NAME/KEY: source
<222> LOCATION: (1)..(20)
<223> OTHER INFORMATION: sequence is synthesized

<400> SEQUENCE: 17
cagcctggtg aaagcaacac                                              20

<210> SEQ ID NO 18
<211> LENGTH: 21
<212> TYPE: DNA
<213> ORGANISM: Artificial Sequence
<220> FEATURE:
<223> OTHER INFORMATION: alternate UbC promoter forward primer
<220> FEATURE:
<221> NAME/KEY: source
<222> LOCATION: (1)..(21)
<223> OTHER INFORMATION: sequence is synthesized

<400> SEQUENCE: 18
tgcgggaaag ctcttattcg g                                            21

<210> SEQ ID NO 19
<211> LENGTH: 22
<212> TYPE: DNA
<213> ORGANISM: Artificial Sequence
```

```
<220> FEATURE:
<223> OTHER INFORMATION: alternate UbC promoter reverse primer
<220> FEATURE:
<221> NAME/KEY: source
<222> LOCATION: (1)..(22)
<223> OTHER INFORMATION: sequence is synthesized

<400> SEQUENCE: 19
caaaaacggc cagaatttag cg                                              22

<210> SEQ ID NO 20
<211> LENGTH: 22
<212> TYPE: DNA
<213> ORGANISM: Artificial Sequence
<220> FEATURE:
<223> OTHER INFORMATION: RUNX1 gRNA
<220> FEATURE:
<221> NAME/KEY: source
<222> LOCATION: (1)..(22)
<223> OTHER INFORMATION: sequence is synthesized

<400> SEQUENCE: 20
ccgtatggag tccctactga gg                                              22

<210> SEQ ID NO 21
<211> LENGTH: 22
<212> TYPE: DNA
<213> ORGANISM: Artificial Sequence
<220> FEATURE:
<223> OTHER INFORMATION: GFI1 gRNA
<220> FEATURE:
<221> NAME/KEY: source
<222> LOCATION: (1)..(22)
<223> OTHER INFORMATION: sequence is synthesized

<400> SEQUENCE: 21
agggctcaaa tgaggaccca gg                                              22

<210> SEQ ID NO 22
<211> LENGTH: 23
<212> TYPE: DNA
<213> ORGANISM: Artificial Sequence
<220> FEATURE:
<223> OTHER INFORMATION: GFI1 gRNA
<220> FEATURE:
<221> NAME/KEY: source
<222> LOCATION: (1)..(23)
<223> OTHER INFORMATION: sequence is synthesized

<400> SEQUENCE: 22
atgggttcaa atgagcaacc tgg                                             23

<210> SEQ ID NO 23
<211> LENGTH: 22
<212> TYPE: DNA
<213> ORGANISM: Artificial Sequence
<220> FEATURE:
<223> OTHER INFORMATION: GFI1 gRNA
<220> FEATURE:
<221> NAME/KEY: source
<222> LOCATION: (1)..(22)
<223> OTHER INFORMATION: sequence is synthesized

<400> SEQUENCE: 23
atgggctcaa atgagcctct gg                                              22

<210> SEQ ID NO 24
<211> LENGTH: 20
<212> TYPE: DNA
```

-continued

```
<213> ORGANISM: Artificial Sequence
<220> FEATURE:
<223> OTHER INFORMATION: forward primer for detection of GFI1
<220> FEATURE:
<221> NAME/KEY: source
<222> LOCATION: (1)..(20)
<223> OTHER INFORMATION: sequence is synthesized

<400> SEQUENCE: 24
aatgccatgc tgggctattg                                          20

<210> SEQ ID NO 25
<211> LENGTH: 20
<212> TYPE: DNA
<213> ORGANISM: Artificial Sequence
<220> FEATURE:
<223> OTHER INFORMATION: reverse primer for detection of GFI1
<220> FEATURE:
<221> NAME/KEY: source
<222> LOCATION: (1)..(20)
<223> OTHER INFORMATION: sequence is synthesized

<400> SEQUENCE: 25
ccagctttcc ccctacagac                                          20

<210> SEQ ID NO 26
<211> LENGTH: 21
<212> TYPE: DNA
<213> ORGANISM: Artificial Sequence
<220> FEATURE:
<223> OTHER INFORMATION: forward primer for detection of B2M
<220> FEATURE:
<221> NAME/KEY: source
<222> LOCATION: (1)..(21)
<223> OTHER INFORMATION: sequence is synthesized

<400> SEQUENCE: 26
atgcagcgca atctccagtg a                                        21

<210> SEQ ID NO 27
<211> LENGTH: 22
<212> TYPE: DNA
<213> ORGANISM: Artificial Sequence
<220> FEATURE:
<223> OTHER INFORMATION: reverse primer for detection of B2M
<220> FEATURE:
<221> NAME/KEY: source
<222> LOCATION: (1)..(22)
<223> OTHER INFORMATION: sequence is synthesized

<400> SEQUENCE: 27
gtagctgcag acagttctcc aa                                       22

<210> SEQ ID NO 28
<211> LENGTH: 20
<212> TYPE: DNA
<213> ORGANISM: Artificial Sequence
<220> FEATURE:
<223> OTHER INFORMATION: forward primer for detection of random
      integration 1
<220> FEATURE:
<221> NAME/KEY: source
<222> LOCATION: (1)..(20)
<223> OTHER INFORMATION: sequence is synthesized

<400> SEQUENCE: 28
aaggatcagg acgctcgctg                                          20

<210> SEQ ID NO 29
```

```
<211> LENGTH: 28
<212> TYPE: DNA
<213> ORGANISM: Artificial Sequence
<220> FEATURE:
<223> OTHER INFORMATION: reverse primer for detection of random
      integration 1
<220> FEATURE:
<221> NAME/KEY: source
<222> LOCATION: (1)..(28)
<223> OTHER INFORMATION: sequence is synthesized

<400> SEQUENCE: 29
gtctcatgag cggatacata tttgaatg                                        28

<210> SEQ ID NO 30
<211> LENGTH: 20
<212> TYPE: DNA
<213> ORGANISM: Artificial Sequence
<220> FEATURE:
<223> OTHER INFORMATION: forward primer for detection of random
      integration 2
<220> FEATURE:
<221> NAME/KEY: source
<222> LOCATION: (1)..(20)
<223> OTHER INFORMATION: sequence is synthesized

<400> SEQUENCE: 30
cacctctgac ttgagcgtcg                                                 20

<210> SEQ ID NO 31
<211> LENGTH: 27
<212> TYPE: DNA
<213> ORGANISM: Artificial Sequence
<220> FEATURE:
<223> OTHER INFORMATION: reverse primer for detection of random
      integration 2
<220> FEATURE:
<221> NAME/KEY: source
<222> LOCATION: (1)..(27)
<223> OTHER INFORMATION: sequence is synthesized

<400> SEQUENCE: 31
ggaaattgca tcgcattgtc tgagtag                                         27

<210> SEQ ID NO 32
<211> LENGTH: 22
<212> TYPE: DNA
<213> ORGANISM: Artificial Sequence
<220> FEATURE:
<223> OTHER INFORMATION: TBX1 reference cDNA
<220> FEATURE:
<221> NAME/KEY: source
<222> LOCATION: (1)..(22)
<223> OTHER INFORMATION: sequence is synthesized

<400> SEQUENCE: 32
ccaccggccc ggcgcactgc cg                                              22

<210> SEQ ID NO 33
<211> LENGTH: 22
<212> TYPE: DNA
<213> ORGANISM: Artificial Sequence
<220> FEATURE:
<223> OTHER INFORMATION: TBX1 c. 928G>A
<220> FEATURE:
<221> NAME/KEY: source
<222> LOCATION: (1)..(22)
<223> OTHER INFORMATION: sequence is synthesized

<400> SEQUENCE: 33
```
ccaccggccc agcgcactgc cg                                              22

<210> SEQ ID NO 34
<211> LENGTH: 22
<212> TYPE: DNA
<213> ORGANISM: Artificial sequence
<220> FEATURE:
<223> OTHER INFORMATION: Description of sequence: Consensus sequence

<400> SEQUENCE: 34
ccaccggccc rgcgcactgc cg                                              22

<210> SEQ ID NO 35
<211> LENGTH: 91
<212> TYPE: DNA
<213> ORGANISM: Artificial sequence
<220> FEATURE:
<223> OTHER INFORMATION: Description of sequence: FIG. 6A TBX1 exon 8

<400> SEQUENCE: 35
tcccgcccgc aggccccgga accaccggcc cggcgcactg ccgctcatga gcgccttcgc     60
gcgctcgcgg aaccccgtgg cttccccgac g                                   91

<210> SEQ ID NO 36
<211> LENGTH: 91
<212> TYPE: DNA
<213> ORGANISM: Artificial sequence
<220> FEATURE:
<223> OTHER INFORMATION: Description of sequence: FIG. 6A edited
      sequence

<400> SEQUENCE: 36
tcccgcccgc aggccccgga accaccggcc cagcgcactg ccgctcatcg aaggtctaga     60
ctccgcgccg ggttttggcg cctcccgcgg g                                   91

<210> SEQ ID NO 37
<211> LENGTH: 90
<212> TYPE: DNA
<213> ORGANISM: Artificial sequence
<220> FEATURE:
<223> OTHER INFORMATION: Description of sequence: FIG. 6B RUNX1 exon 9

<400> SEQUENCE: 37
ggcgccctcc gcgcgcctgg aggaggccgt gtggaggccc tacgaggcgc caggcctggc     60
ccggctgggc cacgcgggcc gccgccttcg                                     90

<210> SEQ ID NO 38
<211> LENGTH: 89
<212> TYPE: DNA
<213> ORGANISM: Artificial sequence
<220> FEATURE:
<223> OTHER INFORMATION: Description of sequence: FIG. 6B edited
      sequence

<400> SEQUENCE: 38
ggcgccctcc gcgcgcctgg aggaggccgt gtggaggccc taccctgcga tgagcggcag    60
tgcgtccgcg ccggttttgg cgcctcccg                                      89

<210> SEQ ID NO 39
<211> LENGTH: 91
<212> TYPE: DNA
<213> ORGANISM: Artificial sequence
<220> FEATURE:
<223> OTHER INFORMATION: Description of sequence: FIG. 6C GFI1 exon 7

```
<400> SEQUENCE: 39
aggaaggtgg acctccgaag gcaccgggag acgcagcatg ggctaaatga gcaccctggc    60
ttggctgcaa gcagcagcta cacaacacta c                                  91

<210> SEQ ID NO 40
<211> LENGTH: 90
<212> TYPE: DNA
<213> ORGANISM: Artificial sequence
<220> FEATURE:
<223> OTHER INFORMATION: Description of sequence: FIG 6C GFI1 edited
      sequence

<400> SEQUENCE: 40
aggaaggtgg acctccgaag gcaccgggag acgcagcatg ggctaaaccc taccctgcga    60
tgagcggcag tccgcgccgg gttttggcgc                                    90

Figure 6D:
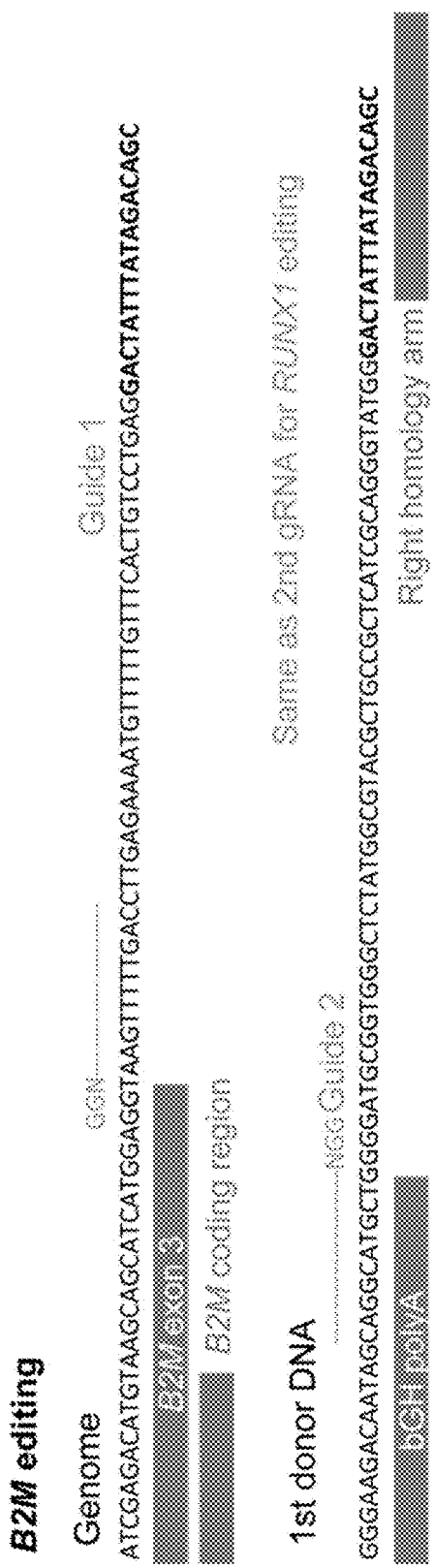

<210> SEQ ID NO 41
<211> LENGTH: 91
<212> TYPE: DNA
<213> ORGANISM: Artificial sequence
<220> FEATURE:
<223> OTHER INFORMATION: Description of sequence: FIG 6D B2M

<400> SEQUENCE: 41
atcgagacat gtaagcagca tcatggaggt aagttttga ccttgagaaa atgttttgt      60 ttcactgtcc tgaggactat ttatagacag c                                  91

<210> SEQ ID NO 42
<211> LENGTH: 91
<212> TYPE: DNA
<213> ORGANISM: Artificial sequence
<220> FEATURE:
<223> OTHER INFORMATION: Description of sequence: FIG 6D edited sequence

<400> SEQUENCE: 42
gggaagacaa tagcaggcat gctggggatg cggtgggctc tatggcgtac gctgccgctc    60
atcgcagggt atgggactat ttatagacag c                                  91

<210> SEQ ID NO 43
<211> LENGTH: 20
<212> TYPE: DNA
<213> ORGANISM: Artificial sequence
<220> FEATURE:
<223> OTHER INFORMATION: Description of sequence: FIG 7A unedited clone
      #14

<400> SEQUENCE: 43
ccggcccggc gcactgccgc                                               20

<210> SEQ ID NO 44
<211> LENGTH: 21
<212> TYPE: DNA
<213> ORGANISM: Artificial sequence
<220> FEATURE:
<223> OTHER INFORMATION: Description of sequence: FIG 7A edited clone
      #14

<400> SEQUENCE: 44
ccggcccggc ggcactgccg c                                             21
```

SCARLESS GENOME EDITING THROUGH TWO-STEP HOMOLOGY DIRECTED REPAIR

CROSS-REFERENCE TO RELATED APPLICATIONS

This application is a continuation of International Application No. PCT/US2018/042702, filed Jul. 18, 2018, which claims priority to U.S. Provisional Application No. 62/533,780 filed Jul. 18, 2017, the disclosures of which are hereby incorporated by reference in their entirety for all purposes.

REFERENCE TO A "SEQUENCE LISTING," A TABLE, OR A COMPUTER PROGRAM LISTING APPENDIX SUBMITTED ON A COMPACT DISK

The Sequence Listing written in file 079445-002110US-1173059 SequenceListing.txt created on Feb. 7, 2023, 44,773 bytes in size, for machine format IBM-PC, MS-Windows operating system, is hereby incorporated by reference in its entirety for all purposes.

TECHNICAL FIELD

The present invention pertains generally to the field of genome engineering and scarless genome editing. In particular, the invention relates to a method of scarless genome editing utilizing homology directed repair (HDR) to genetically modify cells and remove unwanted sequences.

BACKGROUND

Precise genome editing has been made possible by creating a DNA double-stranded break (DSB) at a specific site in the genome (Jasin Trends Genet. 12, 224-228 (1996)). The creation of the DSB has been done using programmable zinc-finger nucleases (ZFNs) and transcription activator-like effector nucleases (TALENs, Porteus Annu. Rev. Pharmacol. Toxicol. 56, 163-190 (2016)). The advent of the clustered regularly interspaced short palindromic repeats (CRISPR)/Cas9/guide RNA system (Cas9/gRNA), however, has enabled targeted cleavage with unprecedented ease of use, efficiency, and specificity. Each of these nuclease systems stimulate genome editing by initiating sequence-specific double stranded breaks (DSBs), which can then be repaired by either non-homologous end joining (NHEJ), microhomology-mediated end joining (MMEJ), or homology-directed repair (HDR) pathways. The HDR path of repair can be divided into two mechanistically distinct strategies: classic gene targeting using the Rad51 dependent homologous recombination pathway (HR) or via single-stranded template repair (SSTR) using a single stranded oligonucleotide (Porteus Annu. Rev. Pharmacol. Toxicol. 56, 163-190 (2016); Richardson et al. "CRISPR-Cas9 genome editing in human cells works via the Fanconi Anemia pathway" (2017)). Loss-of-function substitutions or INDELs can be created when a DSB is repaired by either NHEJ or MMEJ. On the other hand, when a homology donor is supplied, HDR enables the introduction of precise insertions of single nucleotides to large gene cassettes, deletions, or substitutions (Hsu et al. Cell 157, 1262-1278 (2014)).

In cell types traditionally refractory to editing, such as human pluripotent stem cells (hPSCs), selection markers are usually required in order to identify and purify a genome edited population or clone. However, leaving behind a selection marker in the genome can interfere with regional transcriptional regulation and would usually be incompatible with clinical translation. Although there exist methods which do not leave selectable markers (Gonzalez et al. Cell Stem Cell 15, 215-226 (2014); Mitzelfelt et al. Stem Cell Reports 0, 1-9 (2017)), these rely on persistent activity of sequence-specific nucleases near the editing site, which has the potential to disrupt the original edit (Paquet et al. Nature 533, 1-18 (2016)). To counteract this, previous methods of editing introduce silent mutations within the homology donor in order to protect the edited allele from persistent nuclease activity. Yet this introduction of silent mutations may result in several unintended consequences, such as splicing abnormalities (Yadegari et al. Blood 128, 2144-2152 (2016)), altered mRNA or protein structure (Duan et al. Human Molecular Genetics 12, 205-216 (2003); Kimchi-Sarfaty et al. Science 315, 525-8 (2007)), or even alterations in total protein levels due to codon usage bias. Therefore, the ideal genome editing method would be "scarless", one that does not leave remnants of the editing process neither in the form of a selection marker nor silent mutation, while still retaining the ability to generate HDR-mediated genome editing.

Although several scarless editing methods have been reported, all of them have limitations in terms of efficiency and/or versatility in hPSCs. The difficulty of scarless editing faces the following challenges: 1) The need to have a highly active nuclease to generate high frequencies of the desired edit, combined with 2) The need to prevent an INDEL on the untargeted allele; and 3) The need to prevent the HDR modified allele from being recut by the active nuclease and thus also accumulating an INDEL. A solution to the latter is to introduce synonymous changes to block re-cutting but these synonymous changes represent a small genetic scar as at least one and sometimes more changes are needed to prevent Cas9 from re-cutting as it has tolerance for small changes (Fu et al. Nat. Biotechnol. 31, 822-826 (2013)). An alternative approach is to screen hundreds-thousands of clones to find one with scarless bi-allelic edits, but with no structured method to guarantee that such a clone could exist. Simply improving the frequency of on-target editing does not solve the problem of identifying clones with scarless modifications and can sometimes even make the task more difficult.

Many of the previously reported methods rely on the target edit to overlap with the gRNA target such that after editing Cas9/gRNA re-cutting is prevented (Gonzalez et al., supra; Yu et al. Cell Stem Cell 16, 142-147 (2015); Liu et al. One-Step Biallelic and Scarless Correction of a β-Thalassemia Mutation in Patient-Specific iPSCs without Drug Selection. Mol Ther Nucleic Acids. 6, 57-67 (2017); Steyer et al. Stem Cell Reports 10, 642-654 (2018)). But this limits the range of target sites that can be edited without a scar. Paquet et al (2016) attempted to solve this limitation by a two-step editing process using ssODN and gRNA-Cas9, named CORRECT (Paquet et al., supra). They introduced a mutation to block re-cutting in addition to intended edit, then repaired the unwanted mutation by a $2^{nd}$ round of editing. This provided an elegant solution when length from the cut to edit site was short, but CORRECT was extremely inefficient or not efficient at all (0.0-0.3%) if the cut to target edit site was greater than 20 base pairs. Finally, the ssODN based methods are all limited to making small edits which precludes the possibility of scarless, large insertion editing, such as the introduction of a cDNA reporter (Yang et al. Nucleic Acids Res. 41, 9049-9061 (2013)). Finally, the CORRECT method remains cumbersome as it can require the analysis of hundreds of clones at both the first and second step to identify correct clones. Adding a selectable marker without removing it can decrease the number of clones needed to be analyzed but the marker leaves a clear scar in the genome. Therefore, an integrated marker needs to be removed for it to be a scarless system. The PiggyBac system is designed to remove the integrated marker using the PiggyBac transposase to excise the marker between transposon-specific inverted terminal repeat sequences leaving only a "TTAA" sequence, which is scarless as long as the TTAA was part of the endogenous target (Ye et al. Proc. Natl. Acad. Sci. 111, 9591-9596 (2014)). But there are a limited number of sites which the both a gRNA with a short cut to target distance and an adjacent TTAA sequence is present. Very recently, Kim and colleagues reported that MMEJ based editing enables scarless removal of integrated marker if there are microhomologies at both end of the marker (Kim et al. Nat. Commun. 9, (2018)). In their report they did not demonstrate true scarless editing as they introduced synonymous mutations during the process. Moreover, they used a system in which they integrated the reporter into genes that were expressed in pluripotent cells to decrease the frequency of identifying clones with random integrants. This feature also limits the scope of gene targets that the method can be applied to.

Therefore, more efficient and flexible methods of scarless editing, capable of modifying a genome at any location and enabling edits of larger size, are needed to allow genomes to be designed as desired.

SUMMARY

The invention relates to a method for scarless genome editing. In particular, the method provides scarless genome modification by using HDR steps to genetically modify cells and remove unwanted sequences. This method can be used for genome editing, including introducing mutations, deletions, or insertions at any position in the genome without leaving silent mutations, selection marker sequences, or other additional undesired sequences in the genome.

In one aspect, the invention includes a method of scarless editing of genomic DNA of a cell, the method comprising: a) performing a first Cas9-mediated homology directed repair (HDR) step comprising: i) introducing a first donor polynucleotide into the cell, wherein the first donor polynucleotide comprises a first left homology arm and a first right homology arm flanking a sequence comprising an intended edit to a target sequence to be modified in the genomic DNA of the cell and an expression cassette encoding at least one selection marker; and ii) introducing a first guide RNA and Cas9 into the cell, wherein the first guide RNA comprises a sequence complementary to the genomic target sequence to be modified in the genomic DNA of the cell, such that the Cas9 forms a first complex with the first guide RNA, said guide RNA directing the first complex to the genomic target sequence, wherein the first donor polynucleotide is integrated into the genomic DNA by Cas9-mediated HDR to produce a genetically modified cell; b) isolating the genetically modified cell based on positive selection for the at least one selection marker; c) performing a second Cas9-mediated homology directed repair (HDR) step comprising: i) introducing a second donor polynucleotide into the genetically modified cell, wherein the second donor polynucleotide comprises a second left homology arm and a second right homology arm flanking a sequence complementary to the target genomic sequence as modified by integration of the first donor polynucleotide into the genomic DNA by the Cas9-mediated HDR, except comprising a deletion of the expression cassette encoding the at least one selection marker; ii) introducing a second guide RNA and Cas9 nuclease into the cell, wherein the Cas9 forms a second complex with the second guide RNA, said second guide RNA directing the second complex to the modified target genomic sequence, wherein the Cas9 creates a double-stranded break in the modified genomic DNA, and the second donor polynucleotide is integrated into the genomic DNA by Cas9-mediated HDR, thereby removing the expression cassette encoding the at least one selection marker from the modified genomic DNA by Cas9-mediated HDR; and d) isolating a genetically modified cell comprising the intended edit based on negative selection for the at least one selection marker, wherein the expression cassette encoding the at least one selection marker is deleted.

In one embodiment, the sequence comprising the intended edit is positioned within or near the expression cassette encoding the selection marker.

In certain embodiments, the intended edit introduces a mutation into a gene in the genomic DNA of the cell, such as an insertion, deletion, or substitution. In other embodiments, the intended edit removes a mutation from a gene in the genomic DNA of the cell. In another embodiment, the intended edit results in inactivation of a gene in the genomic DNA of the cell.

Either one allele or two alleles may be modified in the genomic DNA. In certain embodiments, at least one selection marker is a fluorescent marker, wherein florescence intensity can be measured to determine if the genetically modified cell comprises a mono-allelic edit or a bi-allelic edit.

In certain embodiments, the doubled-stranded break is a non-gene destructive double stranded break. In certain embodiments, the double-stranded break does not affect the expression of said at least one selection marker.

In certain embodiments, one or more of the first donor polynucleotide, the second donor polynucleotide, the first guide RNA, the second guide RNA, and the Cas9 are provided by vector, such as a plasmid or viral vector. In another embodiment, the first guide RNA, and the Cas9 are provided by a single vector or multiple vectors. In another embodiment, the second donor polynucleotide, the second guide RNA, and the Cas9 are provided by a single vector or multiple vectors.

In certain embodiments, the cell to be genetically modified is from a eukaryotic, prokaryotic, or archaeon organism. Scarless genomic editing as described herein may be performed on the cell in vitro or in vivo. The cell may be from any type of animal, include vertebrates or invertebrates. For example, cells may be obtained from mammals, such as human or non-human mammals (e.g., non-human primates, laboratory animals, farm animals), or domestic, wild, or game birds. In another embodiment, the cell is from a cell line. The cell may be an immortalized cell or cancerous. In another embodiment, the cell is selected from the group consisting of a K562 cell, an embryonic stem cell, and an induced pluripotent stem cell.

In certain embodiments, at least one selection marker is selected from the group consisting of a cell surface marker, a drug resistance gene, a reporter gene, and a suicide gene. In another embodiment, the cell surface marker is selected from the group consisting of truncated CD8, NGFR, truncated CD19 (tCD19), CCR5, and an ABO antigen.

The genetically modified cell produced from the first HDR step may be isolated by positive selection using a binding agent that specifically binds to the selection marker.

In certain embodiments, the binding agent comprises an antibody, an antibody mimetic, or an aptamer that specifically binds to the selection marker.

In another embodiment, the binding agent comprises an antibody selected from the group consisting of a monoclonal antibody, a polyclonal antibody, a chimeric antibody, a nanobody, a recombinant fragment of an antibody, an Fab fragment, an Fab' fragment, an F(ab')$_2$ fragment, an F$_v$ fragment, and an scF$_v$ fragment.

For example, a cell genetically modified to express a surface marker may be isolated using a binding agent that specifically binds to that surface marker (e.g., an anti-tCD19 antibody to isolate cells carrying the tCD19 surface marker, an anti-CD8 antibody to isolate cells carrying the CD8 surface marker, or an anti-NGFR antibody to isolate cells carrying the NGFR surface marker).

In certain embodiments, the binding agent is immobilized on a solid support. Exemplary solid supports include a magnetic bead, a non-magnetic bead, a slide, a gel (e.g., agarose or acrylamide), nylon, a membrane, a glass plate, a microtiter plate well, or a metal, glass, or plastic surface.

Any cell separation technique may be used for isolating genetically modified cells, including, but not limited to, fluorescence activated cell sorting (FACS), magnetic-activated cell sorting (MACS), elutriation, immunopurification, or affinity chromatography.

In another embodiment, the expression cassette encoding at least one selection marker comprises a UbC promoter, a polynucleotide encoding mCherry, a polynucleotide encoding a T2A peptide, a polynucleotide encoding a truncated CD19 (tCD19), and a polyadenylation sequence.

In certain embodiments, the first donor polynucleotide further comprises at least one expression cassette encoding a short hairpin RNA (shRNA) that inhibits expression of a selection marker that is randomly integrated or episomal. For example, the first donor polynucleotide may comprise a pair of expression cassettes encoding the short hairpin RNA (shRNA), wherein the first expression cassette of the pair is located 5' to the first left homology arm and the second expression cassette of the pair is located 3' to the first right homology arm. Expression of the shRNA reduces selection of clones expressing a selection marker that is randomly integrated into the genome.

In another aspect, the invention includes a scarless genome editing system comprising: a) a first donor polynucleotide comprising a first left homology arm and a first right homology arm flanking a sequence comprising an intended edit to a target sequence to be modified in genomic DNA of a cell, and an expression cassette encoding at least one selection marker; b) a second donor polynucleotide comprising a second left homology arm and a second right homology arm flanking a sequence complementary to the sequence of the first donor polynucleotide except comprising a deletion of the expression cassette encoding the at least one selection marker; c) a Cas9 nuclease; d) a first guide RNA capable of forming a complex with the Cas9 nuclease and directing the complex to the target sequence; and e) a second guide RNA capable of forming a complex with the Cas9 nuclease and directing the complex to the target genomic sequence as modified by integration of the first donor polynucleotide into the genomic DNA by Cas9-mediated homology directed repair (HDR).

In another embodiment, the first donor polynucleotide comprises an expression cassette encoding at least one selection marker, wherein the expression cassette comprises the sequence of SEQ ID NO:1 or a sequence displaying at least about 80-100% sequence identity thereto, including any percent identity within these ranges, such as 81, 82, 83, 84, 85, 86, 87, 88, 89, 90, 91, 92, 93, 94, 95, 96, 97, 98, 99% sequence identity thereto, wherein the first donor polynucleotide is capable of integrating into the genomic DNA of the cell at a target site by Cas9-mediated HDR under conditions suitable for expression of the at least one selection marker, and a cell having the first donor polynucleotide integrated into the genomic DNA of the cell at the target site by Cas9-mediated HDR can be identified by positive selection for at least one selection marker encoded by the expression cassette.

In certain embodiments, one or more of the first donor polynucleotide, the second donor polynucleotide, the first guide RNA, the second guide RNA, and the Cas9 in the scarless genome editing system are provided by vector, such as a plasmid or viral vector. In another embodiment, the first guide RNA, and the Cas9 are provided by a single vector or multiple vectors. In another embodiment, the second donor polynucleotide, the second guide RNA, and the Cas9 are provided by a single vector or multiple vectors.

In another aspect, the invention includes a host cell comprising a scarless genome editing system described herein.

In another aspect, the invention includes a kit comprising a scarless genome editing system described herein. Such kits may comprise a first donor polynucleotide, a second donor polynucleotide, a first guide RNA, a second guide RNA, and a Cas9 nuclease. The kit may further comprise instructions for performing scarless editing of genomic DNA.

In certain embodiments, one or more of the first donor polynucleotide, the second donor polynucleotide, the first guide RNA, the second guide RNA, and the Cas9 in the kit are provided by vector, such as a plasmid or viral vector. In another embodiment, the first guide RNA, and the Cas9 are provided by a single vector or multiple vectors. In another embodiment, the second donor polynucleotide, the second guide RNA, and the Cas9 are provided by a single vector or multiple vectors.

In one embodiment, the first donor polynucleotide comprises a selection marker expression cassette comprising a sequence of SEQ ID NO:1 or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein a cell having the first donor polynucleotide integrated into the genomic DNA of the cell at a target site by Cas9-mediated HDR can be identified by positive selection for a selection marker encoded by the expression cassette.

These and other embodiments of the subject invention will readily occur to those of skill in the art in view of the disclosure herein.

BRIEF DESCRIPTION OF THE DRAWINGS

FIG. 1A shows the workflow of the scarless editing procedure through two step HR. FIG. 1B shows donor DNA constructs and guide RNAs for two step HR. In case of TBX1 editing, the intended mutation is G to A substitution at the 928 base pair (bp) of the TBX1 cDNA coding site (TBX1 c.928G>A). Arrows indicate the design of the primer for genotyping. FIG. 1C shows the timeline of editing. Total estimate time is 1.5 to 2 months, depending on the growth rate of the cells.

FIGS. 2A-2H show scarless 1 base substitution in human ES cells by 2 step HR. FIG. 2A shows flow cytometric analysis of transient (at day 2) and stable (at day 6) expression. FIG. 2B shows analysis before and after positive selection by magnetic-activated cell separation (MACS) by FACS based on tCD19 expression. CD19 positive cells were enriched from 2.1% to 67.8%. FIG. 2C shows fluorescent microscopy of single cell colonies after MACS positive selection. There were bright colonies (yellow arrowhead) and dim colonies (white arrowhead). Scale bar shows 200 μm. FIG. 2D shows genotyping of single cell clones after MACS positive selection using primers indicated in FIG. 1B. FIG. 2E shows copy number analysis of UbC promoter evaluated by droplet digital PCR. Data is shown as the mean±SD derived from three repeated measurements. FIG. 2F shows CD19 positive cell population of clone #2 and #13 before and after $2^{nd}$ HR and MACS negative selection. CD19 negative cells were enriched from 0.097% to 99.5% in #2 and from 0.044% to 94.7% in #13. FIG. 2G shows the genotypes of single cell clones determined by sequencing. FIG. 2H shows representative sequence data of mono- and bi-allelically edited clones (TBX1 reference sequence (SEQ ID NO:32) and c. 928G>A mutant (SEQ ID NO:33), as well as a consensus sequence (SEQ ID NO: 34)).

FIG. 3A shows schematic design of the donor DNAs and the guide RNAs for RUNX1 editing. Arrows indicate primers for genotyping. Size of PCR amplicon from each genotype is shown in right table. FIG. 3B shows genotyping of bright clones after 1st editing followed by MACS positive selection and single cell cloning by PCR. Clone #2 was used for the following procedure. FIG. 3C shows genotyping by PCR of a clone after $2^{nd}$ editing followed by MACS negative selection and single cell cloning. FIG. 3D shows representative image of RUNX1-mOrange iPSC sacs. Cells were observed 13 days after induction of differentiation. Scale bar=100 μm. FIG. 3E shows representative flow cytometric profile of the cells 14 days after induction of differentiation. The population A, which is CD34 positive, CD45 middle-double positive cells, expresses the highest intensity of mOrange among all populations.

FIG. 4A shows first editing without the shGFP expression cassette. FIG. 4B shows first editing with the shGFP expression cassette. All clones shown expressed bright GFP fluorescence. FIG. 4C shows second editing using clone #7. FIG. 4D shows a representative flow cytometric profile of the cells. Class I HLA type of ES H9 line is (A*02, A*03, B*35, B*44, C2*04 and Cw*07). iAM9 line are hiPSCs which has HLA-A*24, used as a positive control of natural HLA-A*24 expression. Cells were treated with 50 ng/mL of INFγ for 3 days prior to FCM analysis.

FIGS. 5A-5C show consideration of the real-use of MMEJ assisted scarless editing with gRNA-Cas9 system (KIM et al, Nature Commun.). FIG. 5A shows the difference in blocking of gRNA-Cas9 re-cutting by marker integration between standard and MMEJ assisted scarless strategy. In standard marker integration, if the marker is integrated at gRNA target sequence, edited genome is no longer cut by gRNA-Cas9. On the other hand, if marker is integrated with microhomology sequence at both end of selection marker, gRNA target will be retained unless microhomology is sufficiently short or mutations are introduced. FIG. 5B shows a possible design of microhomology when gRNA target does not overlap with intended edit. Cas9 is often tolerant of 2 nt of 5' mismatch (Far side from PAM), therefore 19 nt microhomology is practical upper-limit of the length in order to avoid re-cutting. Kim et al. demonstrated that the allele frequency of MMEJ based accurate excision with 19 nt homology was about one-third of that with 32 nt homology, meaning theoretical frequency of bi-allelic accurate excision in 19 nt homology is about 10 times lower that in 32 nt. Given frequency of accurate bi-allelic excision using 32 nt homology was 10%, that using 19 nt homology would be around 1%. FIG. 5C shows a possible design of microhomology when gRNA target overlaps with intended edit (indicated by "Z"). More than 32 nt homology can be produced, but 1 base mismatch typically does not prevent re-cutting by Cas9 (Fu et al., 2014 Nature Biotech). In case 1 base mismatch at intended edit efficiently block re-cutting and HR performance of the gRNA is high, standard 1 step scarless editing is available at high efficiency now.

FIGS. 6A-6D show target sites of guide RNAs for editing of TBX1 (FIG. 6A, SEQ ID NOS:35-36), RUNX1 (FIG. 6B, SEQ ID NOS:37-38), GFI1 (FIG. 6C, SEQ ID NOS:39-40), and B2M (FIG. 6D, SEQ ID NOS:41-42).

FIGS. 7A-7C show the second round of HR in TBX1 mono-allelically marker inserted clone #14. FIG. 7A shows sequence data of the marker free allele of clone #14 (SEQ ID NO:43). There is 1 base insertion of G at the position of cutting site by CRISPR/Cas9 in 1st editing process (SEQ ID NO:44). FIG. 7B shows genotypes of clones after $2^{nd}$ HR in clone #14 by sequence analysis. FIG. 7C shows the graphical scheme of HR with donor DNAs or the chromosome homolog.

FIG. 9A shows the schematic design of the donor DNAs and the guide RNAs for RUNX1 editing. Arrows indicate primers for genotyping. Size of PCR amplicon from each genotype is shown in right table. FIG. 9B shows genotyping of bright clones after 1st editing followed by MACS positive selection and single cell cloning by PCR. Copy number of UbC promoter was evaluated by ddPCR method. Clone #2 was used for the following procedure. FIG. 9C shows genotyping by PCR of a clone after 2nd editing followed by MACS negative selection and single cell cloning. Because 2nd donor vector contains same sequence (EGFP) in addition to homology arm, undesired editing event were contaminated (#1-3, 5) as depicted in (FIG. 9D).

FIG. 10A shows a schematic representation of primer design for detection of random integration. Primer sets 1 and 2 can detect random integration if a selection marker is integrated to genome with the sequence at outside of left and right homology arms respectively (derived from plasmid backbone). PCR results are shown in (FIG. 10B) for RUNX1 editing and in (FIG. 10C) for GFI1 editing.

FIG. 11A shows GG>AA mutation at 314th and 315th upstream from the ATG start codon. FIG. 11B shows flow cytometric analysis showing that the WT and GG>AA mutant of UbC promoter expressed almost the same intensity of GFP in K562 cells. FIG. 11C shows a schematic representation of primer design. FIG. 11D shows an agarose gel electrophoresis of PCR products digested with EcoRI-HF enzyme. DNA was stained with MidoriGreen dye. FIG. 11E shows a representative image of image analysis by Image J software. FIG. 11F shows quantification of fluorescence intensity (FI) in samples from regular PCR combined with EcoRI digestion. All samples from bright clones shows the same intensity between WT and GG>AA, meaning 2 copies of exogenous UbC promoter has been integrated, and FI of GG>AA were half of WT in samples from dim clones, meaning 1 copy of exogenous UbC promoter was integrated. FIG. 11G shows copy number analysis of UbC promoter using ddPCR based method. The result from ddPCR was consistent with that of a regular PCR-EcoRI digestion-based experiment. Data is shown as the mean±SD, N=3.

(FIG. 13A) Large insertion for such as introduction of a reporter gene which should be useful for optimization of differentiation in pluripotent stem cells or drug screening. (FIG. 13B) Large deletion for making disease models or knock out animals. (FIG. 13C) Large substitution for making knock-in animals including humanized models. (FIG. 13D) Editing in case that there is no good target site of site specific nucleases (SSNs) including zinc finger nuclease, near intended mutation site. Using this technique, almost all limitations to the editing site should be eliminated.

DETAILED DESCRIPTION

Figure 1A:
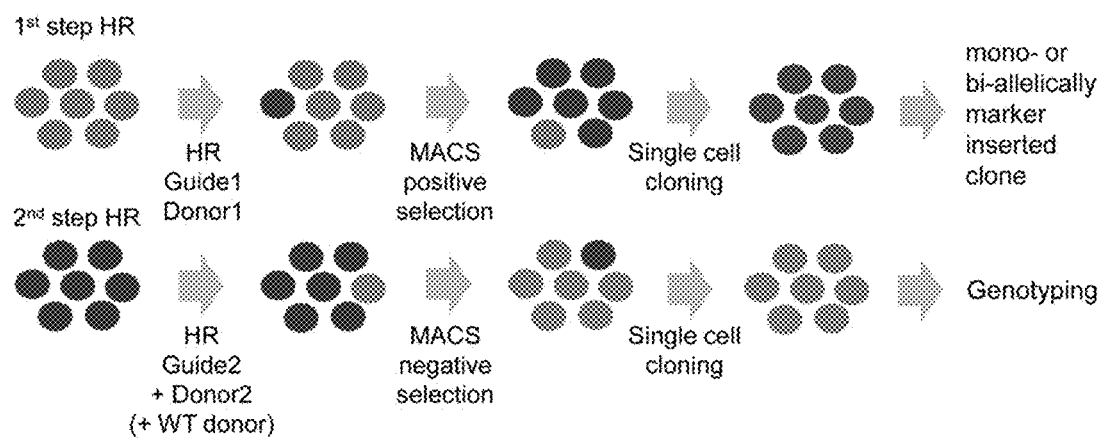
FIGS. 1A-1C show an overview of scarless editing.

The practice of the present invention will employ, unless otherwise indicated, conventional methods of genome editing, biochemistry, chemistry, immunology, molecular biology and recombinant DNA techniques within the skill of the art. Such techniques are explained fully in the literature. See, e.g., *Targeted Genome Editing Using Site-Specific Nucleases: ZFNs, TALENs, and the CRISPR/Cas9 System* (T. Yamamoto ed., Springer, 2015); *Genome Editing: The Next Step in Gene Therapy* (Advances in Experimental Medicine and Biology, T. Cathomen, M. Hirsch, and M. Porteus eds., Springer, 2016); Aachen Press *Genome Editing* (CreateSpace Independent Publishing Platform, 2015); *Handbook of Experimental Immunology*, Vols. I-IV (D. M. Weir and C. C. Blackwell eds., Blackwell Scientific Publications); A. L. Lehninger, *Biochemistry* (Worth Publishers, Inc., current addition); Sambrook, et al., *Molecular Cloning: A Laboratory Manual* (3rd Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

I. DEFINITIONS

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "a cell" includes a mixture of two or more cells, and the like.

The term "about," particularly in reference to a given quantity, is meant to encompass deviations of plus or minus five percent.

As used herein, a "cell" refers to any type of cell isolated from a prokaryotic, eukaryotic, or archaeon organism, including bacteria, archaea, fungi, protists, plants, and animals, including cells from tissues, organs, and biopsies, as well as recombinant cells, cells from cell lines cultured in vitro, and cellular fragments, cell components, or organelles comprising nucleic acids. The term also encompasses artificial cells, such as nanoparticles, liposomes, polymersomes, or microcapsules encapsulating nucleic acids. A cell may include a fixed cell or a live cell. The genome editing methods described herein can be performed, for example, on a sample comprising a single cell or a population of cells. The term also includes genetically modified cells.

The terms "polypeptide" and "protein" refer to a polymer of amino acid residues and are not limited to a minimum length. Thus, peptides, oligopeptides, dimers, multimers, and the like, are included within the definition. Both full length proteins and fragments thereof are encompassed by the definition. The terms also include postexpression modifications of the polypeptide, for example, glycosylation, acetylation, phosphorylation, hydroxylation, and the like. Furthermore, for purposes of the present invention, a "polypeptide" refers to a protein which includes modifications, such as deletions, additions and substitutions to the native sequence, so long as the protein maintains the desired activity. These modifications may be deliberate, as through site directed mutagenesis, or may be accidental, such as through mutations of hosts which produce the proteins or errors due to PCR amplification.

The term "Cas9" as used herein encompasses type II clustered regularly interspaced short palindromic repeats (CRISPR) system Cas9 endonucleases from any species, and also includes biologically active fragments, variants, analogs, and derivatives thereof that retain Cas9 endonuclease activity (i.e., catalyze site-directed cleavage of DNA to generate double-strand breaks). A Cas9 endonuclease binds to and cleaves DNA at a site comprising a sequence complementary to its bound guide RNA (gRNA).

A Cas9 polynucleotide, nucleic acid, oligonucleotide, protein, polypeptide, or peptide refers to a molecule derived from any source. The molecule need not be physically derived from an organism, but may be synthetically or recombinantly produced. Cas9 sequences from a number of bacterial species are well known in the art and listed in the National Center for Biotechnology Information (NCBI) database. See, for example, NCBI entries for Cas9 from: *Streptococcus pyogenes* (WP_002989955, WP_038434062, WP_011528583); *Campylobacter jejuni* (WP_022552435, YP_002344900), *Campylobacter coli* (WP_060786116); *Campylobacter fetus* (WP_059434633); *Corynebacterium* ulcerans (NC_015683, NC_017317); *Corynebacterium diphtheria* (NC_016782, NC_016786); *Enterococcus faecalis* (WP_033919308); *Spiroplasma syrphidicola* (NC_021284); *Prevotella intermedia* (NC_017861); *Spiroplasma taiwanense* (NC_021846); *Streptococcus iniae* (NC_021314); *Belliella baltica* (NC_018010); *Psychrojlexus torquisI* (NC_018721); *Streptococcus thermophilus* (YP_820832), *Streptococcus mutans* (WP_061046374, WP 024786433); *Listeria innocua* (NP_472073); *Listeria monocytogenes* (WP_061665472); *Legionella pneumophila* (WP_062726656); *Staphylococcus aureus* (WP_001573634); *Francisella tularensis* (WP_032729892, WP_014548420), *Enterococcus faecalis* (WP_033919308); *Lactobacillus rhamnosus* (WP_048482595, WP_032965177); and *Neisseria meningitidis* (WP_061704949, YP_002342100); all of which sequences (as entered by the date of filing of this application) are herein incorporated by reference. Any of these sequences or a variant thereof comprising a sequence having at least about 70-100% sequence identity thereto, including any percent identity within this range, such as 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity thereto, can be used for scarless genome editing, as described herein, wherein the variant retains biological activity, such as Cas9 site-directed endonuclease activity. See also Fonfara et al. (2014) *Nucleic Acids Res.* 42(4):2577-90; Kapitonov et al. (2015) *J. Bacteriol.* 198(5):797-807, Shmakov et al. (2015) *Mol. Cell.* 60(3):385-397, and Chylinski et al. (2014) *Nucleic Acids Res.* 42(10):6091-6105); for sequence comparisons and a discussion of genetic diversity and phylogenetic analysis of Cas9.

By "derivative" is intended any suitable modification of the native polypeptide of interest, of a fragment of the native polypeptide, or of their respective analogs, such as glycosylation, phosphorylation, polymer conjugation (such as with polyethylene glycol), or other addition of foreign moieties, as long as the desired biological activity of the native polypeptide is retained. Methods for making polypeptide fragments, analogs, and derivatives are generally available in the art.

By "fragment" is intended a molecule consisting of only a part of the intact full-length sequence and structure. The fragment can include a C-terminal deletion an N-terminal deletion, and/or an internal deletion of the polypeptide. Active fragments of a particular protein or polypeptide will generally include at least about 5-10 contiguous amino acid residues of the full length molecule, preferably at least about 15-25 contiguous amino acid residues of the full length molecule, and most preferably at least about 20-50 or more contiguous amino acid residues of the full length molecule, or any integer between 5 amino acids and the full length sequence, provided that the fragment in question retains biological activity, such as Cas9 site-directed endonuclease activity.

"Substantially purified" generally refers to isolation of a substance (compound, polynucleotide, nucleic acid, protein, polypeptide, polypeptide composition) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

As used herein, the phrase "heterogeneous population of cells" refers to a mixture of at least two types of cells, one type being the cells of interest (e.g., having a genomic modification of interest). The heterogeneous population of cells may be derived from any organism.

The terms "isolating" and "isolation," as used herein in the context of selecting a cell or population of cells having a genomic modification of interest, refer to separating a cell or population of cells having the genomic modification of interest from a heterogeneous population of cells, such as by positive or negative selection.

The term "selection marker" refers to a marker which can be used for enrichment of a cell population from a heterogeneous population of cells, either by positive selection (selecting cells expressing the marker) or by negative selection (excluding cells expressing the marker).

The term "binding agent" refers to any agent that specifically binds to a selection marker. Examples of binding agents include, without limitation, antibodies, antibody fragments, antibody mimetics, and aptamers that specifically bind to a selection marker.

The phrase "specifically (or selectively) binds" when referring to a binding agent, refers to a binding reaction that is determinative of the presence of a cell carrying a particular selection marker in a heterogeneous population of cells and other biologics. Thus, under designated conditions, the binding agent binds to a particular selection marker on a cell at least two times the background and does not substantially bind in a significant amount to other cells not carrying the selection marker present in the sample. Specific binding to a cell carrying the selection marker under such conditions may require a binding agent (e.g., antibody, antibody mimetic, or aptamer) that is selected for its specificity for a particular selection marker. Typically, specific or selective binding between a binding agent and a selection marker will be at least twice background signal or noise and more typically more than 10 to 100 times background.

The term "antibody" encompasses polyclonal and monoclonal antibody preparations, as well as preparations including hybrid antibodies, altered antibodies, chimeric antibodies and, humanized antibodies, as well as: hybrid (chimeric) antibody molecules (see, for example, Winter et al. (1991) *Nature* 349:293-299; and U.S. Pat. No. 4,816,567); F(ab')$_2$ and F(ab) fragments; F$_v$ molecules (noncovalent heterodimers, see, for example, Inbar et al. (1972) *Proc Natl Acad Sci USA* 69:2659-2662; and Ehrlich et al. (1980) *Biochem* 19:4091-4096); single-chain Fv molecules (sFv) (see, e.g., Huston et al. (1988) *Proc Natl Acad Sci USA* 85:5879-5883); nanobodies or single-domain antibodies (sdAb) (see, e.g., Wang et al. (2016) *Int J Nanomedicine* 11:3287-3303, Vincke et al. (2012) *Methods Mol Biol* 911:15-26; dimeric and trimeric antibody fragment constructs; minibodies (see, e.g., Pack et al. (1992) *Biochem* 31:1579-1584; Cumber et al. (1992) *J Immunology* 149B:120-126); humanized antibody molecules (see, e.g., Riechmann et al. (1988) *Nature* 332:323-327; Verhoeyan et al. (1988) *Science* 239:1534-1536; and U.K. Patent Publication No. GB 2,276,169, published Sep. 21, 1994); and, any functional fragments obtained from such molecules, wherein such fragments retain specific-binding properties of the parent antibody molecule.

As used herein, a "solid support" refers to a solid surface such as a magnetic bead, latex bead, microtiter plate well, glass plate, nylon, agarose, acrylamide, and the like.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. Thus, these terms include, for example, 3'-deoxy-2', 5'-DNA, oligodeoxyribonucleotide N3' P5' phosphoramidates, 2'-O-alkyl-substituted RNA, double- and single-stranded DNA, as well as double- and single-stranded RNA, microRNA, DNA:RNA hybrids, and hybrids between PNAs and DNA or RNA, and also include known types of modifications, for example, labels which are known in the art, methylation, "caps," substitution of one or more of the naturally occurring nucleotides with an analog (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. The term also includes locked nucleic acids (e.g., comprising a ribonucleotide that has a methylene bridge between the 2'-oxygen atom and the 4'-carbon atom). See, for example, Kurreck et al. (2002) Nucleic Acids Res. 30: 1911-1918; Elayadi et al. (2001) Curr. Opinion Invest. Drugs 2: 558-561; Orum et al. (2001) Curr. Opinion Mol. Ther. 3: 239-243; Koshkin et al. (1998) Tetrahedron 54: 3607-3630; Obika et al. (1998) Tetrahedron Lett. 39: 5401-5404.

The terms "hybridize" and "hybridization" refer to the formation of complexes between nucleotide sequences which are sufficiently complementary to form complexes via Watson-Crick base pairing.

The term "homologous region" refers to a region of a nucleic acid with homology to another nucleic acid region. Thus, whether a "homologous region" is present in a nucleic acid molecule is determined with reference to another nucleic acid region in the same or a different molecule. Further, since a nucleic acid is often double-stranded, the term "homologous, region," as used herein, refers to the ability of nucleic acid molecules to hybridize to each other. For example, a single-stranded nucleic acid molecule can have two homologous regions which are capable of hybridizing to each other. Thus, the term "homologous region" includes nucleic acid segments with complementary sequences. Homologous regions may vary in length, but will typically be between 4 and 500 nucleotides (e.g., from about 4 to about 40, from about 40 to about 80, from about 80 to about 120, from about 120 to about 160, from about 160 to about 200, from about 200 to about 240, from about 240 to about 280, from about 280 to about 320, from about 320 to about 360, from about 360 to about 400, from about 400 to about 440, etc.).

As used herein, the terms "complementary" or "complementarity" refers to polynucleotides that are able to form base pairs with one another. Base pairs are typically formed by hydrogen bonds between nucleotide units in an antiparallel orientation between polynucleotide strands. Complementary polynucleotide strands can base pair in a Watson-Crick manner (e.g., A to T, A to U, C to G), or in any other manner that allows for the formation of duplexes. As persons skilled in the art are aware, when using RNA as opposed to DNA, uracil (U) rather than thymine (T) is the base that is considered to be complementary to adenosine. However, when a uracil is denoted in the context of the present invention, the ability to substitute a thymine is implied, unless otherwise stated. "Complementarity" may exist between two RNA strands, two DNA strands, or between an RNA strand and a DNA strand. It is generally understood that two or more polynucleotides may be "complementary" and able to form a duplex despite having less than perfect or less than 100% complementarity. Two sequences are "perfectly complementary" or "100% complementary" if at least a contiguous portion of each polynucleotide sequence, comprising a region of complementarity, perfectly base pairs with the other polynucleotide without any mismatches or interruptions within such region. Two or more sequences are considered "perfectly complementary" or "100% complementary" even if either or both polynucleotides contain additional non-complementary sequences as long as the contiguous region of complementarity within each polynucleotide is able to perfectly hybridize with the other. "Less than perfect" complementarity refers to situations where less than all of the contiguous nucleotides within such region of complementarity are able to base pair with each other. Determining the percentage of complementarity between two polynucleotide sequences is a matter of ordinary skill in the art. For purposes of Cas9 targeting, a gRNA may comprise a sequence "complementary" to a target sequence (e.g., major or minor allele), capable of sufficient base-pairing to form a duplex (i.e., the gRNA hybridizes with the target sequence). Additionally, the gRNA may comprise a sequence complementary to a PAM sequence, wherein the gRNA also hybridizes with the PAM sequence in a target DNA.

A "target site" or "target sequence" is the nucleic acid sequence recognized (i.e., sufficiently complementary for hybridization) by a guide RNA (gRNA) or a homology arm of a donor polynucleotide. The target site may be allele-specific (e.g., a major or minor allele).

The term "donor polynucleotide" refers to a polynucleotide that provides a sequence of an intended edit to be integrated into the genome at a target locus by HDR.

By "homology arm" is meant a portion of a donor polynucleotide that is responsible for targeting the donor polynucleotide to the genomic sequence to be edited in a cell. The donor polynucleotide typically comprises a 5' homology arm that hybridizes to a 5' genomic target sequence and a 3' homology arm that hybridizes to a 3' genomic target sequence flanking a nucleotide sequence comprising the intended edit to the genomic DNA. The homology arms are referred to herein as 5' and 3' (i.e., upstream and downstream) homology arms, which relates to the relative position of the homology arms to the nucleotide sequence comprising the intended edit within the donor polynucleotide. The 5' and 3' homology arms hybridize to regions within the target locus in the genomic DNA to be modified, which are referred to herein as the "5' target sequence" and "3' target sequence," respectively. The nucleotide sequence comprising the intended edit is integrated into the genomic DNA by HDR at the genomic target locus recognized (i.e., sufficiently complementary for hybridization) by the 5' and 3' homology arms.

"Administering" a nucleic acid, such as a donor polynucleotide, guide RNA, or Cas9 expression system to a cell comprises transducing, transfecting, electroporating, translocating, fusing, phagocytosing, shooting or ballistic methods, etc., i.e., any means by which a nucleic acid can be transported across a cell membrane.

By "selectively binds" with reference to a guide RNA is meant that the guide RNA binds preferentially to a target sequence of interest or binds with greater affinity to the target sequence than to other genomic sequences. For example, a gRNA will bind to a substantially complementary sequence and not to unrelated sequences. A gRNA that "selectively binds" to a particular allele, such as a particular mutant allele (e.g., allele comprising a substitution, insertion, or deletion), denotes a gRNA that binds preferentially to the particular target allele, but to a lesser extent to a wild-type allele or other sequences. A gRNA that selectively binds to a particular target DNA sequence will selectively direct binding of Cas9 to a substantially complementary sequence at the target site and not to unrelated sequences.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, semiconductor nanoparticles, dyes, metal ions, metal sols, ligands (e.g., biotin, streptavidin or haptens) and the like. The term "fluorescer" refers to a substance or a portion thereof which is capable of exhibiting fluorescence in the detectable range. Particular examples of labels which may be used in the practice of the invention include, but are not limited to, SYBR green, SYBR gold, a CAL Fluor dye such as CAL Fluor Gold 540, CAL Fluor Orange 560, CAL Fluor Red 590, CAL Fluor Red 610, and CAL Fluor Red 635, a Quasar dye such as Quasar 570, Quasar 670, and Quasar 705, an Alexa Fluor such as Alexa Fluor 350, Alexa Fluor 488, Alexa Fluor 546, Alexa Fluor 555, Alexa Fluor 594, Alexa Fluor 647, and Alexa Fluor 784, a cyanine dye such as Cy 3, Cy3.5, Cy5, Cy5.5, and Cy7, fluorescein, 2', 4', 5', 7'-tetrachloro-4-7-dichlorofluorescein (TET), carboxyfluorescein (FAM), 6-carboxy-4', 5'-dichloro-2',7'-dimethoxyfluorescein (JOE), hexachlorofluorescein (HEX), rhodamine, carboxy-X-rhodamine (ROX), tetramethyl rhodamine (TAMRA), FITC, dansyl, umbelliferone, dimethyl acridinium ester (DMAE), Texas red, luminol, NADPH, horseradish peroxidase (HRP), and α-β-galactosidase.

"Homology" refers to the percent identity between two polynucleotide or two polypeptide molecules. Two nucleic acid, or two polypeptide sequences are "substantially homologous" to each other when the sequences exhibit at least about 50% sequence identity, preferably at least about 75% sequence identity, more preferably at least about 80% 85% sequence identity, more preferably at least about 90% sequence identity, and most preferably at least about 95% 98% sequence identity over a defined length of the molecules. As used herein, substantially homologous also refers to sequences showing complete identity to the specified sequence.

In general, "identity" refers to an exact nucleotide to nucleotide or amino acid to amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in Atlas of Protein Sequence and Structure M. O. Dayhoff ed., 5 Suppl. 3:353 358, National biomedical Research Foundation, Washington, D.C., which adapts the local homology algorithm of Smith and Waterman Advances in Appl. Math. 2:482 489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE;

Databases=non-redundant, GenBank+EMBL+DDBJ+ PDB+GenBank CDS translations+Swiss protein+Spupdate+ PIR. Details of these programs are readily available.

Alternatively, homology can be determined by hybridization of polynucleotides under conditions which form stable duplexes between homologous regions, followed by digestion with single stranded specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Recombinant host cells", "host cells," "cells", "cell lines," "cell cultures," and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence can be determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Expression cassette" or "expression construct" refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a donor polynucleotide, plasmid, or viral vector construct. In addition to the components of the expression cassette, the construct may also include, one or more selectable markers, a signal which allows the construct to exist as single stranded DNA (e.g., a M13 origin of replication), at least one multiple cloning site, and a "mammalian" origin of replication (e.g., a SV40 or adenovirus origin of replication).

"Purified polynucleotide" refers to a polynucleotide of interest or fragment thereof which is essentially free, e.g., contains less than about 50%, preferably less than about 70%, and more preferably less than about at least 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) Virology, 52:456, Sambrook et al. (2001) Molecular Cloning, a laboratory manual, 3rd edition, Cold Spring Harbor Laboratories, New York, Davis et al. (1995) Basic Methods in Molecular Biology, 2nd edition, McGraw-Hill, and Chu et al. (1981) Gene 13:197. Such techniques can be used to introduce one or more exogenous DNA moieties into suitable host cells. The term refers to both stable and transient uptake of the genetic material, and includes uptake of peptide- or antibody-linked DNAs.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as plasmid and viral vectors.

The terms "variant," "analog" and "mutein" refer to biologically active derivatives of the reference molecule that retain desired activity, such as site-directed Cas9 endonuclease activity. In general, the terms "variant" and "analog" refer to compounds having a native polypeptide sequence and structure with one or more amino acid additions, substitutions (generally conservative in nature) and/or deletions, relative to the native molecule, so long as the modifications do not destroy biological activity and which are "substantially homologous" to the reference molecule as defined below. In general, the amino acid sequences of such analogs will have a high degree of sequence homology to the reference sequence, e.g., amino acid sequence homology of more than 50%, generally more than 60%-70%, even more particularly 80%-85% or more, such as at least 90%-95% or more, when the two sequences are aligned. Often, the analogs will include the same number of amino acids but will include substitutions, as explained herein. The term "mutein" further includes polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and 5,977,301; Nguyen et al., Chem. Biol. (2000) 7:463-473; and Simon et al., Proc. Natl. Acad. Sci. USA (1992) 89:9367-9371 for descriptions of peptoids). Methods for making polypeptide analogs and muteins are known in the art and are described further below.

As explained above, analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, and tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that can tolerate change by reference to Hopp/Woods and Kyte-Doolittle plots, well known in the art.

"Gene transfer" or "gene delivery" refers to methods or systems for reliably inserting DNA or RNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, adenoviruses, retroviruses, alphaviruses, pox viruses, and vaccinia viruses.

The term "derived from" is used herein to identify the original source of a molecule but is not meant to limit the method by which the molecule is made which can be, for example, by chemical synthesis or recombinant means.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

The term "subject" includes both vertebrates and invertebrates, including, without limitation, mammals, including human and non-human mammals such as non-human primates, including chimpanzees and other apes and monkey species; laboratory animals such as mice, rats, rabbits, hamsters, guinea pigs, and chinchillas; domestic animals such as dogs and cats; farm animals such as sheep, goats, pigs, horses and cows; and birds such as domestic, wild and game birds, including chickens, turkeys and other gallinaceous birds, ducks, geese, and the like. In some cases, the methods of the invention find use in experimental animals, in veterinary application, and in the development of animal models for disease, including, but not limited to, rodents including mice, rats, and hamsters; primates, and transgenic animals.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the development of a method of scarless genome editing using two-step HDR repair to genetically modify cells and remove unwanted sequences. This method can be used in genome editing to introduce mutations, deletions, or insertions at any position in a genome without leaving silent mutations, selection marker sequences, or other additional undesired sequences in the genome. Further, there are almost no limitations on the choice of the editing site. This method can be used for not only small edits but also large edits of several thousand bases. Major advantages of this genome editing method include its extremely high efficiency and flexibility in various kind of cells. The inventors have successfully demonstrated the use of this method for genome editing of human ES/iPS cells (Example 1). The high efficiency of this method allows desired clones to be identified typically with no need to screen more than 10 colonies. In addition, this method is readily adaptable to allow multiple gene editing (see Example 1).

In order to further an understanding of the invention, a more detailed discussion is provided below regarding scarless genome editing using two-step HDR repair.

A. Scarless Genome Editing by Two-Step HDR Repair

As explained above, the methods of the present invention utilize two HDR repair steps to achieve scarless genome editing using a Cas9 nuclease. In the first HDR step, a donor polynucleotide containing a sequence comprising the intended edit to the genome is used to modify a target genomic sequence in a cell, wherein the donor polynucleotide is integrated into the genome at a target locus by site-directed homologous recombination. The donor polynucleotide can be used, for example, to introduce an intended edit into the genome for the purpose of repairing, modifying, replacing, deleting, attenuating or inactivating a target gene. The inclusion of a selection marker expression cassette in the donor polynucleotide allows genetically modified cells produced by the first HDR step to be isolated by positive selection. In the second HDR step, a second donor polynucleotide is used to delete the selection marker expression cassette from the genetically modified cells produced in the first HDR step. The second donor polynucleotide comprises a sequence complementary to the target genomic sequence as modified by integration of the first donor polynucleotide into the genomic DNA in the first HDR step, except comprising a deletion of the selection marker expression cassette. Hence, integration of the second donor polynucleotide at the target genomic locus removes the expression cassette. Genetically modified cells having the selection marker cassette removed can be isolated based on negative selection.

In the donor polynucleotide used in the first HDR step, the sequence comprising the intended edit is flanked by a pair of homology arms responsible for targeting the donor polynucleotide to the target locus to be edited in a cell. The donor polynucleotide typically comprises a 5' homology arm that hybridizes to a 5' genomic target sequence and a 3' homology arm that hybridizes to a 3' genomic target sequence. The homology arms are referred to herein as 5' and 3' (i.e., upstream and downstream) homology arms, which relates to the relative position of the homology arms to the nucleotide sequence comprising the intended edit within the donor polynucleotide. The 5' and 3' homology arms hybridize to regions within the target locus in the genomic DNA to be modified, which are referred to herein as the "5' target sequence" and "3' target sequence," respectively. The donor polynucleotide used in the second HDR step to remove the selection marker expression cassette similarly has a 5' homology arm and a 3' homology arm flanking a sequence complementary to the integrated donor polynucleotide from the first HDR step.

The homology arm must be sufficiently complementary for hybridization to the target sequence to mediate homologous recombination between the donor polynucleotide and genomic DNA at the target locus. For example, a homology arm may comprise a nucleotide sequence having at least about 80-100% sequence identity to the corresponding genomic target sequence, including any percent identity within this range, such as at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity thereto, wherein the nucleotide sequence comprising the intended edit is integrated into the genomic DNA by HDR at the genomic target locus recognized (i.e., sufficiently complementary for hybridization) by the 5' and 3' homology arms.

In certain embodiments, the corresponding homologous nucleotide sequences in the genomic target sequence (i.e., the "5' target sequence" and "3' target sequence") flank a specific site for cleavage and/or a specific site for introducing the intended edit. The distance between the specific cleavage site and the homologous nucleotide sequences (e.g., each homology arm) can be several hundred nucleotides. In some embodiments, the distance between a homology arm and the cleavage site is 200 nucleotides or less (e.g., 0, 10, 20, 30, 50, 75, 100, 125, 150, 175, and 200 nucleotides). In most cases, a smaller distance may give rise to a higher gene targeting rate. In a preferred embodiment, the donor polynucleotide is substantially identical to the target genomic sequence, across its entire length except for the sequence changes to be introduced to a portion of the genome that encompasses both the specific cleavage site and the portions of the genomic target sequence to be altered.

A homology arm can be of any length, e.g. 10 nucleotides or more, 50 nucleotides or more, 100 nucleotides or more, 250 nucleotides or more, 300 nucleotides or more, 350 nucleotides or more, 400 nucleotides or more, 450 nucleotides or more, 500 nucleotides or more, 1000 nucleotides (1 kb) or more, 5000 nucleotides (5 kb) or more, 10000 nucleotides (10 kb) or more, etc. In some instances, the 5' and 3' homology arms are substantially equal in length to one another, e.g. one may be 30% shorter or less than the other homology arm, 20% shorter or less than the other homology arm, 10% shorter or less than the other homology arm, 5% shorter or less than the other homology arm, 2% shorter or less than the other homology arm, or only a few nucleotides less than the other homology arm. In other instances, the 5' and 3' homology arms are substantially different in length from one another, e.g. one may be 40% shorter or more, 50% shorter or more, sometimes 60% shorter or more, 70% shorter or more, 80% shorter or more, 90% shorter or more, or 95% shorter or more than the other homology arm.

In certain embodiments, cells containing modified genomes produced in the first HDR step are identified in vitro or in vivo by including a selection marker expression cassette in the donor polynucleotide. Selection markers confer an identifiable change to the cell permitting positive selection of genetically modified cells having the donor polynucleotide integrated into the genome. For example, fluorescent or bioluminescent markers (e.g., green fluorescent protein (GFP), enhanced green fluorescent protein (EGFP), Dronpa, mCherry, mOrange, mPlum, Venus, YPet, phycoerythrin, or luciferase), cell surface markers (e.g., truncated CD8, NGFR, or CD19), expression of a reporter gene (e.g., GFP, dsRed, GUS, lacZ, CAT), or drug selection markers such as genes that confer resistance to neomycin, puromycin, hygromycin, DHFR, GPT, zeocin, or histidinol may be used to identify cells. Alternatively, enzymes such as herpes simplex virus thymidine kinase (tk) or chloramphenicol acetyltransferase (CAT) may be employed. Any selectable marker may be used as long as it is capable of being expressed after integration of the donor polynucleotide in the first HDR step to allow identification of genetically modified cells. Further examples of selectable markers are well known to one of skill in the art.

In certain embodiments, the selection marker expression cassette encodes two or more selection markers. Selection markers may be used in combination, for example, a cell surface marker may be used with a fluorescent marker, or a drug resistance gene may be used with a suicide gene. In certain embodiments, the donor polynucleotide is provided by a multicistronic vector to allow expression of multiple selection markers in combination. The multicistronic vector may include an IRES or viral 2A peptide to allow expression of more than one selection marker from a single vector as described further below.

Genome editing as described herein may result in either one allele or two alleles being modified in the genomic DNA of a cell. In certain embodiments, at least one of the selection markers used for positive selection is a fluorescent marker, wherein florescence intensity can be measured to determine if the genetically modified cell comprises a mono-allelic edit or a bi-allelic edit.

An exemplary expression cassette encoding a fluorescent mCherry marker and a truncated CD19 (tCD19) cell surface marker is shown in Example 1. The selection marker expression cassette comprises a UbC promoter operably linked to a polynucleotide encoding mCherry, a polynucleotide encoding a T2A peptide, a polynucleotide encoding a truncated CD19 (tCD19), and a polyadenylation sequence.

In certain embodiments, a negative selection marker is used to identify cells not having the selection marker expression cassette (i.e. having sequences encoding positive selection markers deleted). For example, a suicide marker may be included as a negative selection marker in the selection marker expression cassette to facilitate negative selection of cells after the second HDR step. Suicide genes can be used to selectively kill cells by inducing apoptosis or converting a nontoxic drug to a toxic compound in genetically modified cells. Examples include suicide genes encoding thymidine kinases, cytosine deaminases, intracellular antibodies, telomeraseses, caspases, and DNases. In certain embodiments, a suicide gene is used in combination with one or more other selection markers, such as those described above for use in positive selection of cells. The suicide gene may be removed in the second HDR step to achieve scarless editing. Alternatively, the suicide gene may be retained in the genetically modified cells after the second HDR step to improve their safety by allowing their destruction at will. See, e.g., Jones et al. (2014) Front. Pharmacol. 5:254, Mitsui et al. (2017) Mol. Ther. Methods Clin. Dev. 5:51-58, Greco et al. (2015) Front. Pharmacol. 6:95; herein incorporated by reference.

Alternatively or additionally, cells can be tested for the absence of selection marker sequences and other undesired sequences in genetically modified cells after the second HDR step using conventional methods, such as polymerase chain reaction (PCR), fluorescent in situ hybridization (FISH), gene array, sequencing, or hybridization techniques (e.g., Southern blot).

Genome editing may be performed on a single cell or a population of cells of interest and can be performed on any type of cell, including any cell from a prokaryotic, eukaryotic, or archaeon organism, including bacteria, archaea, fungi, protists, plants, and animals. Cells from tissues, organs, and biopsies, as well as recombinant cells, genetically modified cells, cells from cell lines cultured in vitro, and artificial cells (e.g., nanoparticles, liposomes, polymersomes, or microcapsules encapsulating nucleic acids) may all be used in the practice of the invention. The methods of the invention are also applicable to editing of nucleic acids in cellular fragments, cell components, or organelles comprising nucleic acids (e.g., mitochondria in animal and plant cells, plastids (e.g., chloroplasts) in plant cells and algae). Cells may be cultured or expanded prior to performing scarless genome editing as described herein, or at any time during the process, such as between performing the first and second HDR steps, or after the second HDR step.

Any type II CRISPR system Cas9 endonuclease from any species, or a biologically active fragment, variant, analog, or derivatives thereof that retains Cas9 endonuclease activity (i.e., catalyze site-directed cleavage of DNA to generate double-strand breaks) may be used to perform the HDR steps. The Cas9 need not be physically derived from an organism, but may be synthetically or recombinantly produced. Cas9 sequences from a number of bacterial species are well known in the art and listed in the National Center for Biotechnology Information (NCBI) database. See, for example, NCBI entries for Cas9 from: *Streptococcus pyogenes* (WP_002989955, WP_038434062, WP_011528583); *Campylobacter jejuni* (WP_022552435, YP_002344900), *Campylobacter coli* (WP_060786116); *Campylobacter fetus* (WP_059434633); *Corynebacterium ulcerans* (NC_015683, NC_017317); *Corynebacterium diphtheria* (NC_016782, NC_016786); *Enterococcus faecalis* (WP_033919308); *Spiroplasma syrphidicola* (NC_021284); *Prevotella intermedia* (NC_017861); *Spiroplasma taiwanense* (NC_021846); *Streptococcus iniae* (NC_021314); *Belliella baltica* (NC_018010); *Psychrojlexus torquisI* (NC_018721); *Streptococcus thermophilus* (YP_820832), *Streptococcus mutans* (WP_061046374, WP_024786433); *Listeria innocua* (NP_472073); *Listeria monocytogenes* (WP_061665472); *Legionella pneumophila* (WP_062726656); *Staphylococcus aureus* (WP_001573634); *Francisella tularensis* (WP_032729892, WP_014548420), *Enterococcus faecalis* (WP_033919308); *Lactobacillus rhamnosus* (WP_048482595, WP_032965177); and *Neisseria meningitidis* (WP_061704949, YP_002342100); all of which sequences (as entered by the date of filing of this application) are herein incorporated by reference. Any of these sequences or a variant thereof comprising a sequence having at least about 70-100% sequence identity thereto, including any percent identity within this range, such as 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity thereto, can be used for scarless genome editing, as described herein. See also Fonfara et al. (2014) Nucleic Acids Res. 42(4):2577-90; Kapitonov et al. (2015) J. Bacteriol. 198(5):797-807, Shmakov et al. (2015) Mol. Cell. 60(3):385-397, and Chylinski et al. (2014) Nucleic Acids Res. 42(10):6091-6105); for sequence comparisons and a discussion of genetic diversity and phylogenetic analysis of Cas9.

The CRISPR-Cas system naturally occurs in bacteria and archaea where it plays a role in RNA-mediated adaptive immunity against foreign DNA. The bacterial type II CRISPR system uses the endonuclease, Cas9, which forms a complex with a guide RNA (gRNA) that specifically hybridizes to a complementary genomic target sequence, where the Cas9 endonuclease catalyzes cleavage to produce a double-stranded break. Targeting of Cas9 further relies on the presence of a 5' protospacer-adjacent motif (PAM) in the DNA at or near the gRNA-binding site.

Cas9 can be targeted to a particular genomic sequence (i.e., genomic target sequence to be modified) by altering its guide RNA sequence. A target-specific guide RNA comprises a nucleotide sequence that is complementary to a genomic target sequence, and thereby mediates binding of the Cas9-gRNA complex by hybridization at the target site. For example, the gRNA can be designed with a sequence complementary to the sequence of a minor allele to target the Cas9-gRNA complex to the site of a mutation. The mutation may comprise an insertion, a deletion, or a substitution. For example, the mutation may include a single nucleotide variation, gene fusion, translocation, inversion, duplication, frameshift, missense, nonsense, or other mutation associated with a phenotype or disease of interest. The targeted minor allele may be a common genetic variant or a rare genetic variant. In certain embodiments, the gRNA is designed to selectively bind to a minor allele with single base-pair discrimination, for example, to allow binding of the Cas9-gRNA complex to a single nucleotide polymorphism (SNP). In particular, the gRNA may be designed to target disease-relevant mutations of interest for the purpose of genome editing to remove the mutation from a gene. Alternatively, the gRNA can be designed with a sequence complementary to the sequence of a major or wild-type allele to target the Cas9-gRNA complex to the allele for the purpose of genome editing to introduces a mutation into a gene in the genomic DNA of the cell, such as an insertion, deletion, or substitution. Such genetically modified cells can be used, for example, to produce disease models for drug screening.

The genomic target site will typically comprise a nucleotide sequence that is complementary to the gRNA, and may further comprise a protospacer adjacent motif (PAM). In certain embodiments, the target site comprises 20-30 base pairs in addition to a 3 base pair PAM. Typically, the first nucleotide of a PAM can be any nucleotide, while the two other nucleotides will depend on the specific Cas9 protein that is chosen. Exemplary PAM sequences are known to those of skill in the art and include, without limitation, NNG, NGN, NAG, and NGG, wherein N represents any nucleotide. In certain embodiments, the allele targeted by a gRNA comprises a mutation that creates a PAM within the allele, wherein the PAM promotes binding of the Cas9-gRNA complex to the allele.

In certain embodiments, the gRNA is 5-50 nucleotides, 10-30 nucleotides, 15-25 nucleotides, 18-22 nucleotides, or 19-21 nucleotides in length, or any length between the stated ranges, including, for example, 10, 11, 12, 13, 14, 15, 16, 17, 18, 19, 20, 21, 22, 23, 24, 25, 26, 27, 28, 29, 30, 31, 32, 33, 34, or 35 nucleotides in length. The guide RNA may be a single guide RNA comprising crRNA and tracrRNA sequences in a single RNA molecule, or the guide RNA may comprise two RNA molecules with crRNA and tracrRNA sequences residing in separate RNA molecules.

Donor polynucleotides and gRNAs are readily synthesized by standard techniques, e.g., solid phase synthesis via phosphoramidite chemistry, as disclosed in U.S. Pat. Nos. 4,458,066 and 4,415,732, incorporated herein by reference; Beaucage et al., *Tetrahedron* (1992) 48:2223-2311; and Applied Biosystems User Bulletin No. 13 (Apr. 1, 1987). Other chemical synthesis methods include, for example, the phosphotriester method described by Narang et al., *Meth. Enzymol.* (1979) 68:90 and the phosphodiester method disclosed by Brown et al., *Meth. Enzymol.* (1979) 68:109.

In some instances, a population of cells may be enriched for those comprising a genetic modification by separating the genetically modified cells from the remaining population. Separation of genetically modified cells typically relies upon the expression of a selectable marker co-integrated with the intended edit at the target locus. After the first HDR step, positive selection is performed to isolate cells from a population, e.g. to create an enriched population of cells comprising the genetic modification. After the second HDR step, negative selection is performed to remove cells still containing unwanted sequences such as from a selection marker expression cassette.

Cell separation may be accomplished by any convenient separation technique appropriate for the selection marker used, including, but not limited to flow cytometry, fluorescence activated cell sorting (FACS), magnetic-activated cell sorting (MACS), elutriation, immunopurification, and affinity chromatography. For example, if a fluorescent marker is used, cells may be separated by fluorescence activated cell sorting (FACS), whereas if a cell surface marker is used, cells may be separated from the heterogeneous population by affinity separation techniques, e.g. MACS, affinity chromatography, "panning" with an affinity reagent attached to a solid matrix, immunopurification with an antibody specific for the cell surface marker, or other convenient technique.

In certain embodiments, positive or negative selection of genetically modified cells is performed using a binding agent that specifically binds to a selection marker on a cell (e.g., such as produced from a selection marker expression cassette included in a donor polynucleotide). Examples of binding agents include, without limitation, antibodies, antibody fragments, antibody mimetics, and aptamers. In some embodiments, the binding agent binds to the selection marker with high affinity. The binding agent may be immobilized on a solid support to facilitate isolation of genetically modified cells from a liquid culture. Exemplary solid supports include a magnetic bead, a non-magnetic bead, a slide, a gel, a membrane, and a microtiter plate well.

In certain embodiments, the binding agent comprises an antibody that specifically binds to the selection marker on a cell. Any type of antibody may be used, including polyclonal and monoclonal antibodies, hybrid antibodies, altered antibodies, chimeric antibodies and, humanized antibodies, as well as: hybrid (chimeric) antibody molecules (see, for example, Winter et al. (1991) *Nature* 349:293-299; and U.S. Pat. No. 4,816,567); F(ab')$_2$ and F(ab) fragments; F$_v$ molecules (noncovalent heterodimers, see, for example, Inbar et al. (1972) *Proc Natl Acad Sci USA* 69:2659-2662; and Ehrlich et al. (1980) *Biochem* 19:4091-4096); single-chain Fv molecules (sFv) (see, e.g., Huston et al. (1988) *Proc Natl Acad Sci USA* 85:5879-5883); nanobodies or single-domain antibodies (sdAb) (see, e.g., Wang et al. (2016) *Int J Nanomedicine* 11:3287-3303, Vincke et al. (2012) *Methods Mol Biol* 911:15-26; dimeric and trimeric antibody fragment constructs; minibodies (see, e.g., Pack et al. (1992) *Biochem* 31:1579-1584; Cumber et al. (1992) *J Immunology* 149B: 120-126); humanized antibody molecules (see, e.g., Riechmann et al. (1988) *Nature* 332:323-327; Verhoeyan et al. (1988) *Science* 239:1534-1536; and U.K. Patent Publication No. GB 2,276,169, published Sep. 21, 1994); and, any functional fragments obtained from such molecules, wherein such fragments retain specific-binding properties of the parent antibody molecule (i.e., specifically binds to a selection marker on a cell).

In other embodiments, the binding agent comprises an aptamer that specifically binds to the selection marker on a cell. Any type of aptamer may be used, including a DNA, RNA, xeno-nucleic acid (XNA), or peptide aptamer that specifically binds to the target antibody isotype. Such aptamers can be identified, for example, by screening a combinatorial library. Nucleic acid aptamers (e.g., DNA or RNA aptamers) that bind selectively to a target antibody isotype can be produced by carrying out repeated rounds of in vitro selection or systematic evolution of ligands by exponential enrichment (SELEX). Peptide aptamers that bind to a selection marker on a cell may be isolated from a combinatorial library and improved by directed mutation or repeated rounds of mutagenesis and selection. For a description of methods of producing aptamers, see, e.g., *Aptamers: Tools for Nanotherapy and Molecular Imaging* (R. N. Veedu ed., Pan Stanford, 2016), *Nucleic Acid and Peptide Aptamers: Methods and Protocols* (Methods in Molecular Biology, G. Mayer ed., Humana Press, 2009), *Nucleic Acid Aptamers: Selection, Characterization, and Application* (Methods in Molecular Biology, G. Mayer ed., Humana Press, 2016), *Aptamers Selected by Cell-SELEX for Theranostics* (W. Tan, X. Fang eds., Springer, 2015), Cox et al. (2001) *Bioorg. Med. Chem.* 9(10):2525-2531; Cox et al. (2002) *Nucleic Acids Res.* 30(20): e108, Kenan et al. (1999) *Methods Mol Biol.* 118:217-231; Platella et al. (2016) *Biochim. Biophys.*

Acta Nov 16 pii: S0304-4165(16)30447-0, and Lyu et al. (2016) Theranostics 6(9):1440-1452; herein incorporated by reference in their entireties.

In yet other embodiments, the binding agent comprises an antibody mimetic. Any type of antibody mimetic may be used, including, but not limited to, affibody molecules (Nygren (2008) FEBS J. 275 (11):2668-2676), affilins (Ebersbach et al. (2007) J. Mol. Biol. 372 (1):172-185), affimers (Johnson et al. (2012) Anal. Chem. 84 (15):6553-6560), affitins (Krehenbrink et al. (2008) J. Mol. Biol. 383 (5): 1058-1068), alphabodies (Desmet et al. (2014) Nature Communications 5:5237), anticalins (Skerra (2008) FEBS J. 275 (11):2677-2683), avimers (Silverman et al. (2005) Nat. Biotechnol. 23 (12):1556-1561), darpins (Stumpp et al. (2008) Drug Discov. Today 13 (15-16):695-701), fynomers (Grabulovski et al. (2007) J. Biol. Chem. 282 (5):3196-3204), and monobodies (Koide et al. (2007) Methods Mol. Biol. 352:95-109).

In positive selection, cells carrying a selection marker are collected, whereas in negative selection, cells carrying a selection marker are removed from a cell population. For example, in positive selection, a binding agent specific for a surface marker can be immobilized on a solid support (e.g., column or magnetic bead) and used to collect cells of interest on the solid support. Cells that are not of interest do not bind to the solid support (e.g., flow through the column or do not attach to the magnetic beads). In negative selection, the binding agent is used to deplete a cell population of cells that are not of interest. The cells of interest are those that do not bind to the binding agent (e.g., flow through the column or remain after the magnetic beads are removed).

Dead cells may be selected against by employing dyes that preferentially stain dead cells (e.g. propidium iodide). Any technique may be employed which is not unduly detrimental to the viability of the genetically modified cells.

Compositions that are highly enriched for cells having the desired genetic modification can be produced in this manner. By "highly enriched" is meant that the genetically modified cells are 70% or more, 75% or more, 80% or more, 85% or more, 90% or more, or 95% or more, or 98% or more of the cell composition. In other words, the composition may be a substantially pure composition of genetically modified cells.

Genetically modified cells produced by the methods described herein may be used immediately. Alternatively, the cells may be frozen at liquid nitrogen temperatures and stored for long periods of time before being thawed and used. In such cases, cells may be frozen in 10% DMSO, 50% serum, 40% buffered medium, or some other such solution as is commonly used in the art to preserve cells at such freezing temperatures, and thawed in a manner as commonly known in the art for thawing frozen cultured cells.

In certain embodiments, an inhibitor of the non-homologous end joining (NHEJ) pathway is used to increase the frequency of cells genetically modified by HDR. Examples of inhibitors of the NHEJ pathway include any compound (agent) that inhibits or blocks either expression or activity of any protein component in the NHEJ pathway. Protein components of the NHEJ pathway include, but are not limited to, Ku70, Ku86, DNA protein kinase (DNA-PK), Rad50, MRE11, NBS1, DNA ligase IV, and XRCC4. An exemplary inhibitor is wortmannin which inhibits at least one protein component (e.g., DNA-PK) of the NHEJ pathway. Another exemplary inhibitor is Scr7 (5,6-bis((E)-benzylideneamino)-2-mercaptopyrimidin-4-ol), which inhibits joining of DSBs (Maruyama et al. (2015) Nat. Biotechnol. 33(5):538-542, Lin et al. (2016) Sci. Rep. 6:34531). RNA interference may also be used to block expression of a protein component of the NHEJ pathway (e.g., DNA-PK or DNA ligase IV). For example, small interfering RNAs (siRNAs), hairpin RNAs, and other RNA or RNA:DNA species which can be cleaved or dissociated in vivo to form siRNAs may be used. Alternatively, an HDR enhancer such as RS-1 may be used to increase the frequency of HDR in cells (Song et al. (2016) Nat. Commun. 7:10548).

Figure 4A:
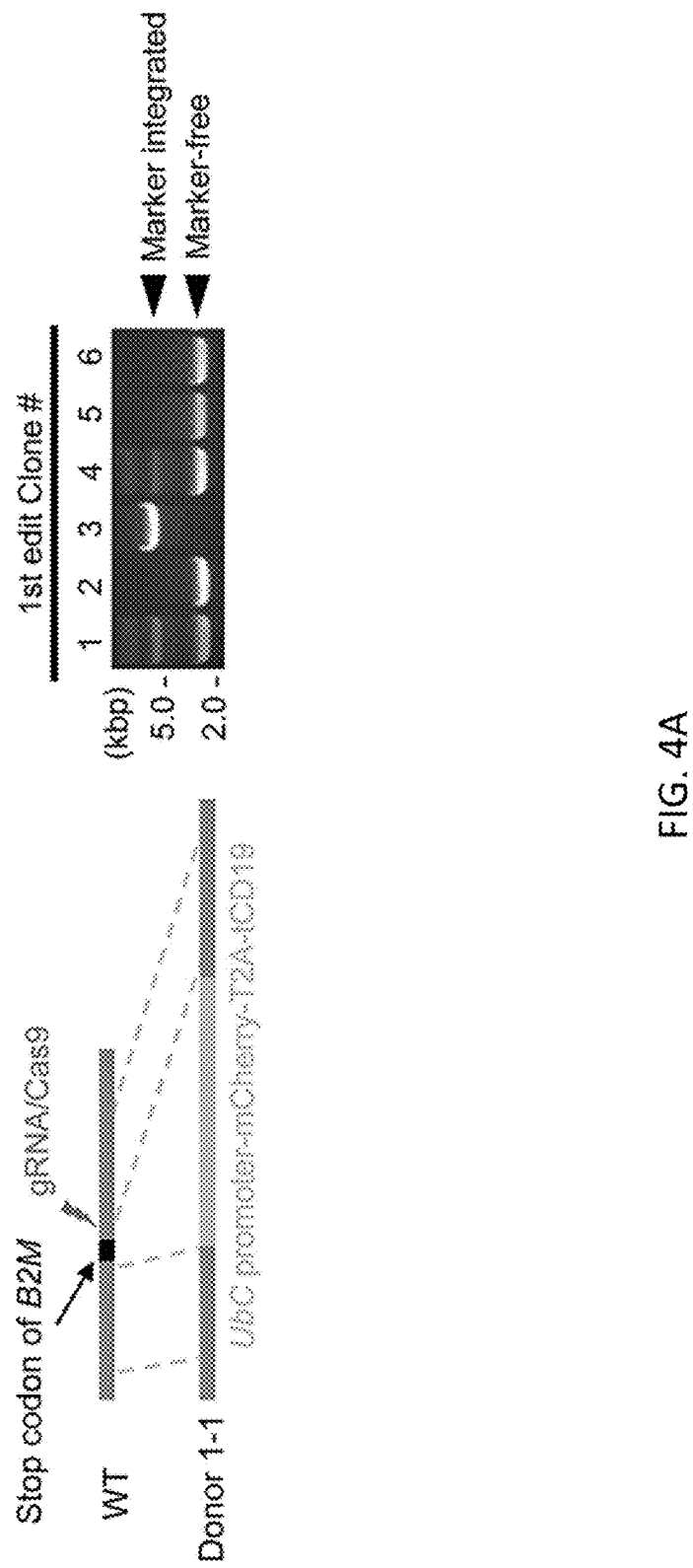
FIGS. 4A-4D show bi-allelic scarless HLA-A*24 cDNA (1.1 kb) integration at just before the stop codon of B2M gene using a donor vector with an shRNA (shGFP) expression cassette in the ES H9 line. Schematic representation of donor DNA design and genotyping by PCR.

In certain embodiments, the first donor polynucleotide further comprises at least one expression cassette encoding a short hairpin RNA (shRNA) comprising a stem-loop structure that inhibits expression of selection markers that are randomly integrated or episomal. An exemplary construct is shown in FIG. 4A, wherein the first donor polynucleotide comprises a pair of expression cassettes encoding the shRNA, wherein the first expression cassette of the pair is located 5' to the first left homology arm and the second expression cassette of the pair is located 3' to the first right homology arm.

The method steps using a Cas9 nuclease, donor polynucleotides, and guide RNAs, as described herein, can be repeated to provide any desired number of DNA modifications. Further, the methods can be adapted to provide multiplex genome editing of cells. For example, multiple genes can be edited simultaneously by pooling multiple donor polynucleotides and guide RNAs that specifically target the separate genes.

B. Nucleic Acids Encoding Donor Polynucleotides, Guide RNAs, and Cas9

In certain embodiments, the donor polynucleotides, guide RNAs, and/or Cas9 are expressed in vivo from a vector. A "vector" is a composition of matter which can be used to deliver a nucleic acid of interest to the interior of a cell. Donor polynucleotides, guide RNAs, and Cas9 can be introduced into a cell with a single vector or in multiple separate vectors. The ability of constructs to produce the donor polynucleotides, guide RNAs, and Cas9 nuclease and genetically modify cells can be empirically determined (e.g., see Example 1 describing the use of the mCherry fluorescent marker for detection of genetically modified cells and immunomagnetic separation of cells expressing a tCD19 surface marker).

Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, lentiviral vectors, and the like. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention.

In one embodiment, an expression vector for expressing a donor polynucleotide, gRNA, or Cas9 comprises a promoter "operably linked" to a polynucleotide encoding the donor polynucleotide, gRNA, or Cas9. The phrase "operably linked" or "under transcriptional control" as used herein means that the promoter is in the correct location and orientation in relation to a polynucleotide to control the initiation of transcription by RNA polymerase and expression of the polynucleotide.

In certain embodiments, the nucleic acid encoding a polynucleotide of interest is under transcriptional control of a promoter. A "promoter" refers to a DNA sequence recognized by the synthetic machinery of the cell, or introduced synthetic machinery, required to initiate the specific transcription of a gene. The term promoter will be used here to refer to a group of transcriptional control modules that are clustered around the initiation site for RNA polymerase I, II, or III. Typical promoters for mammalian cell expression include the SV40 early promoter, a CMV promoter such as the CMV immediate early promoter (see, U.S. Pat. Nos. 5,168,062 and 5,385,839, incorporated herein by reference in their entireties), the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. These and other promoters can be obtained from commercially available plasmids, using techniques well known in the art. See, e.g., Sambrook et al., supra. Enhancer elements may be used in association with the promoter to increase expression levels of the constructs. Examples include the SV40 early gene enhancer, as described in Dijkema et al., *EMBO J.* (1985) 4:761, the enhancer/promoter derived from the long terminal repeat (LTR) of the Rous Sarcoma Virus, as described in Gorman et al., *Proc. Natl. Acad. Sci. USA* (1982b) 79:6777 and elements derived from human CMV, as described in Boshart et al., *Cell* (1985) 41:521, such as elements included in the CMV intron A sequence.

Typically, transcription terminator/polyadenylation signals will also be present in the expression construct. Examples of such sequences include, but are not limited to, those derived from SV40, as described in Sambrook et al., supra, as well as a bovine growth hormone terminator sequence (see, e.g., U.S. Pat. No. 5,122,458). Additionally, 5'-UTR sequences can be placed adjacent to the coding sequence in order to enhance expression of the same. Such sequences may include UTRs comprising an internal ribosome entry site (IRES).

Inclusion of an IRES permits the translation of one or more open reading frames from a vector. The IRES element attracts a eukaryotic ribosomal translation initiation complex and promotes translation initiation. See, e.g., Kaufman et al., *Nuc. Acids Res.* (1991) 19:4485-4490; Gurtu et al., *Biochem. Biophys. Res. Comm.* (1996) 229:295-298; Rees et al., *BioTechniques* (1996) 20:102-110; Kobayashi et al., *BioTechniques* (1996) 21:399-402; and Mosser et al., *BioTechniques* (1997 22 150-161. A multitude of IRES sequences are known and include sequences derived from a wide variety of viruses, such as from leader sequences of picornaviruses such as the encephalomyocarditis virus (EMCV) UTR (Jang et al. *J. Virol.* (1989) 63:1651-1660), the polio leader sequence, the hepatitis A virus leader, the hepatitis C virus IRES, human rhinovirus type 2 IRES (Dobrikova et al., *Proc. Natl. Acad. Sci.* (2003) 100(25): 15125-15130), an IRES element from the foot and mouth disease virus (Ramesh et al., *Nucl. Acid Res.* (1996) 24:2697-2700), a giardiavirus IRES (Garlapati et al., *J. Biol. Chem.* (2004) 279(5):3389-3397), and the like. A variety of nonviral IRES sequences will also find use herein, including, but not limited to IRES sequences from yeast, as well as the human angiotensin II type 1 receptor IRES (Martin et al., *Mol. Cell Endocrinol.* (2003) 212:51-61), fibroblast growth factor IRESs (FGF-1 IRES and FGF-2 IRES, Martineau et al. (2004) *Mol. Cell. Biol.* 24(17):7622-7635), vascular endothelial growth factor IRES (Baranick et al. (2008) Proc. Natl. Acad. Sci. U.S.A. 105(12):4733-4738, Stein et al. (1998) *Mol. Cell. Biol.* 18(6):3112-3119, Bert et al. (2006) RNA 12(6):1074-1083), and insulin-like growth factor 2 IRES (Pedersen et al. (2002) *Biochem. J.* 363(Pt 1):37-44). These elements are readily commercially available in plasmids sold, e.g., by Clontech (Mountain View, Calif.), Invivogen (San Diego, Calif.), Addgene (Cambridge, Mass.) and GeneCopoeia (Rockville, Md.). See also IRESite: The database of experimentally verified IRES structures (iresite.org). An IRES sequence may be included in a vector, for example, to express multiple selection markers or Cas9 in combination with one or more selection markers from an expression cassette.

Alternatively, a polynucleotide encoding a viral T2A peptide can be used to allow production of multiple protein products (e.g., Cas9, one or more selection markers) from a single vector. 2A linker peptides are inserted between the coding sequences in the multicistronic construct. The 2A peptide, which is self-cleaving, allows co-expressed proteins from the multicistronic construct to be produced at equimolar levels. 2A peptides from various viruses may be used, including, but not limited to 2A peptides derived from the foot-and-mouth disease virus, equine rhinitis A virus, *Thosea asigna* virus and porcine teschovirus-1. See, e.g., Kim et al. (2011) PLoS One 6(4):e18556, Trichas et al. (2008) BMC Biol. 6:40, Provost et al. (2007) Genesis 45(10):625-629, Furler et al. (2001) Gene Ther. 8(11):864-873; herein incorporated by reference in their entireties.

There are a number of ways in which expression vectors may be introduced into cells. In certain embodiments, the expression construct comprises a virus or engineered construct derived from a viral genome. A number of viral based systems have been developed for gene transfer into mammalian cells. These include adenoviruses, retroviruses (γ-retroviruses and lentiviruses), poxviruses, adeno-associated viruses, baculoviruses, and herpes simplex viruses (see e.g., Warnock et al. (2011) Methods Mol. Biol. 737:1-25; Walther et al. (2000) Drugs 60(2):249-271; and Lundstrom (2003) Trends Biotechnol. 21(3):117-122; herein incorporated by reference in their entireties). The ability of certain viruses to enter cells via receptor-mediated endocytosis, to integrate into host cell genomes and express viral genes stably and efficiently have made them attractive candidates for the transfer of foreign genes into mammalian cells.

For example, retroviruses provide a convenient platform for gene delivery systems. Selected sequences can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; Boris-Lawrie and Temin (1993) Cur. Opin. Genet. Develop. 3:102-109; and Ferry et al. (2011) Curr. Pharm. Des. 17(24):2516-2527). Lentiviruses are a class of retroviruses that are particularly useful for delivering polynucleotides to mammalian cells because they are able to infect both dividing and nondividing cells (see e.g., Lois et al (2002) Science 295:868-872; Durand et al. (2011) Viruses 3(2):132-159; herein incorporated by reference).

A number of adenovirus vectors have also been described. Unlike retroviruses which integrate into the host genome, adenoviruses persist extrachromosomally thus minimizing the risks associated with insertional mutagenesis (Haj-Ahmad and Graham, J. Virol. (1986) 57:267-274; Bett et al., J. Virol. (1993) 67:5911-5921; Mittereder et al., Human Gene Therapy (1994) 5:717-729; Seth et al., J. Virol. (1994) 68:933-940; Barr et al., Gene Therapy (1994) 1:51-58;

Berkner, K. L. BioTechniques (1988) 6:616-629; and Rich et al., Human Gene Therapy (1993) 4:461-476). Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published Jan. 23, 1992) and WO 93/03769 (published Mar. 4, 1993); Lebkowski et al., Molec. Cell. Biol. (1988) 8:3988-3996; Vincent et al., Vaccines 90 (1990) (Cold Spring Harbor Laboratory Press); Carter, B. J. Current Opinion in Biotechnology (1992) 3:533-539; Muzyczka, N. Current Topics in Microbiol. and Immunol. (1992) 158:97-129; Kotin, R. M. Human Gene Therapy (1994) 5:793-801; Shelling and Smith, Gene Therapy (1994) 1:165-169; and Zhou et al., J. Exp. Med. (1994) 179:1867-1875.

Another vector system useful for delivering the polynucleotides of the present invention is the enterically administered recombinant poxvirus vaccines described by Small, Jr., P. A., et al. (U.S. Pat. No. 5,676,950, issued Oct. 14, 1997, herein incorporated by reference).

Additional viral vectors which will find use for delivering the nucleic acid molecules of interest include those derived from the pox family of viruses, including vaccinia virus and avian poxvirus. By way of example, vaccinia virus recombinants expressing a nucleic acid molecule of interest (e.g., a donor polynucleotide, gRNA, or Cas9) can be constructed as follows. The DNA encoding the particular nucleic acid sequence is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the sequences of interest into the viral genome. The resulting TK-recombinant can be selected by culturing the cells in the presence of 5-bromodeoxyuridine and picking viral plaques resistant thereto.

Alternatively, avipoxviruses, such as the fowlpox and canarypox viruses, can also be used to deliver the nucleic acid molecules of interest. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael et al., J. Biol. Chem. (1993) 268:6866-6869 and Wagner et al., Proc. Natl. Acad. Sci. USA (1992) 89:6099-6103, can also be used for gene delivery.

Members of the alphavirus genus, such as, but not limited to, vectors derived from the Sindbis virus (SIN), Semliki Forest virus (SFV), and Venezuelan Equine Encephalitis virus (VEE), will also find use as viral vectors for delivering the polynucleotides of the present invention. For a description of Sindbis-virus derived vectors useful for the practice of the instant methods, see, Dubensky et al. (1996) J. Virol. 70:508-519; and International Publication Nos. WO 95/07995, WO 96/17072; as well as, Dubensky, Jr., T. W., et al., U.S. Pat. No. 5,843,723, issued Dec. 1, 1998, and Dubensky, Jr., T. W., U.S. Pat. No. 5,789,245, issued Aug. 4, 1998, both herein incorporated by reference. Particularly preferred are chimeric alphavirus vectors comprised of sequences derived from Sindbis virus and Venezuelan equine encephalitis virus. See, e.g., Perri et al. (2003) J. Virol. 77: 10394-10403 and International Publication Nos. WO 02/099035, WO 02/080982, WO 01/81609, and WO 00/61772; herein incorporated by reference in their entireties.

A vaccinia-based infection/transfection system can be conveniently used to provide for inducible, transient expression of the polynucleotides of interest (e.g., miR-181 or a mimic or inhibitor thereof) in a host cell. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide of interest, driven by a T7 promoter. The polymerase expressed in the cytoplasm from the vaccinia virus recombinant transcribes the transfected DNA into RNA. The method provides for high level, transient, cytoplasmic production of large quantities of RNA. See, e.g., Elroy-Stein and Moss, Proc. Natl. Acad. Sci. USA (1990) 87:6743-6747; Fuerst et al., Proc. Natl. Acad. Sci. USA (1986) 83:8122-8126.

As an alternative approach to infection with vaccinia or avipox virus recombinants, or to the delivery of nucleic acids using other viral vectors, an amplification system can be used that will lead to high level expression following introduction into host cells. Specifically, a T7 RNA polymerase promoter preceding the coding region for T7 RNA polymerase can be engineered. Translation of RNA derived from this template will generate T7 RNA polymerase which in turn will transcribe more templates. Concomitantly, there will be a cDNA whose expression is under the control of the T7 promoter. Thus, some of the T7 RNA polymerase generated from translation of the amplification template RNA will lead to transcription of the desired gene. Because some T7 RNA polymerase is required to initiate the amplification, T7 RNA polymerase can be introduced into cells along with the template(s) to prime the transcription reaction. The polymerase can be introduced as a protein or on a plasmid encoding the RNA polymerase. For a further discussion of T7 systems and their use for transforming cells, see, e.g., International Publication No. WO 94/26911; Studier and Moffatt, J. Mol. Biol. (1986) 189:113-130; Deng and Wolff, Gene (1994) 143:245-249; Gao et al., Biochem. Biophys. Res. Commun. (1994) 200:1201-1206; Gao and Huang, Nuc. Acids Res. (1993) 21:2867-2872; Chen et al., Nuc. Acids Res. (1994) 22:2114-2120; and U.S. Pat. No. 5,135,855.

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsulated in an infectious viral particle.

Several non-viral methods for the transfer of expression constructs into cultured mammalian cells also are contemplated by the present invention. These include the use of calcium phosphate precipitation, DEAE-dextran, electroporation, direct microinjection, DNA-loaded liposomes, lipofectamine-DNA complexes, cell sonication, gene bombardment using high velocity microprojectiles, and receptor-mediated transfection (see, e.g., Graham and Van Der Eb (1973) Virology 52:456-467; Chen and Okayama (1987) Mol. Cell Biol. 7:2745-2752; Rippe et al. (1990) Mol. Cell Biol. 10:689-695; Gopal (1985) Mol. Cell Biol. 5:1188-

1190; Tur-Kaspa et al. (1986) Mol. Cell. Biol. 6:716-718; Potter et al. (1984) Proc. Natl. Acad. Sci. USA 81:7161-7165); Harland and Weintraub (1985) J. Cell Biol. 101:1094-1099); Nicolau and Sene (1982) Biochim. Biophys. Acta 721:185-190; Fraley et al. (1979) Proc. Natl. Acad. Sci. USA 76:3348-3352; Fechheimer et al. (1987) Proc Natl. Acad. Sci. USA 84:8463-8467; Yang et al. (1990) Proc. Natl. Acad. Sci. USA 87:9568-9572; Wu and Wu (1987) J. Biol. Chem. 262:4429-4432; Wu and Wu (1988) Biochemistry 27:887-892; herein incorporated by reference). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (Proc. Natl. Acad. Sci. USA (1984) 81:7529-7533) successfully injected polyomavirus DNA in the form of calcium phosphate precipitates into liver and spleen of adult and newborn mice demonstrating active viral replication and acute infection. Benvenisty and Neshif (Proc. Natl. Acad. Sci. USA (1986) 83:9551-9555) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment, a naked DNA expression construct may be transferred into cells by particle bombardment. This method depends on the ability to accelerate DNA-coated microprojectiles to a high velocity allowing them to pierce cell membranes and enter cells without killing them (Klein et al. (1987) Nature 327:70-73). Several devices for accelerating small particles have been developed. One such device relies on a high voltage discharge to generate an electrical current, which in turn provides the motive force (Yang et al. (1990) Proc. Natl. Acad. Sci. USA 87:9568-9572). The microprojectiles may consist of biologically inert substances, such as tungsten or gold beads.

In a further embodiment, the expression construct may be delivered using liposomes. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat (1991) Liver Diseases, Targeted Diagnosis and Therapy Using Specific Receptors and Ligands, Wu et al. (Eds.), Marcel Dekker, NY, 87-104). Also contemplated is the use of lipofectamine-DNA complexes.

In certain embodiments of the invention, the liposome may be complexed with a hemagglutinating virus (HVJ). This has been shown to facilitate fusion with the cell membrane and promote cell entry of liposome-encapsulated DNA (Kaneda et al. (1989) Science 243:375-378). In other embodiments, the liposome may be complexed or employed in conjunction with nuclear non-histone chromosomal proteins (HMG-I) (Kato et al. (1991) J. Biol. Chem. 266(6): 3361-3364). In yet further embodiments, the liposome may be complexed or employed in conjunction with both HVJ and HMG-I. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu (1993) Adv. Drug Delivery Rev. 12:159-167).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) and transferrin (see, e.g., Wu and Wu (1987), supra; Wagner et al. (1990) Proc. Natl. Acad. Sci. USA 87(9):3410-3414). Recently, a synthetic neoglycoprotein, which recognizes the same receptor as ASOR, has been used as a gene delivery vehicle (Ferkol et al. (1993) FASEB J. 7:1081-1091; Perales et al. (1994) Proc. Natl. Acad. Sci. USA 91(9):4086-4090), and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (Methods Enzymol. (1987) 149:157-176) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell by any number of receptor-ligand systems with or without liposomes. Also, antibodies to surface antigens on cells can similarly be used as targeting moieties.

In a particular example, a recombinant polynucleotide encoding a donor polynucleotide, gRNA, or Cas9 may be administered in combination with a cationic lipid. Examples of cationic lipids include, but are not limited to, lipofectin, DOTMA, DOPE, and DOTAP. The publication of WO/0071096, which is specifically incorporated by reference, describes different formulations, such as a DOTAP: cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877,302, 6,008,336, 6,077,835, 5,972,901, 6,200,801, and 5,972,900, which are incorporated by reference for those aspects.

In certain embodiments, gene transfer may more easily be performed under ex vivo conditions. Ex vivo gene therapy refers to the isolation of cells from a subject, the delivery of a nucleic acid into cells in vitro, and then the return of the modified cells back into the subject. This may involve the collection of a biological sample comprising cells from the subject. For example, blood can be obtained by venipuncture, and solid tissue samples can be obtained by surgical techniques according to methods well known in the art.

Usually, but not always, the subject who receives the cells (i.e., the recipient) is also the subject from whom the cells are harvested or obtained, which provides the advantage that the donated cells are autologous. However, cells can be obtained from another subject (i.e., donor), a culture of cells from a donor, or from established cell culture lines. Cells may be obtained from the same or a different species than the subject to be treated, but preferably are of the same species, and more preferably of the same immunological profile as the subject. Such cells can be obtained, for example, from a biological sample comprising cells from a close relative or matched donor, then transfected with nucleic acids (e.g., encoding a donor polynucleotide, gRNA, or Cas9), and administered to a subject in need of genome modification, for example, for treatment of a disease or condition.

C. Kits

The above-described reagents including the donor DNAs and guide RNAs for the first and second HDR steps and Cas9 can be provided in kits, with suitable instructions and other necessary reagents for scarless genome modification as described herein. The kit may also contain cells for genome modification, binding agents for positive and negative selection of cells, and transfection agents. The kit will normally contain in separate containers the donor DNAs, guide RNAs, Cas9, and other reagents that are required. Instructions (e.g., written, CD-ROM, DVD, Blu-ray, flash drive, digital download, etc.) for carrying out genome editing as described herein usually will be included in the kit. The kit can also contain, depending on the particular assay used, other packaged reagents and materials (i.e., wash buffers, and the like). Genome editing of cells such as described herein, can be conducted using these kits.

In another embodiment, the kit comprises a first donor polynucleotide comprising a selection marker expression cassette comprising: a UbC promoter, a polynucleotide encoding mCherry, a polynucleotide encoding a T2A peptide, a polynucleotide encoding a truncated CD19 (tCD19), and a polyadenylation sequence. In one embodiment, the donor DNA comprises a selection marker expression cassette comprising a sequence of SEQ ID NO:1 or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein a cell having the first donor polynucleotide integrated into the genomic DNA of the cell at a target site by Cas9-mediated HDR can be identified by positive selection for a selection marker encoded by the expression cassette.

In another embodiment, the kit comprises a second donor polynucleotide comprising a polynucleotide comprising a sequence of SEQ ID NO:2 or a sequence having at least 95% identity to the sequence of SEQ ID NO:2, wherein the second donor polynucleotide is capable of integrating into the modified genomic DNA (i.e. with integrated first donor polynucleotide) of a cell by Cas9-mediated HDR to remove the selection marker expression cassette of the integrated first donor polynucleotide.

In certain embodiments, one or more of the first donor polynucleotide, the second donor polynucleotide, the first guide RNA, the second guide RNA, and the Cas9 in the kit are provided by vector, such as a plasmid or viral vector. In another embodiment, the first guide RNA, and the Cas9 are provided by a single vector or multiple vectors. In another embodiment, the second donor polynucleotide, the second guide RNA, and the Cas9 are provided by a single vector or multiple vectors.

D. Applications

The scarless genome editing methods of the invention will find numerous applications in basic research and development and regenerative medicine. The methods can be used to introduce a mutation (e.g., insertion, deletion, or substitution) into any gene in the genomic DNA of a cell. For example, the methods described herein can be used for inactivation of a gene in a cell to determine the effects of a gene knockout or to study the effects of a known disease-causing mutation. Alternatively, the methods described herein can be used for removal of a mutation, such as a disease-causing mutation, from a gene in the genomic DNA of a cell.

In particular, scarless genome editing as described herein can be used for developing cell lines with desired characteristics. This method can be used, for example, in developing genetic disease models in human ES/iPS cells or adding differentiation marker genes to human ES/iPS cells. Additionally, this method can be used for creation of transgenic animals, addition of reporter genes to cells at desired sites, or genome modification to confer desired features on cells, such as a safety system, potentiated efficacy, controllability and/or improved graft survival.

In certain aspects, the methods of the present invention can be used for ameliorating, treating or preventing diseases in an individual by genome modification as described herein. For example, an allele may contribute to a disease by increasing the individual's susceptibility to the disease or by being a direct causal contributor to the disease. Accordingly, by changing the sequence of the allele, the disease may be ameliorated, treated or prevented. The individual may be a mammal or other animal, preferably human.

More than 3,000 diseases are caused by mutations, including sickle cell anemia, hemophilia, severe combined immunodeficiency (SCID), Tay-Sachs disease, Duchenne's muscular dystrophy, Huntington's disease, alpha-thalassemia, and Lesch Nyhan syndrome. Accordingly, all such genetic diseases may benefit from correction of genetic defects in cells by scarless genome editing as described herein. The methods of the present invention are particularly suitable for diseases in which cells corrected by genome modification have a significant selective advantage over mutant cells, but may also be useful for diseases in which cells corrected by genome modification have no significant selective advantage over mutant cells.

In certain embodiments, the subject methods may be used to alter a genomic target sequence that renders a subject susceptible to an infectious disease. For example, many viral and bacterial pathogens enter a cell by binding to and recruiting a set of cell surface and intracellular proteins. Gene targeting may be used to eliminate or attenuate such a binding site or entry mechanism.

Certain methods described herein may be applied to cells in vitro or ex vivo. Alternatively, the methods may be applied to subjects to effect genome modification in vivo. Donor polynucleotides, guide RNAs, and Cas9, or vectors encoding them can be introduced into an individual using routes of administration generally known in the art (e.g., parenteral, mucosal, nasal, injection, systemic, implant, intraperitoneal, oral, intradermal, transdermal, intramuscular, intravenous including infusion and/or bolus injection, subcutaneous, topical, epidural, buccal, rectal, vaginal, etc.). In certain aspects, donor polynucleotides, guide RNAs, Cas9, and vectors of the present invention can be formulated in combination with a suitable pharmaceutically acceptable carrier (excipient), such as saline, sterile water, dextrose, glycerol, ethanol, Ringer's solution, isotonic sodium chloride solution, and combinations thereof. Formulations should suit the mode of administration, and is well within the skill of the art. The mode of administration is preferably at the location of the target cells to be modified.

Donor polynucleotides, guide RNAs, and Cas9, or vectors encoding them may be administrated to an individual, alone or in conjunction with other therapeutic agents. These different types of therapeutic agents may be administered in the same formulation or in a separate formulation. The dosage of donor polynucleotides, guide RNAs, and Cas9, or vectors encoding them administered to an individual, including the frequency of administration, will vary depending upon a variety of factors, including mode and route of administration; size, age, sex, health, body weight and diet of the recipient; nature and extent of symptoms of the disease or disorder being treated; kind of concurrent treatment, frequency of treatment, and the effect desired; the nature of the formulation; and the judgment of the attending practitioner. Variations in these dosage levels can be adjusted using standard empirical routines for optimization, as is well understood in the art.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Highly Efficient Scarless Genome Editing in Human Pluripotent Stem Cells

In our method, we applied a two-step HR approach to four genes in both human embryonic stem cells (ESCs) and induced pluripotent stem cells (iPSCs) that permits scarless editing on either one or both alleles without creating INDELs while creating either single nucleotide changes or the insertion of larger DNA fragments (such as reporter genes).

Figure 1B:
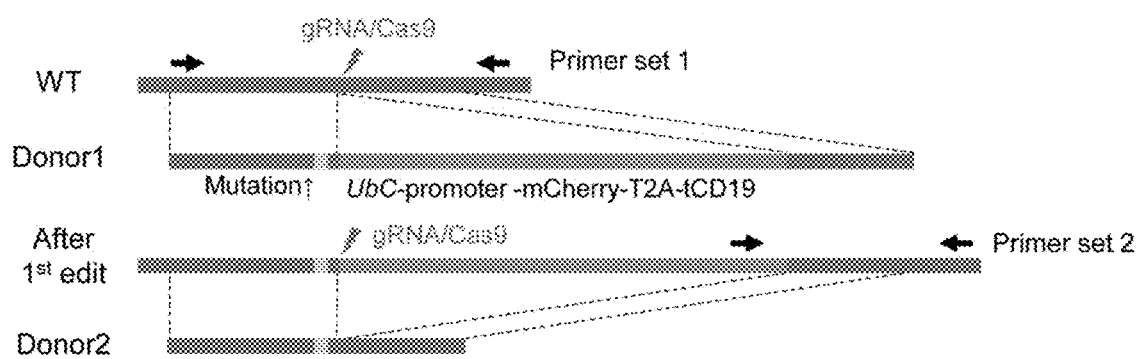
Figure 1C:
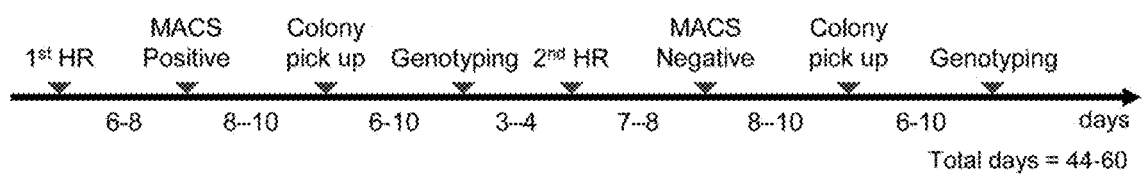
Figure 2A:
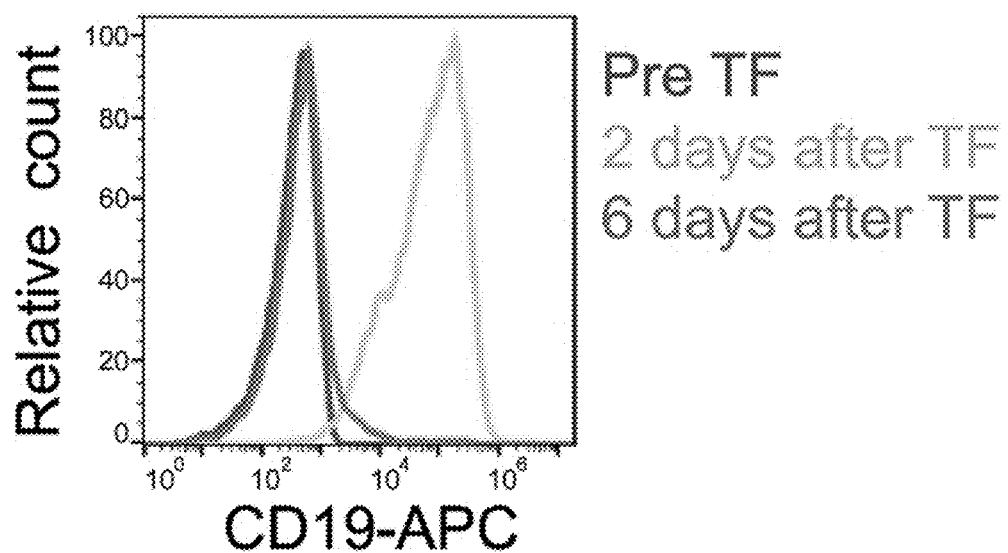
Figure 2B:
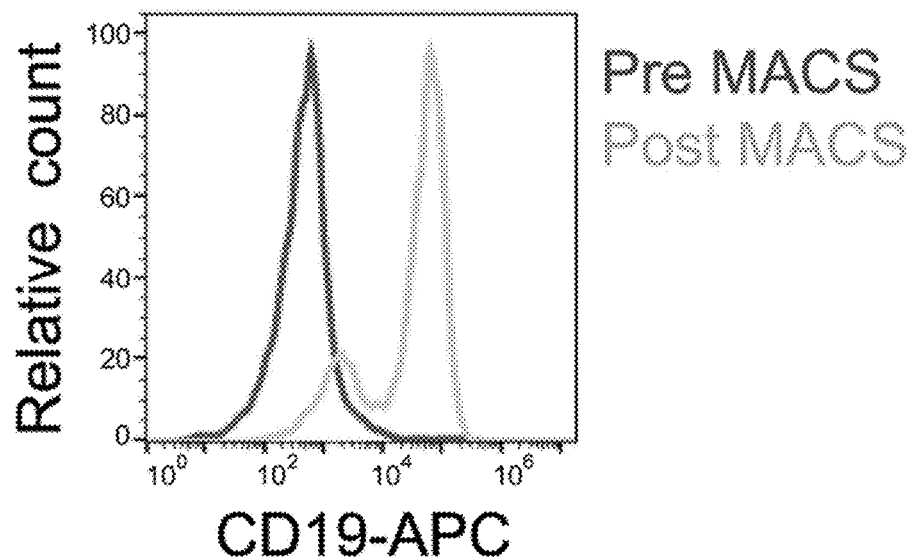
Figure 2C:
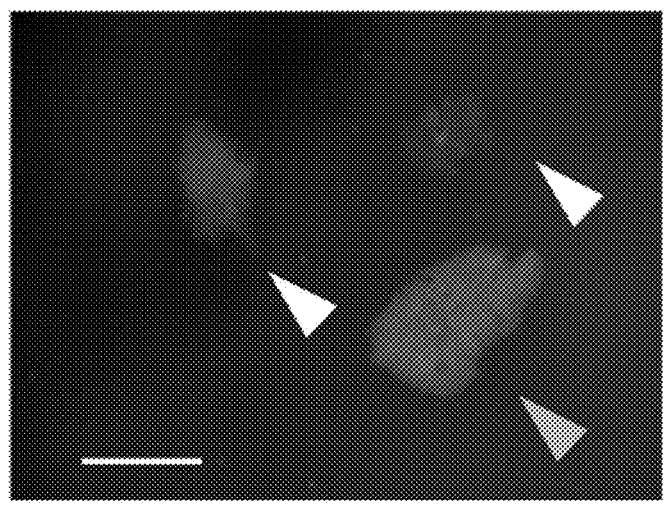
Figure 2D:
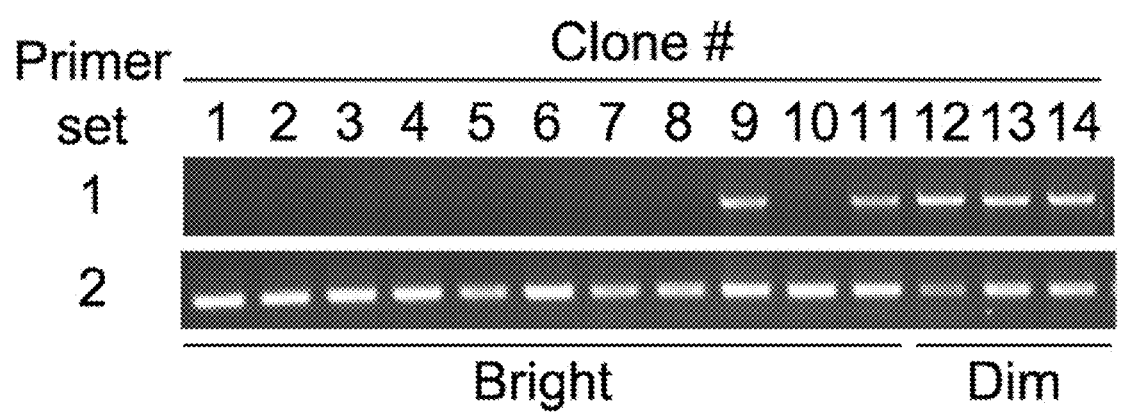
Figure 2E:
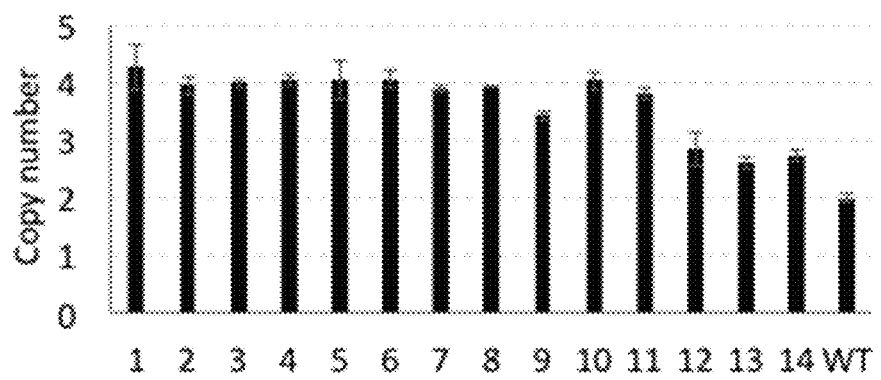
Figure 6A:
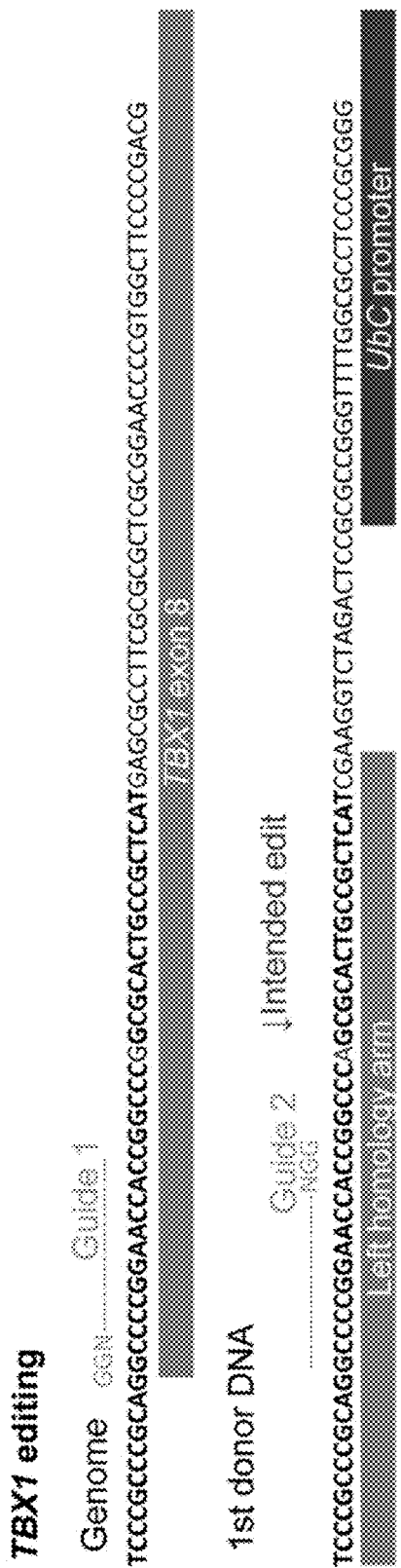

To overcome the limitations of the previous scarless editing methods, we employed a combination of a two-step HR strategy using Cas9/gRNA system and positive-negative selection using magnetic beads (FIGS. 1A-1C). As a proof of concept, we introduced a point mutation in human ESCs within TBX1 at nucleotide position 928 of the cDNA (c.928 G>A), which causes 22q11.2 deletion syndrome, also known as DiGeorge Syndrome (Yagi et al. Lancet 362, 1366-1373 (2003)). Editing this locus would not be possible using the piggyBac system since no TTAA site lies within 1 kb of TBX1 c.928 G. For our method, we transfected hESCs with a plasmid that co-expresses S. pyogenes Cas9 (Cas9) as well as a guide RNA (gRNA) targeted near TBX1 c.928 G (FIG. 6A). In addition to the Cas9/gRNA plasmid, we also transfected a plasmid carrying donor DNA that is used as a repair template following the DSB introduced by the Cas9-gRNA complex. The donor template also contains a bicistronic cassette that expresses mCherry and truncated CD19 (tCD19) under control of the human UbC promoter to serve as a marker between the left and right homology arm (FIG. 1B). Because mCherry and tCD19 are expressed episomally, we observe that transient expression of mCherry, which reduced to 2.1% within 6 days post-transfection (FIG. 2A). Therefore, at 6 days after transfection, we purified tCD19-positive cells by magnetic-assisted cell separation (MACS) selection using anti-CD19 conjugated with magnetic beads (FIG. 2B). Cells were then plated at low density (100 cells/cm$^2$) for single cell cloning. After a further 8 days in culture, we observed colonies with bright or dim mCherry fluorescence (FIG. 2C). Genotyping of TBX1 in these fluorescent cells revealed that 9 of 11 clones with bright mCherry expression possessed bi-allelic editing into the intended TBX1 site (FIG. 2D). We also picked 3 clones with dim mCherry expression, all of which displayed mono-allelic insertion of our marker at the intended loci. For further validation, we verified the copy number of genomically inserted targeting vectors by ddPCR quantification of the UbC promoter. All bright colonies contained 4 copies of the UbC promoter (derived from 2 endogenous copies of the UbC promoter at the ubiquitin locus plus the 2 exogenous copies at our targeted locus, FIG. 2E). This indicates that 9 of 11 clones were correctly targeted without random integration. In line with our hypothesis, all dim colonies contained 3 copies of the UbC promoter, derived from 2 endogenous copies plus one from the mono-allelic editing event within TBX1.

Figure 2F:
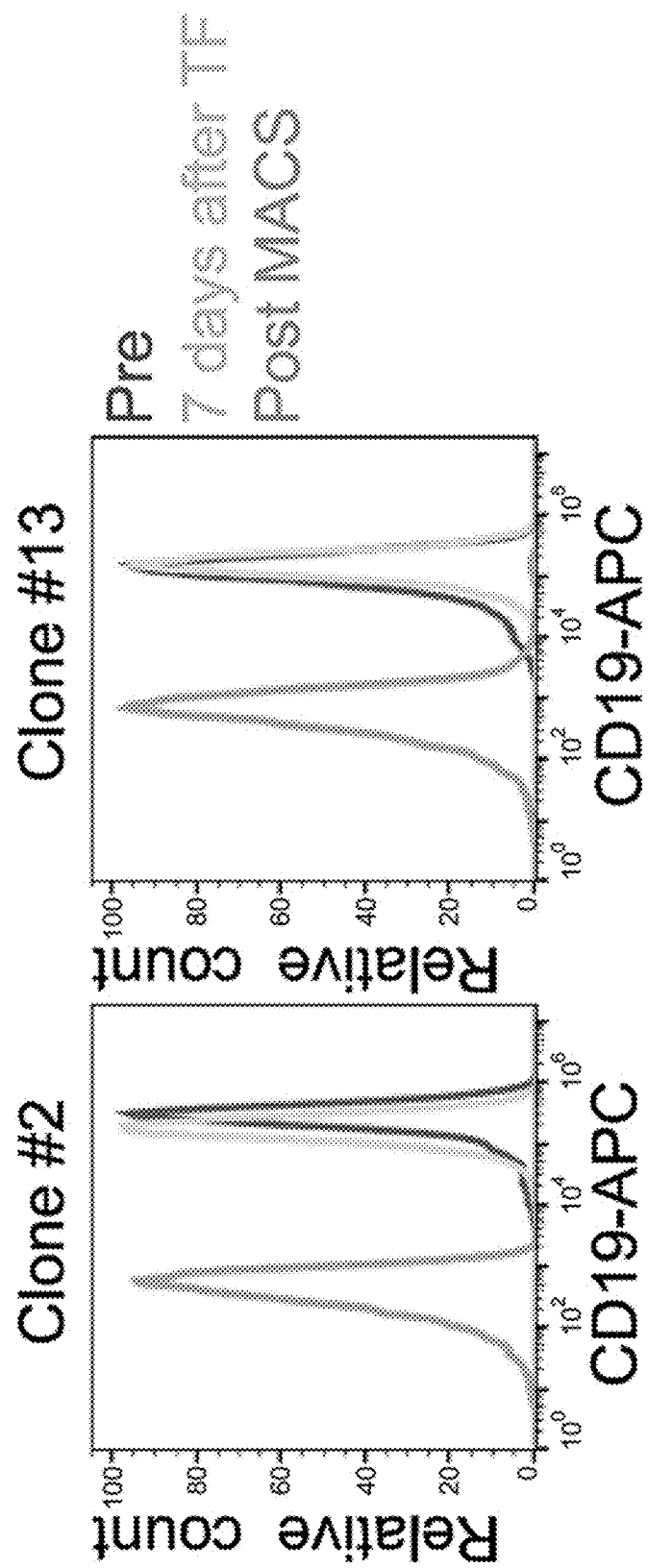
Figure 2H:
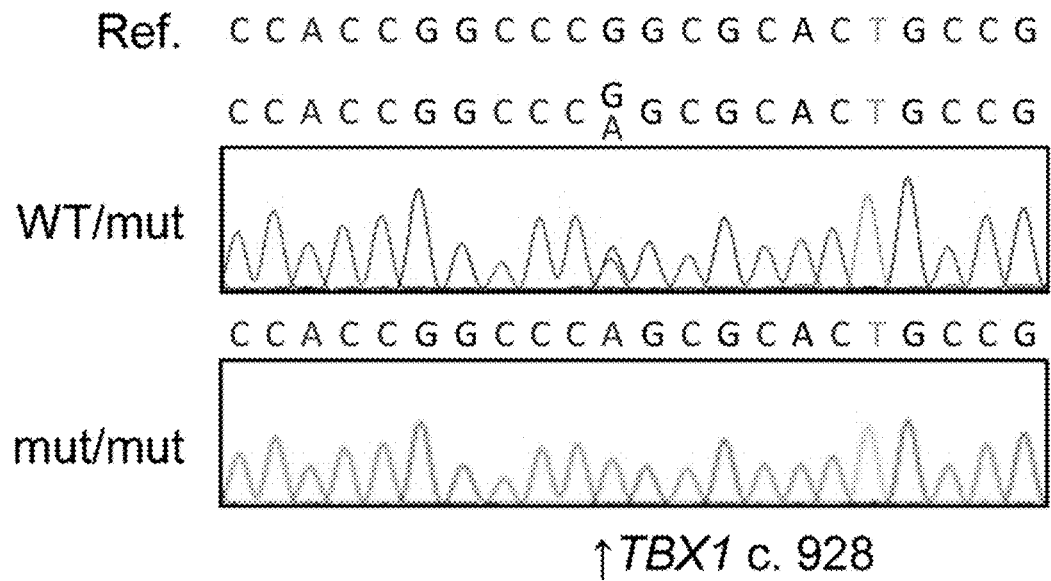
Figure 7A:
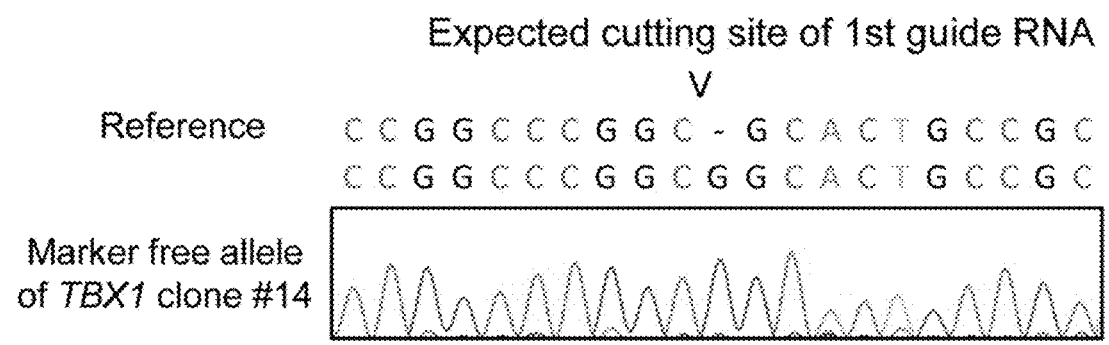
Figure 7C:
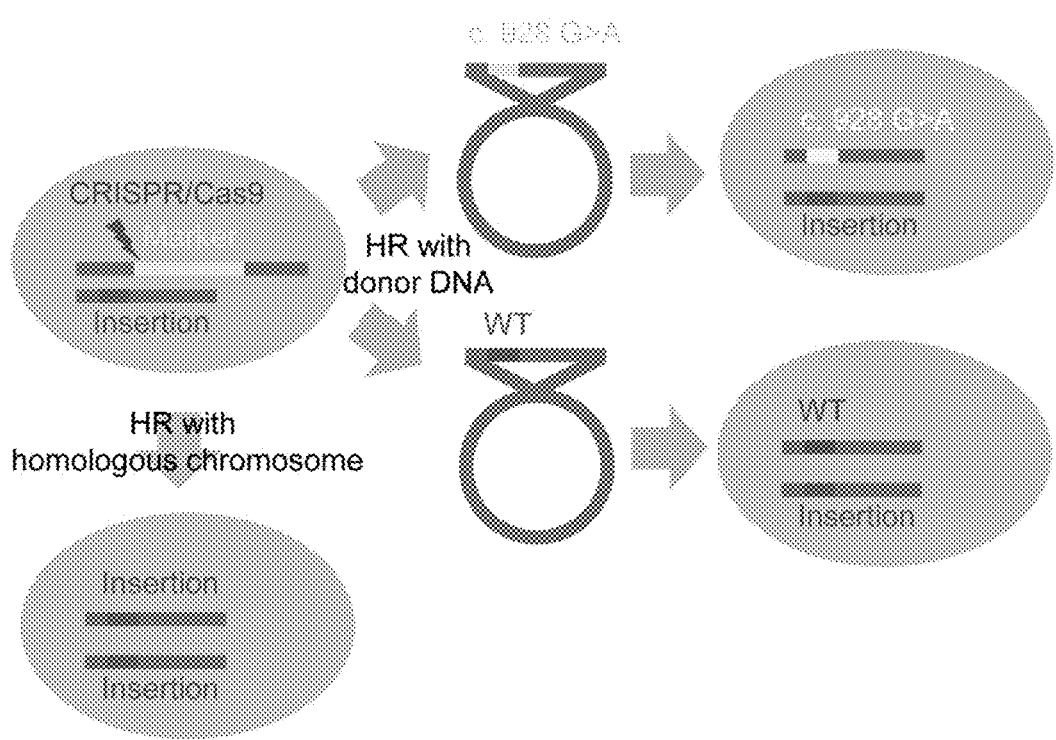
Figure 8:
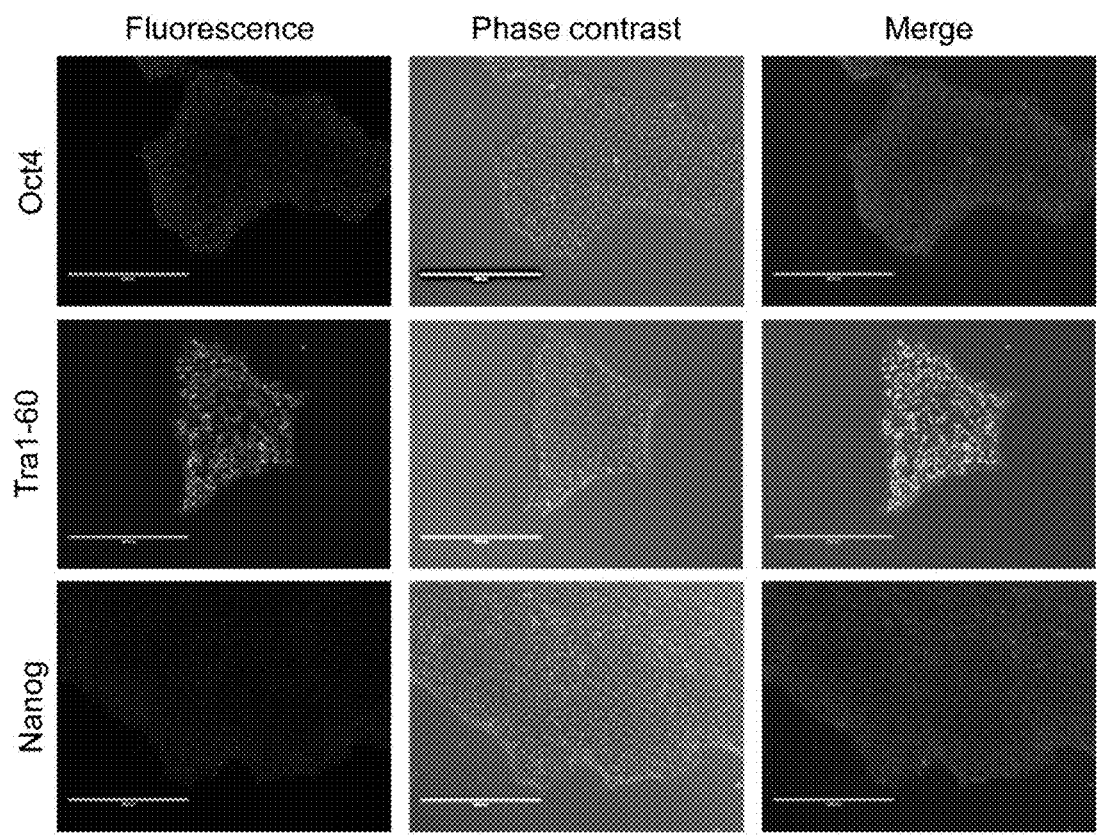
FIG. 8 shows immunostaining of Oct4, Tra1-60 and Nanog in TBX1 edited ES cells (Scale bars=400 μm)
Figure 9A:
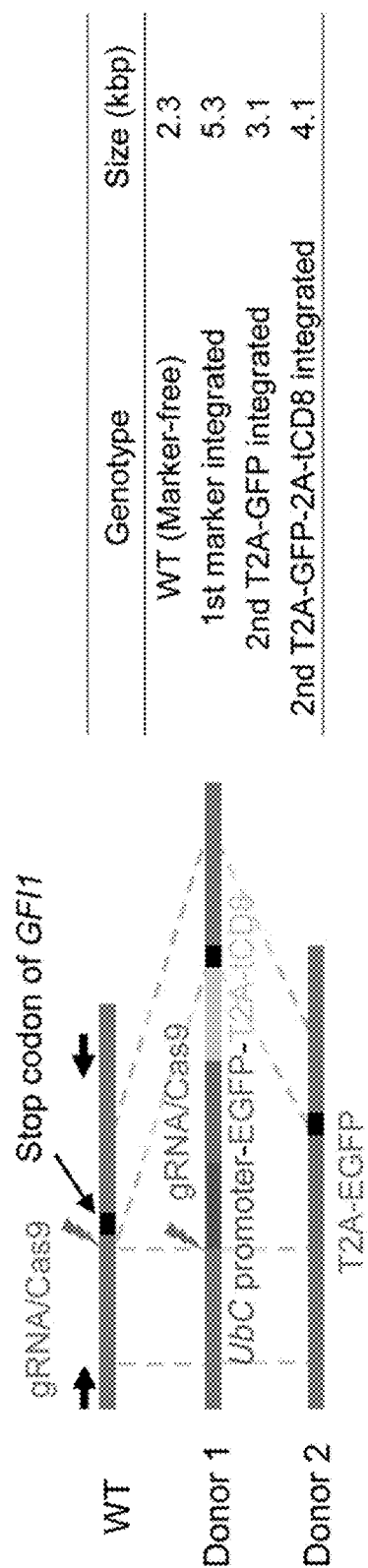
FIGS. 9A-9D show scarless marker integration at just before the stop codon of GFI1 gene in RUNX1-mOrange line.
Figure 9B:
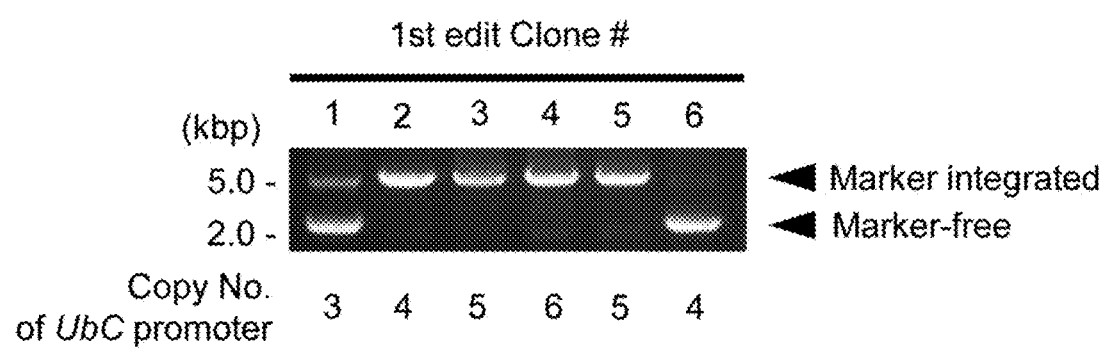
Figure 9C:
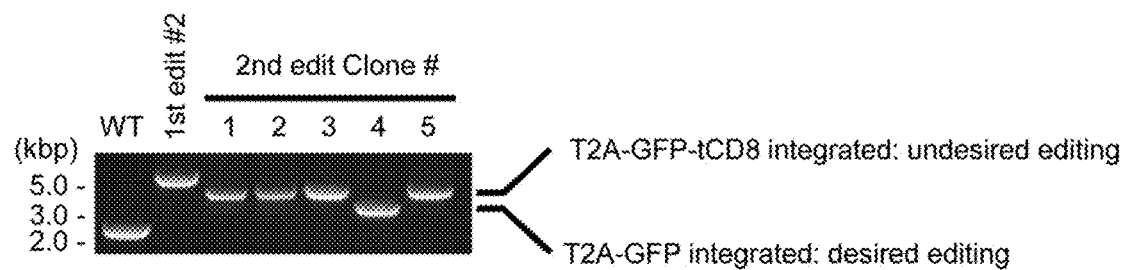
Figure 9D:
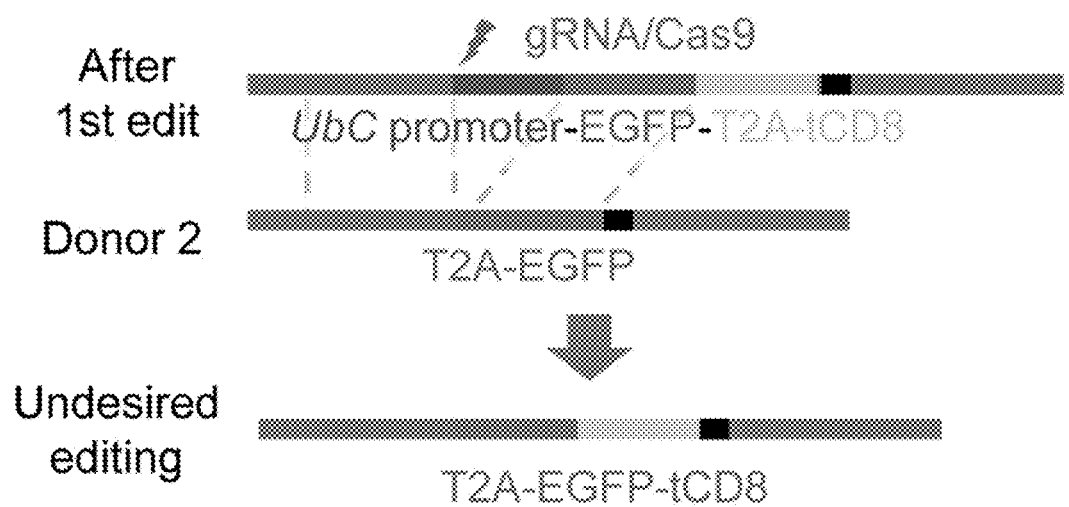

Following the first round of MACS selection, to demonstrate the ability of our method to yield cells with scarless bi- and mono-allelic edits, we performed a second round of HR in bi-allelically edited clone #2 and mono-allelically edited clone #13. This was done as before by transfecting a plasmid expressing Cas9 along with a custom gRNA targeting only the inserted marker (guide 2, FIG. 6A). Guide 2 is designed to have high specificity based on bioinformatic analysis and only targets the junction between the marker gene and the homology arm and thus has no endogenous target sites in the human genome. We simultaneously transfected a plasmid carrying a donor template that contained the TBX1 c. G928 G>A mutation with homology arms that would yield a scarless, marker-free editing event (FIG. 1B). Cells possessing this second edit were purified by MACS negative selection at day 7 post-transfection. Using negative selection, we expand a population of >98% tCD19-negative cells (FIG. 2F). We then used single cell cloning from the tCD19 negative population to identify marker free cells that had undergone bi-allelic editing events. Analysis of clones showed 7 TBX1 c.928 G>A bi-allelically edited lines from 7 distinct clones derived from clone #2 as well as 12 mono-allelically edited lines from 16 clones derived from clone #13 (FIGS. 2G, 2H). Though all 16 clones derived from clone #13 began the 2nd round of HR with mono-allelic editing events, afterward 4 of the 16 clones possessed only WT alleles. We hypothesized that this loss of the mono-allelic editing event was attributed to an HR event using the WT homolog chromosome (not sister chromatid) following the 2nd Cas9-mediated DSB. Supporting this idea, a single clone was found with a homozygous 1 base insertion following the 2nd round of HR, which cannot be derived from contamination of non-edited cells (FIG. 7). In addition, a $2^{nd}$ round of HR in clone #2 using a mixture of WT and TBX1 c.928 G>A donor yielded WT, heterozygous, and homozygous mutants (FIG. 2G). Because of this, WT, heterozygous, and homozygous scarless clones in an isogenic background can easily be obtained for appropriate comparison when modeling disease just as littermate comparisons are performed with genetically-modified animals. Following the $2^{nd}$ round of HR and subsequent negative selection, we confirmed that edited stem cells retained pluripotency markers (FIG. 8)

Figure 3A:
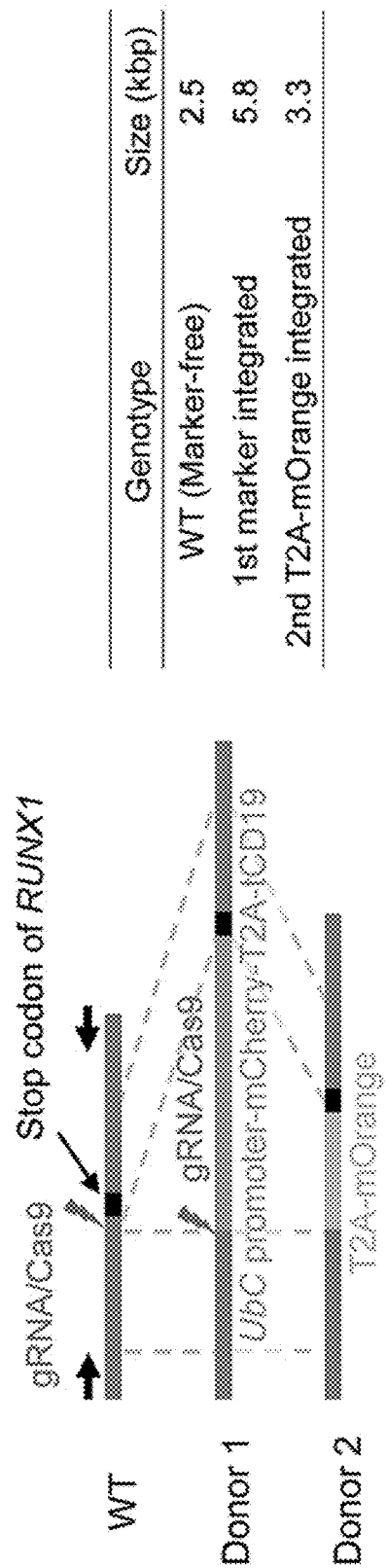
FIGS. 3A-3E show scarless reporter gene integration at 5' side of RUNX1 stop codon in human iPSCs by 2 step editing.

We next applied the same approach to make a RUNX1 reporter iPS cell line by integration of mOrange gene following to 2A self-cleaving peptide sequence at just before the stop codon of RUNX1 gene. The goal of this editing is to create an isogenic scarless RUNX1 reporter to permit image analysis of directed differentiation into RUNX1$^+$ hematopoietic stem and progenitor cells and to screen for culture conditions/small molecules and CRISPR or shRNA based genetic screens to enhance differentiation of PSCs into RUNX1$^+$ cells (FIG. 3A). Because RUNX1 gene does not express in PSCs, it is not easy to obtain the edited line by conventional editing methods, usually hundreds of colonies would have to be picked and analyzed unless marker selection is employed. Through 1st round editing, we inserted a mCherry-tCD19 expression cassette at the 5' side of RUNX1 stop codon using Cas9/gRNA and donor plasmid depicted in FIGS. 6B and 7. After MACS enrichment of tCD19 positive cells and single cell culturing, we picked eight bright clones. PCR based genotyping showed that the marker was bi-allelically inserted at the targeted locus in clone #2 and #8 (FIG. 3B), and ddPCR based copy number analysis shows these clones have four copies of UbC promoter. Then, we subjected the clone #2 to 2nd round of editing using Cas9/gRNA and a donor vector as depicted in FIG. 3A. Following that, tCD19 negative cells were enriched by MACS separation, then single cell cloning gave us a desired line which has 2A-mOrange at just before stop codon of RUNX1 bi-allelically (clone #1, 3, 5, 6 and 7, FIG. 3C). In this way, we have created a PSC line in which we have introduced a reporter for RUNX1 without disrupting the endogenous RUNX1 gene. To confirm whether the integrated mOrange works as reporter for RUNX1, we subjected this iPS cell line to differentiation into hematopoietic stem progenitor cells (HSPCs) (Nishimura et al. Cell Stem Cell 12, 114-126 (2013)). After 13 days of co-culturing with irradiated C3H10T1/2 cells, we detected mOrange-positive HSPCs-like cells (FIG. 3D). FACS analysis shows that the population which is positive for CD34 and intermediately positive for CD45, which mostly contains HSPCs, express bright mOrange greater than the other population which contains undifferentiated or the other cell types (FIG. 3E). These results demonstrate that the mOrange reporter cells retain their differentiation capacity and accurately report on the expression of RUNX1, a non-cell surface transcriptional factor that regulates lineage differentiation. We also conducted further editing at GFI1 locus using this RUNX1-mOrange line to make RUNX1-GFI1 double reporter line by same editing strategy (FIG. 9).

Figure 4B:
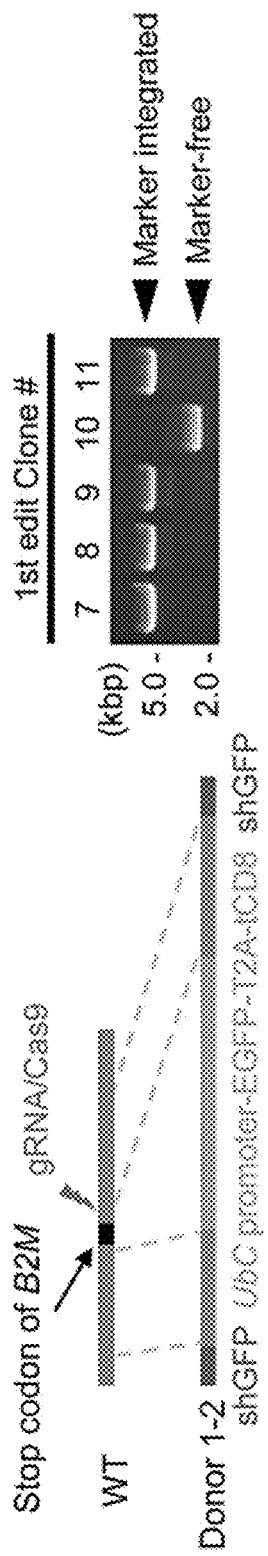
Figure 10A:
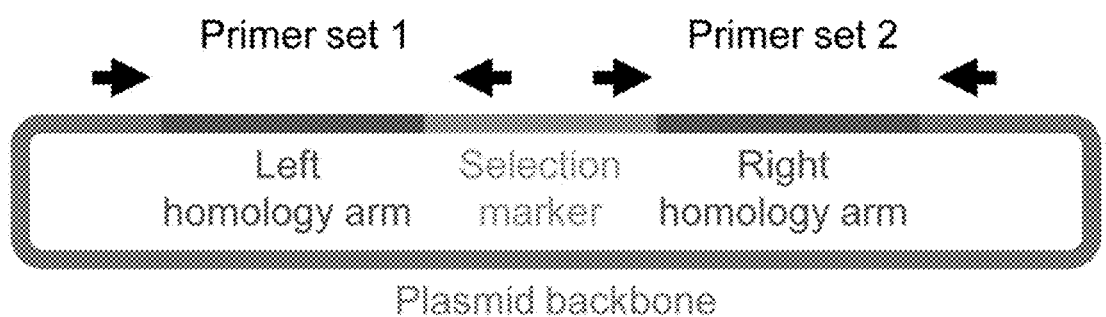
FIGS. 10A-10C show detection of random integration in RUNX1 and GFI1 editing after the 1st round of editing.
Figure 10B:
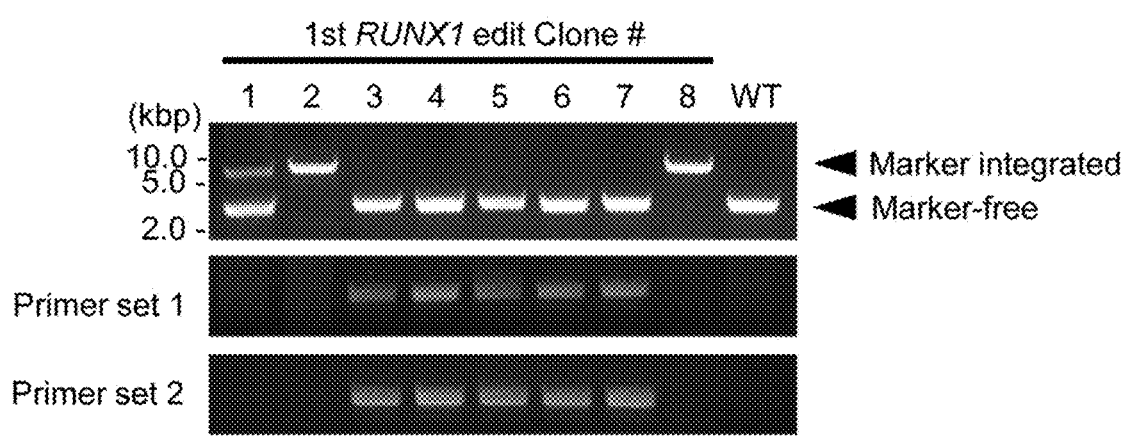
Figure 10C:
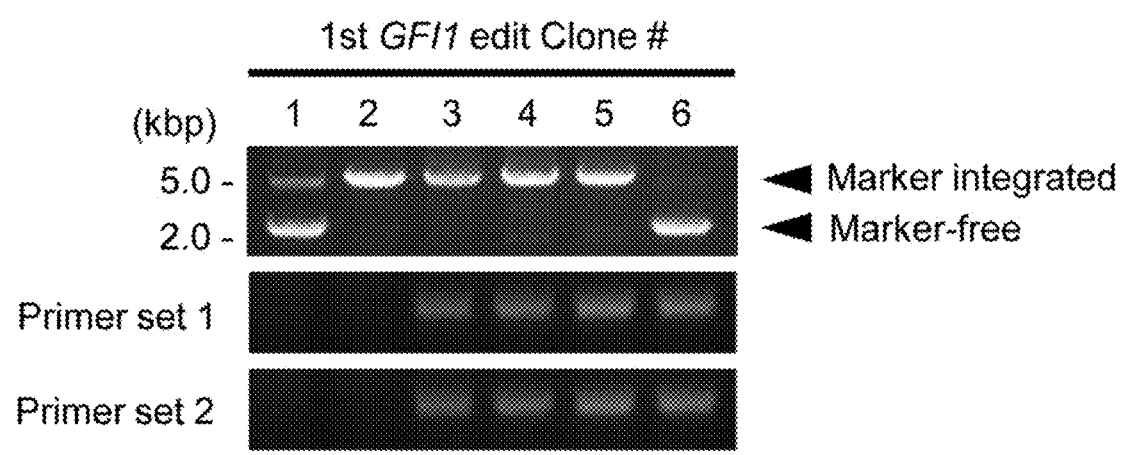
Figure 11A:
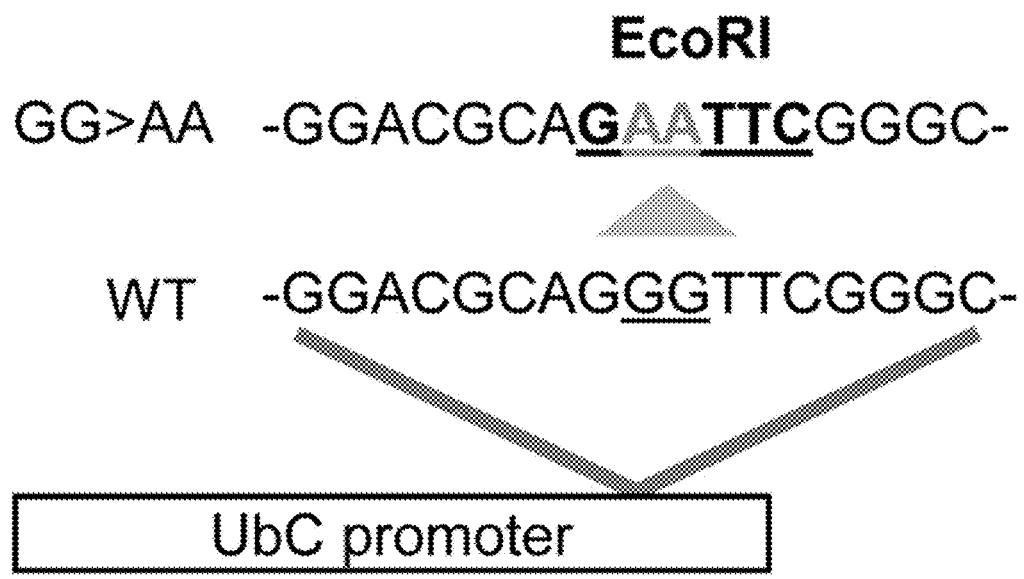
FIGS. 11A-11G show regular PCR based copy number analysis of UbC promoter in B2M editing.
Figure 11B:
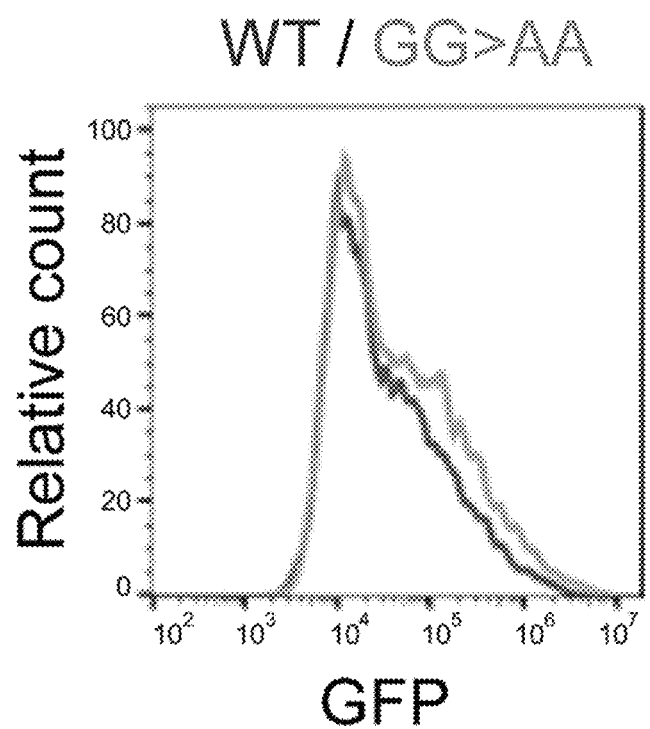
Figure 11C:
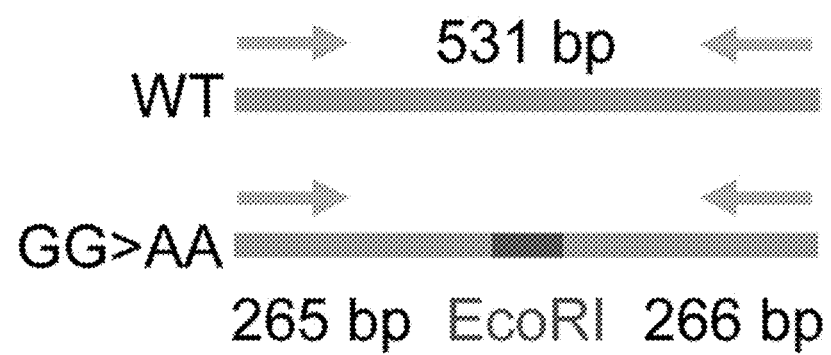
Figure 11D:
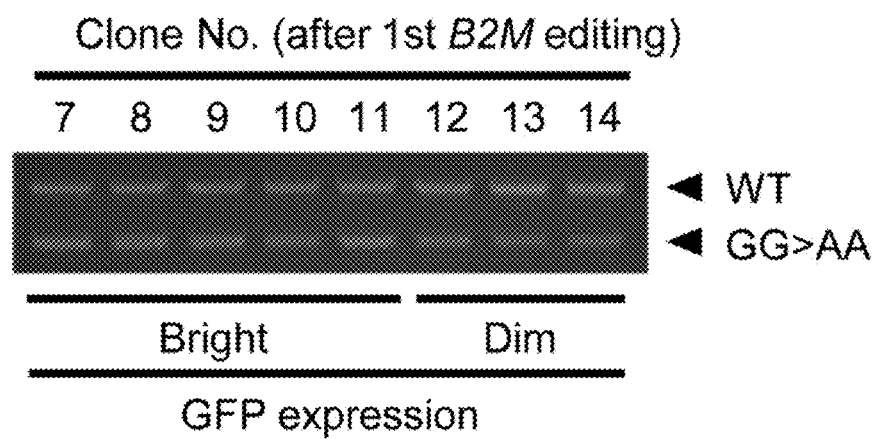
Figure 11E:
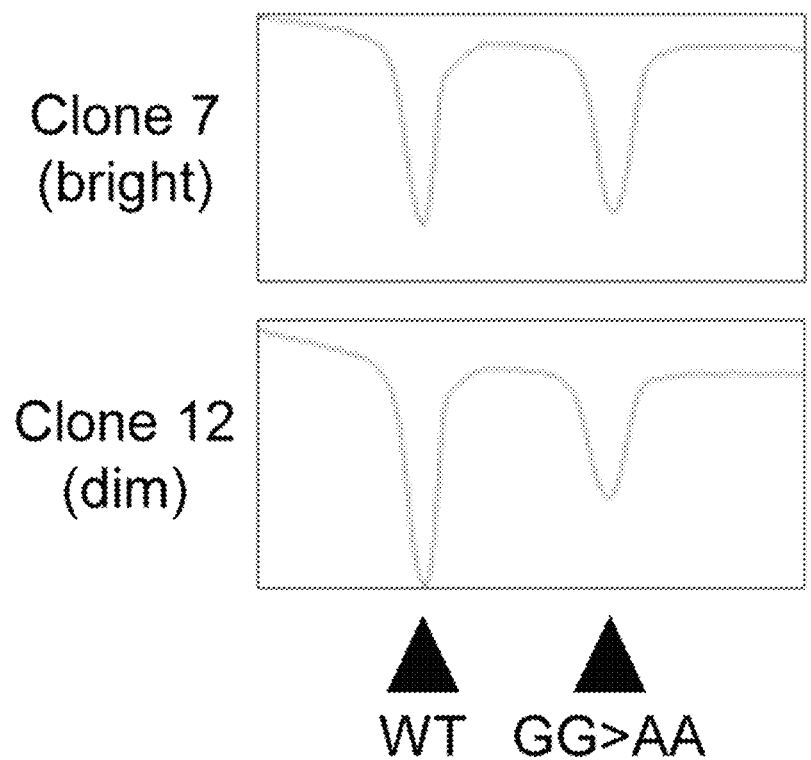
Figure 11F:
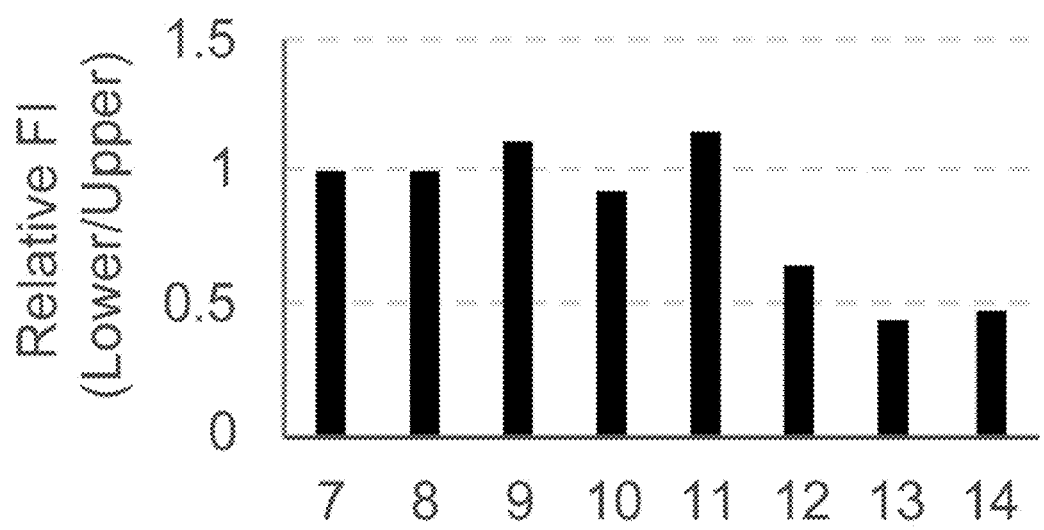
Figure 11G:
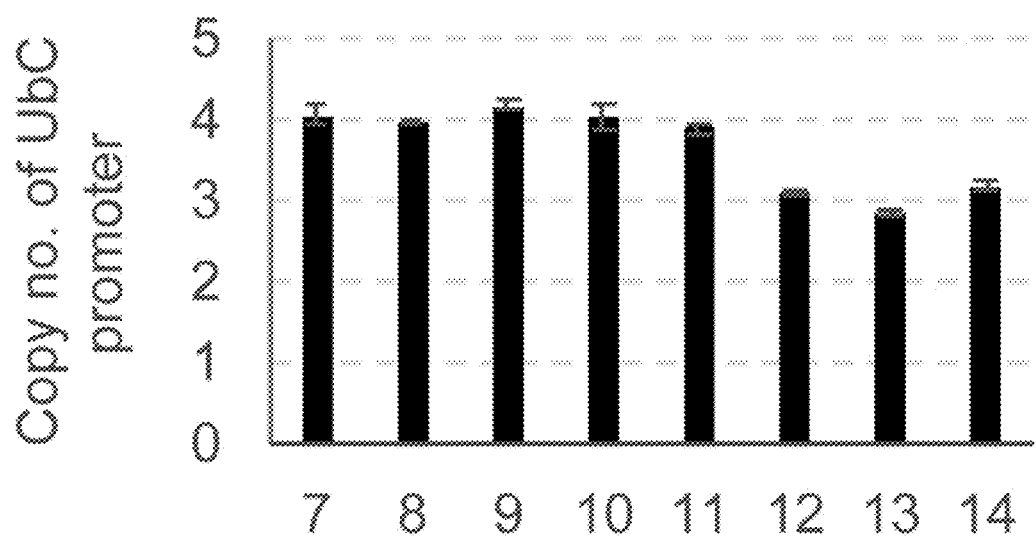

In both RUNX1 and GFI1 reporter integration, the bi-allelic targeting frequency without random integration at the 1st editing step occurred in less than 30% of the clones. Since most of the clones with random integration had plasmid backbone derived sequences (FIG. 10), we hypothesized that the introduction of negative selection feature in the plasmid backbone would effectively reduce enrichment of cells with random integration in 1st round editing. Instead of using the widely used thymidine kinase selection method which is limited by the need to use drug selection, we developed a novel negative selection method based on an shRNA-based counter selection. In this system the shRNA cassette flanks both homology arms and is designed to suppress the positive marker selection gene. As long as the shRNA is expressed (either from episomal expression or from random integration), the marker gene will be suppressed and the cell will not score as positive. Once episomal expression is lost, marker gene suppression is relieved and positive marker clones in which the cassette has been integrated only in a targeted fashion can easily be identified. We applied this system for the editing of the B2M locus in the ES H9 line with a donor vector designed to integrate an HLA-A*24 cDNA with linker at the 5' side of the B2M stop codon to create a B2M-HLA-A*24 fusion protein. As shown in FIG. 4B, shGFP expression cassettes (0.3 kb each) were introduced at outside of both left and right homology arm in 1st donor vector, and the selection markers were changed to GFP and tCD8 from mCherry and tCD19. As a result, we obtained 4 bi-allelically marker integrated clones without random integration from 5 bright clones (FIG. 4B), while only one bi-allelically targeted clone was obtained from 6 bright clones using donor vector without the shRNA selection system (FIG. 4A), showing that shRNA-based counter selection feature effectively reduced contamination of cells with random integration in positive selection from the $1^{st}$ round editing. We could identify such clones without having to use drug selection thus making the system easier and less toxic on the remaining clones.

In addition, we found that the introduction of a mutation (GG>AA) at 314th and 315th upstream from ATG, which produces a de novo EcoRI site, does not affect human UbC promoter activity. This feature enables us to perform copy number analysis of the new exogenous UbC promoter driving the selection marker by regular PCR without having to use quantitative PCR strategies such as ddPCR (FIG. 11). Then we confirmed that we obtained 8 correctly edited clones from 8 enriched clones by $2^{nd}$ round editing combined with negative selection (FIG. 4C), and desired HLA expression profile (knockout of endogenous HLAs and expression of HLA-A*24) was observed in edited cells (FIG. 4D). We also compared copy number variation (CNV) of genome among the original lines, $1^{st}$ and/or $2^{nd}$ round editing products in all editing experiments by high-density SNP array analysis. Although there was no substantial chromosomal change (deletion or multiplication) caused by the two-step editing process, we found "copy neutral loss of heterozygosity (LOH)" in one of the TBX1 lines after $2^{nd}$ round editing and one RUNX1 marker integrated line at each targeted locus, suggesting these changes were caused by a gRNA/Cas9 driven double strand break. Most lines after the 2-step editing process, however, did not have such changes. Given that these changes were induced by the gRNA/Cas9 break, such changes are likely to also occur using other editing strategies using engineered nucleases. G-band analysis, which is often performed for checking genomic integrity, cannot detect copy neutral LOH and thus may have been missed in prior studies that did not use dense SNP array analysis. CNV analysis using high-density SNP arrays around the on-target site is recommended especially in case of functional analysis or clinical cell therapy using genomically edited cells.

Figure 12:
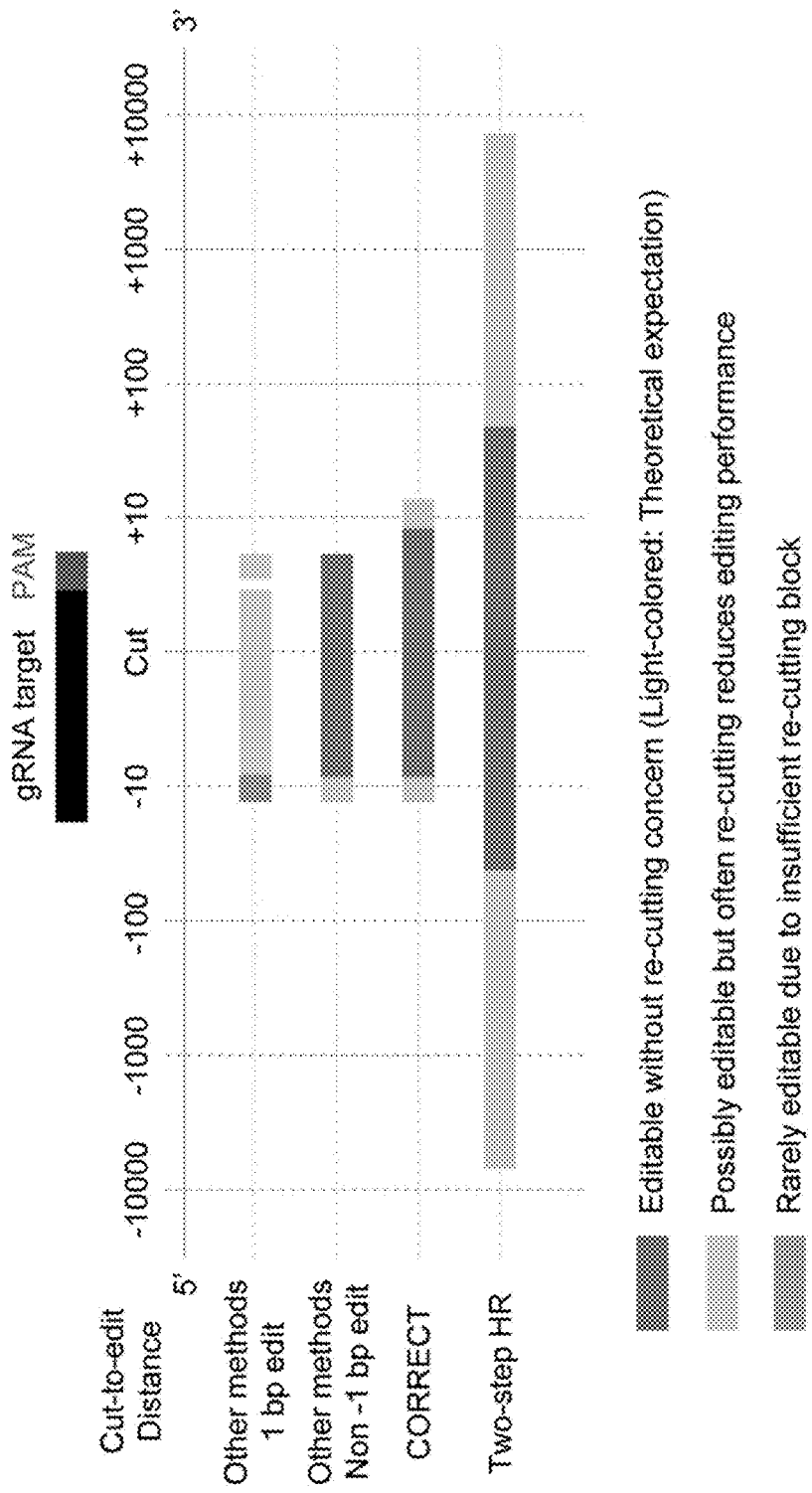
FIG. 12 shows editable range in scarless editing in terms of limitation of cut-to-edit distance (Paquet et al. 2016) and Cas9 tolerance of mismatch (Fu et al., 2013)
Figure 13A:
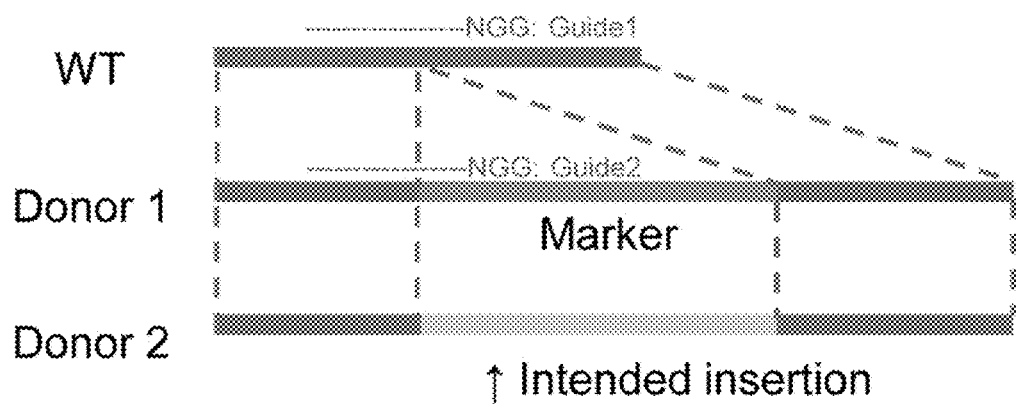
FIGS. 13A-13D show donor DNA design for various patterns of scarless editing. We demonstrated that HR-based editing is available to integrate and delete more than 3 kb in TBX1 editing, and modify about 3 kb to 1 kb sequence in B2M editing in hPSCs if it is combined with appropriate marker selection. Combining them will theoretically enable additional application of scarless edit as follows.
Figure 13B:
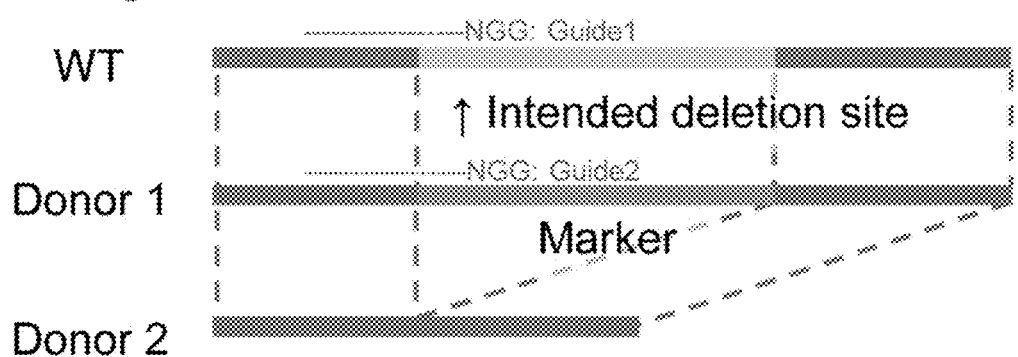
Figure 13C:
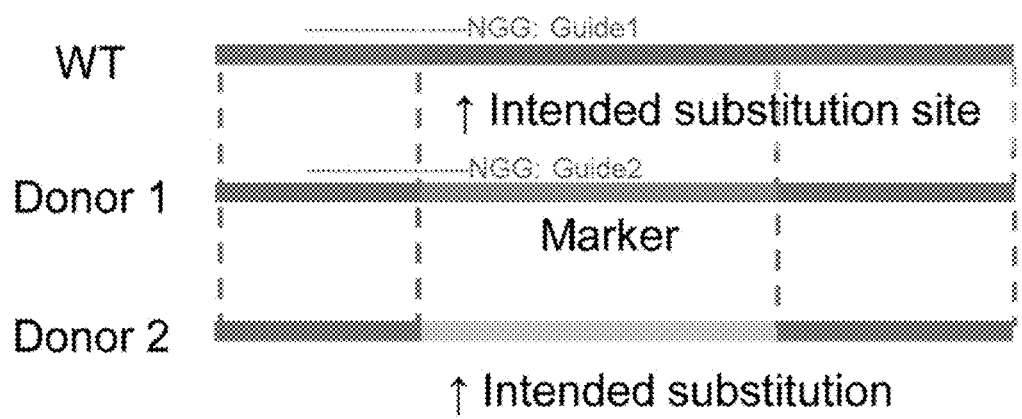
Figure 13D:
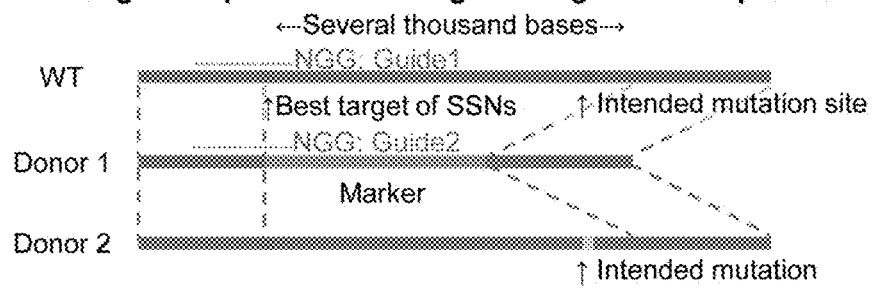
Figure 14:
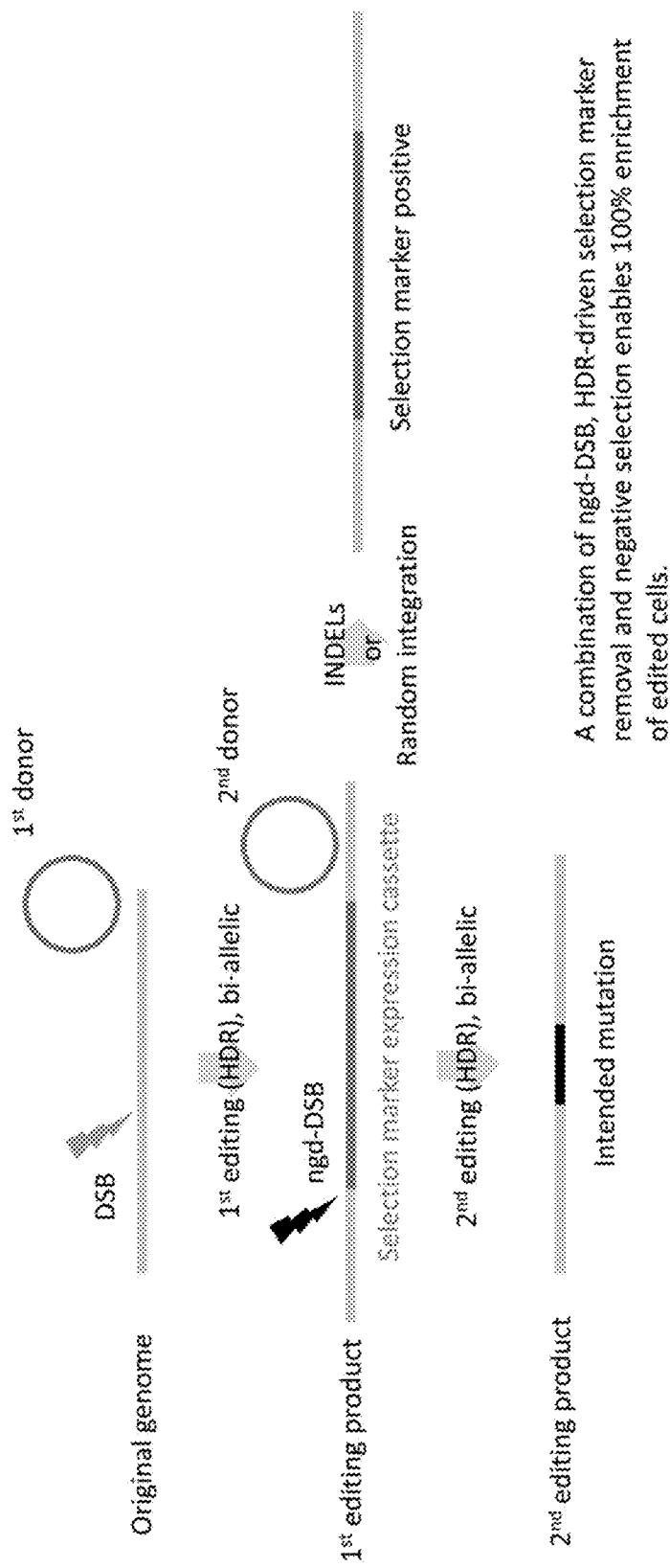
FIG. 14 shows a schematic of a two-step HDR based scarless genome editing strategy using a combination of ngd-DSB, HDR-driven selection marker removal, and negative selection. This method enables 100% enrichment of edited cells.
Figure 15:
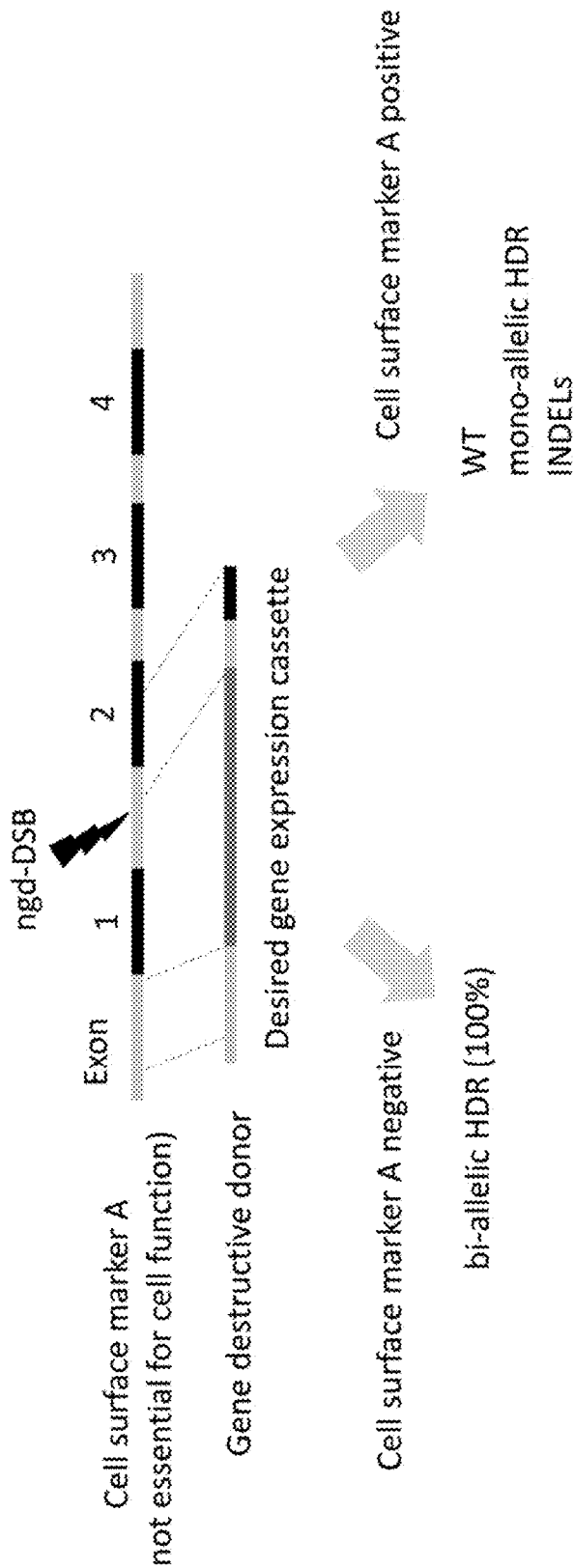
FIG. 15 shows application of a selection strategy using surface markers which are not essential for cell function.
Figure 16:
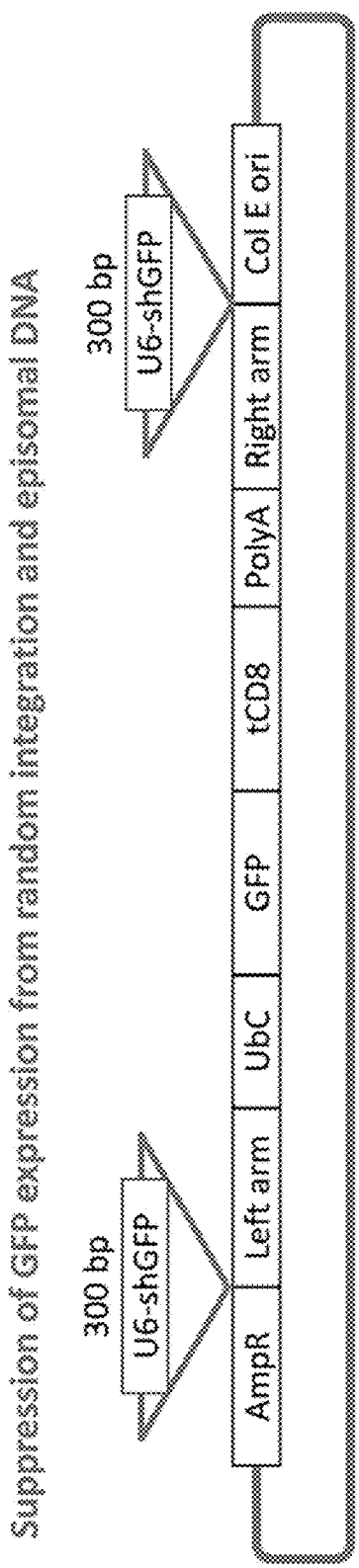
FIG. 16 shows donor plasmid design for suppression of GFP expression from randomly integrated or episomally existing selection markers.

These results demonstrate that the method can be used to introduce either single nucleotide changes or large DNA fragments in a precise and scarless manner. In contrast to other methods, our method gives us three kinds of important advances in scarless genome editing. First, our method produces well matched isogenic control (WT), homozygous, and heterozygous lines from the same clone (as shown in TBX1 editing). Because the editing processes requires long term culture which may change the phenotype of hPSCs, comparison of phenotypes between the original line and edited line can be misleading because of those acquired changes. Our strategy takes advantage of the extremely high targeting efficiency in the $2^{nd}$ editing step, such that it is easy to generate different genotypes (WT, heterozygotes, and homozygotes) in the same step from the same clone thus reducing the variability induced by prolonged culturing. Second, our method allows the introduction of a larger transgenes in a scarless manner, an insert size that is not possible to integrate using ssODN methods, including into genes that are not expressed in hPSCs. Other methods have achieved integrations of reporter genes, for example, but only into genes that are expressed in hPSCs. Our editing at RUNX1 and GFI1 are examples of scarless marker integration at genes that are not expressed in hPSCs. Third, our method worked efficiently at loci in which the cut to edit distance was long, a feature that had not been previously achieved using other methods. For the B2M locus, for example, we achieved 80% targeted integration of our marker at a cut-to-edit distance of 63 base pairs. This extension of the cut-to-edit distance significantly expands the range of scarless edits that can be achieved in hPSCs (FIG. 12). Using marker selection followed by marker removal increased the efficiency of both the $1^{st}$ and $2^{nd}$ editing steps thus creating a system in which only 5-10 clones needed to be analyzed instead of the several hundred that are needed using other methods (Table 2) (Paquet et al., supra; Miyaoka et al. Nat. Methods 11, 291-3 (2014)). We have additionally improved the efficiency of the $1^{st}$ step editing process by including an shRNA cassette against the fluorescent marker protein thereby reducing or even eliminating clones with random integrations from being picked. For the $2^{nd}$ round of editing, the targeting frequency in enriched, marker cells can be 100% and is always close to 100% thus eliminating the need for painstaking and laborious screening and analysis of hundreds of clones. This high frequency is achieved by using a fluorescent marker, which was also used with Cre-loxP-based 2 step editing previously (Xi et al. Genome Biol. 16, 1-17 (2015)), but enables our novel 2-step method to work with no failed examples to date. In addition, negative selection contributes to 100% targeting frequency at the 2nd editing step because it enriches only targeted cells at the first step unlike positive selection which identifies cells with both targeted integrations and random integrations. This streamlined process results in the identification of heterozygous and homozygous clones in 6-8 weeks and was achieved at a locus that is not expressed in human PSCs thus demonstrating it does not require the target site to be expressed in order to be fast and efficient. This high efficiency eliminates the need for labor intensive colony picking, genotyping, and sequencing that is required with alternative methods. In summary, our method addresses multiple bottlenecks in generating human pluripotent cells with scarless genome editing thus advancing stem cell technologies as disease and developmental models, drug screening tools, and therapeutics.

Materials and Methods

Plasmid sgRNA expression vectors were constructed by insertion of annealed oligonucleotide including target sequences and adapter sequence into BbsI digested px330 (Addgene plasmid #42230) containing a human codon-optimized SpCas9 expression cassette and a human U6 promoter driving the expression of the chimeric sgRNA. The target sites are described in FIG. 6.

Donor DNA plasmid vectors were constructed by NEBuilder HiFi DNA Assembly (NEB). Left and right homology arms were amplified by nested PCR using genomic DNA extract from K562 cells (ATCC) as a template. Mutation of TBX1 was generated by PCR and ligation.

Cell Culture

Human ES H9 cells were used for TBX1 and B2M editing, and the TkDA3-4 iPSC line established from human dermal fibroblasts (Cell Applications Inc.) as described previously (Takayama et al. J Exp Med. 207, 2817-2830 (2010)) was used for RUNX1 and GFI1 editing. iAM9 iPSC line was used for positive control of HLA-A*24 detection. hPSCs were maintained in mTeSR1 (STEMCELL technologies) on feeder free Matrigel (Corning)-coated plate. Subculture was performed every 4-6 days by EDTA method. After plating, 10 μM Y-27632 (Tocris) was added for 1 day.

K562 (ATCC) cells were maintained in RPMI 1640 (HyClone) supplemented with 10% bovine growth serum (HyClone), 100 mg/ml streptomycin, 100 units/ml penicillin, and 2 mM 1-glutamine.

Transfection

ESCs of iPSCs (70-80% confluent) were harvested with Accutase (Life Technologies). $2 \times 10^6$ cells were subjected to electroporation using P3 Primary Cell 4D-Nucleofector L kit and 4D-Nucleofector system (Lonza) according to manufacturer's protocol (Program: CB-150 for TBX1, RUNX1 editing, CA-137 for GFI1 and B2M editing) with 5 μg pX330 plasmid and 5 μg donor vector. In the transfection with mixture of donor DNAs (WT and TBX1 c.928G>A), 2.5 μg each were subjected. After transfection, cells were plated into 3 wells of Matrigel-coated 6 well plate and were maintained with 10 μM Y-27632 added mTeSR1 for 3 days. Then cells were maintained with mTeSR without Y-27632.

K562 cells were nucleofected using the Lonza Nucleofector 2b (program T-016) and a nucleofection buffer containing 100 mM $KH_2PO_4$, 15 mM $NaHCO_3$, 12 mM $MgCl_2 \times 6H_2O$, 8 mM ATP, 2 mM glucose (pH 7.4).

HSPCs Differentiation Using iPSCs

Differentiation using iPSC into HSPCs was performed as reported previously with slight modification. In brief, small clumps of iPSCs (<100 cells) were transferred onto irradiated C3H10T1/2 cells and co-cultured in EB medium (Iscove's modified Dulbecco's medium supplemented with 15% fetal bovine serum and a cocktail of 10 μg/ml human insulin, 5.5 μg/ml human transferrin, 5 ng/ml sodium selenite, 2 mM L-glutamine, 0.45 μM a-monothioglycerol, and 50 μg/ml ascorbic acid) in the presence of VEGF, SCF, TPO, IL-3 and IL-6. Media was changed every three days. After 14 days of cultivation, cells were harvested by treatment with TrypLE Select (Thermo Fisher Scientific) for 5 minutes at 37° C., then the cells were subjected to FACS analysis.

Flow Cytometry and Fluorescence Microscopy

For measuring of editing frequency, after harvested with Accutase, cells were stained with anti-human CD19 antibody conjugated with APC (clone LT19, 1:20, Miltenyi Biotec) according to manufacturer's protocol. Then the cells were washed twice with wash buffer (PBS with 1% human albumin and 0.5 mM EDTA). For detection of HLAs, after 3 days of 50 ng/mL INFγ treatment, cells were detached and stained with anti-HLA-A*02 conjugated with APC (clone BB7.2, 1:20, eBioscience), anti-HLA-A*03 conjugated with PE (clone GAP. A3, 1:20, eBioscience or anti-HLA-A*24 conjugated with FITC (clone 22E1, 1:20, MBL) according to manufacturer's protocol. Then the cells were washed twice with wash buffer. Data was acquired using Accuri C6 plus flow cytometer (BD biosciences). For differentiation study, after detached, propidium iodide was added to permit exclusion of dead cells. The cells were stained with anti-CD34 conjugated with APC-Cy7 (eBioscience) and anti-CD45 conjugated with APC (eBioscience) for 30 minutes at 4° C., then the cells were washed twice with wash buffer. Data was acquired using FACSAria II (BD Biosciences). All acquired data was analyzed using FlowJo (FlowJo, LLC).

To distinguish clones with bright and dim mCherry fluorescence before colony pickup, cells were observed using a fluorescent microscope IX-70 (Olympus). All fluorescence image was acquired using EVOS FL cell imaging system (Thermo Fisher Scientific).

Off-Target Analysis

Gene edited ES/iPS cell lines were tested for off-target editing events predicted for each sgRNA by COSMID46 tool (http://crispr.bme.gatech.edu), which considers mismatch, insertions and deletions in the guide RNA target sequence. Results are shown in Table 2. All sequence at loci predicted as off-target candidate were checked in final product, and no off-target editing was detected. No off-target candidate was predicted for guide RNA sequences used for TBX1 and B2M 1st round editing all 2nd round editing in default setting of COSMID46 tool.

Magnetic-Assisted Cell Separation (MACS)

Before 1 hour of separation, cells were treated with 10 µM Y-27632 and this treatment was kept during separation by adding Y-27632 into wash buffer (PBS with 1% human albumin and 0.5 µM EDTA). After cells were detached with Accutase, positive and negative selection were performed with MS and LD columns (Miltenyi Biotec) respectively and magnetic beads-conjugated anti-human CD19 (Miltenyi Biotec) or anti-human CD8 (Miltenyi Biotec) according to manufacturer's protocol at day 6 and 7 days after transfection respectively. Positive selection was repeated twice serially using two MS columns.

Genotyping and Sequence Analysis

Marker insertion into TBX1 locus was confirmed by PCR with Accuprime GC rich DNA Polymerase (Thermo Fisher Scientific). Sequence analysis were performed McLab (South San Francisco, Calif., USA) using PCR amplicon produced by PrimeSTAR HS with GC rich (Takara Bio). Genotyping of RUNX1, GFI1 and B2M were performed with PrimeSTAR GXL (Takara Bio). All primers are listed in Table 1. Genomic DNA sample was prepared by QuickExtract DNA Extraction Solution (Epicentre Madison) following manufacturer's instructions.

ddPCR Based Copy Number Analysis

Copy number analysis of integrated exogenous UbC promoter derived from selection marker was performed by Droplet Digital PCR (ddPCR) which quantifies the genomic UbC promoter and reference sequence. Copy number of UbC promoter reflects the total from endogenous two copies and exogenous donor DNA derived copies, on the other hand, there are only two copies of reference sequence. Therefore, comparison between amount of UbC promoter and reference sequence provide net copy number of marker allele. ddPCR was performed using QX200 (BioRad) and ddPCR Supermix for Probe (BioRad) according to manufacturer's protocol. Sequence of primers and probes were primer1 (CGT CAG TTT CTT TGG TCG GT, SEQ ID NO:1), primer2 (AAA CAC ACT CGC CAA CCC, SEQ ID NO:2), probe (TCT TCT TAA GTA GCT GAA GCT CCG GT, SEQ ID NO:3) for UbC promoter, primer1 (CTC TCC TCT TTG ATA CGG CCC, SEQ ID NO:4), primer2 (AGT GTT GTC CCA GAC AGT GC, SEQ ID NO:5), probe (CTG CCA AGT TGT GGC CTC TGT CAA AG, SEQ ID NO:6) for reference loci. Genomic DNA samples were prepared by QuickExtract DNA Extraction Solution.

Alternative Copy Number Analysis of UbC Promoter by Regular PCR and Restriction Enzyme Digestion PCR reaction was performed with genomic DNA samples and primers (Fwd: TGC GGG AAA GCT CTT ATT CGG (SEQ ID NO:18), Rev: CAA AAA CGG CCA GAA TTT AGC G (SEQ ID NO:19) using Phusion Green Hot Start II High-Fidelity PCR Master Mix (Thermo Fisher Scientific) in 15 µL scale. Then 1 µL of EcoRI-HF (NEB) diluted into 10 U/µL with 1× CutSmart Buffer was added directly into PCR product. After 1.5 hour of incubation at 37° C., samples were subjected to electrophoresis (30 minutes, 150V) on a 2.0% agarose gel containing Midori Green Advance (Fast Gene). Image was captured using ChemiDoc XRS+ (Bio-Rad), then analyzed using Image J software.

Immunocytochemistry and Microscopy

For staining of NANOG and OCT4, cells were fixed in 4% paraformaldehyde, permeabilized in 0.2% Triton X-100 in PBS, blocked with blocking buffer (0.1% Triton-X and 2% FBS in PBS) and stained with antibodies diluted 200-fold with blocking buffer at room temperature overnight, then the cells were stained with anti-rabbit IgG antibody conjugated with Alexa594 (R37117, Thermo Fisher Scientific) diluted 2000-fold with blocking buffer at room temperature for 40 minutes. For staining of TRA-1-60, cells were fixed in 4% paraformaldehyde, blocked with 2% FBS in PBS and stained with antibodies diluted 200-fold by 2% FBS in PBS. Antibodies used in this study were obtained from STEMGENT, and their catalog numbers are NANOG (cat #09-0020), OCT4 (cat #09-0023) and TRA-1-60 (cat #09-0068). The fluorescence images were acquired using EVOS FL cell imaging system.

High-Density SNP Array Analysis

To check the genome integrity during editing process high-density SNP array analysis was performed using CytoSNP-850K BeadChip (Illumina). 200 ng of genomic DNA samples prepared by GeneJET genomic DNA purification kit (Thermo Fisher Scientific) were processed, hybridized to the microarray slides according to manufacturer's protocol. Then, they were scanned using the iScan system (Illumina). Obtained data was analyzed by GenomeStudio software with cnvPartition algorithm (Illumina).

While the preferred embodiments of the invention have been illustrated and described, it will be appreciated that various changes can be made therein without departing from the spirit and scope of the invention.

TABLE 1

Primer list for genotyping and sequencing

Figure 3B:
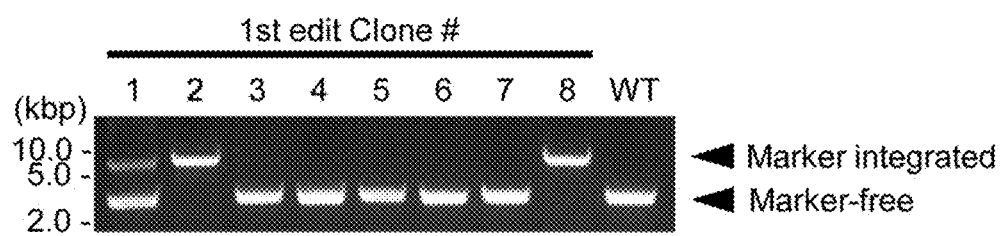
Figure 3C:
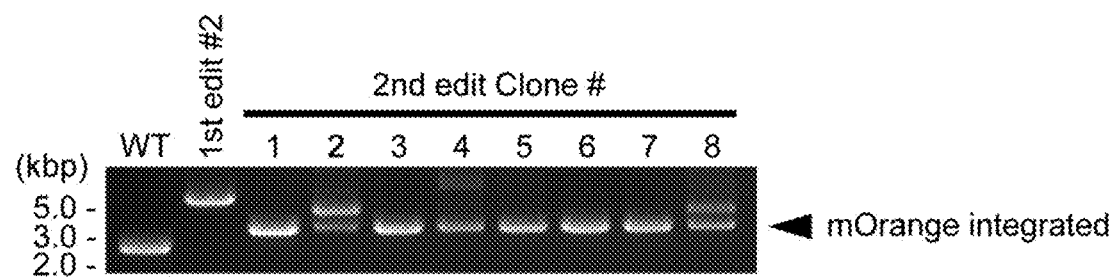
Figure 3D:
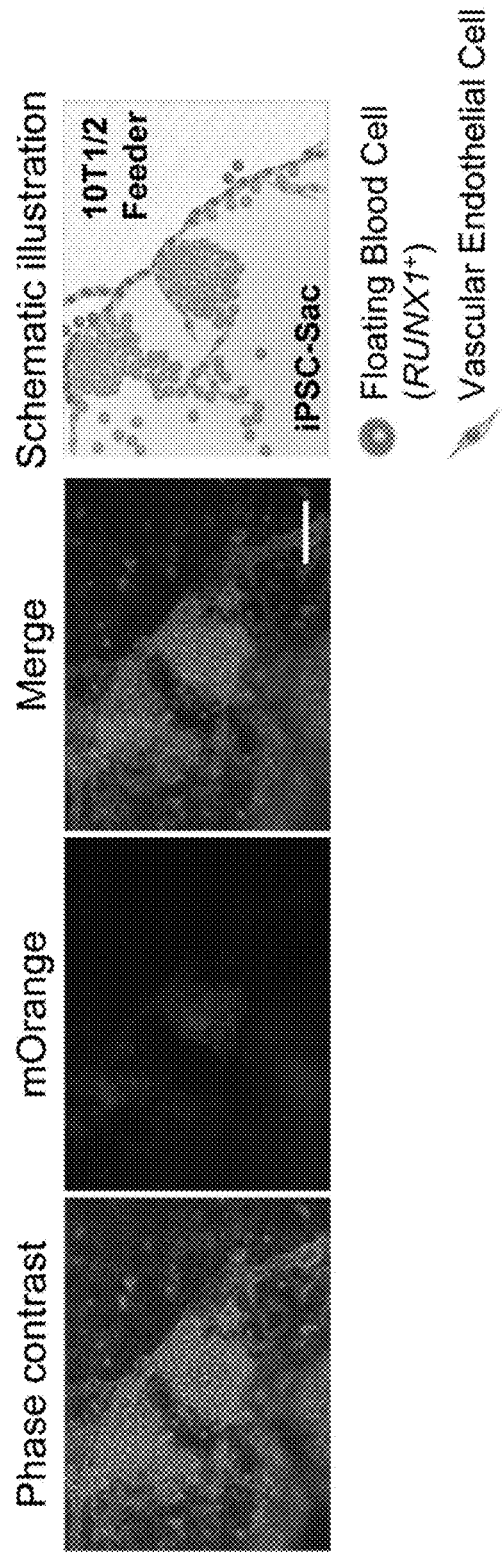
Figure 3E:
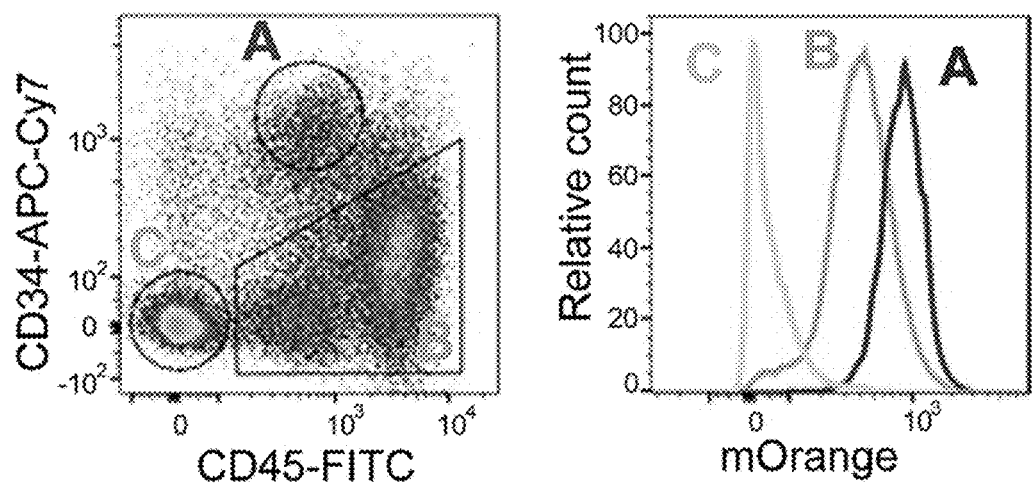
Figure 4C:
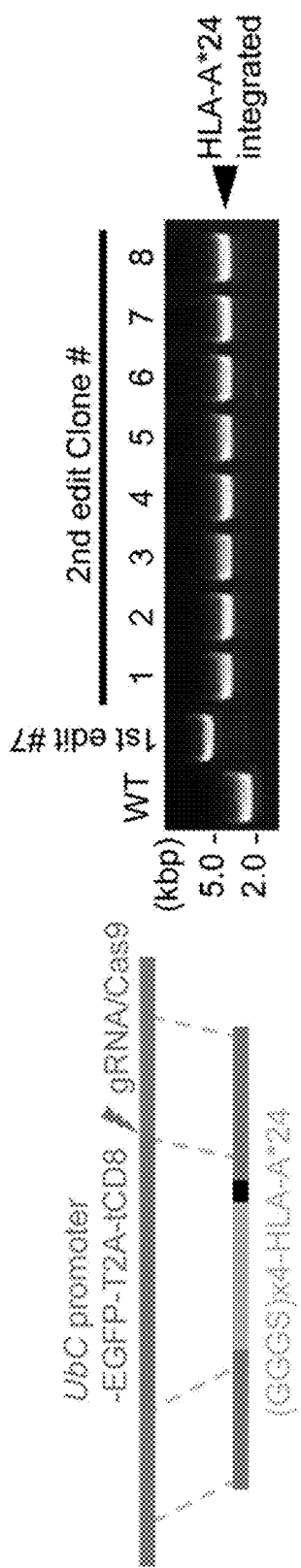
Figure 4D:
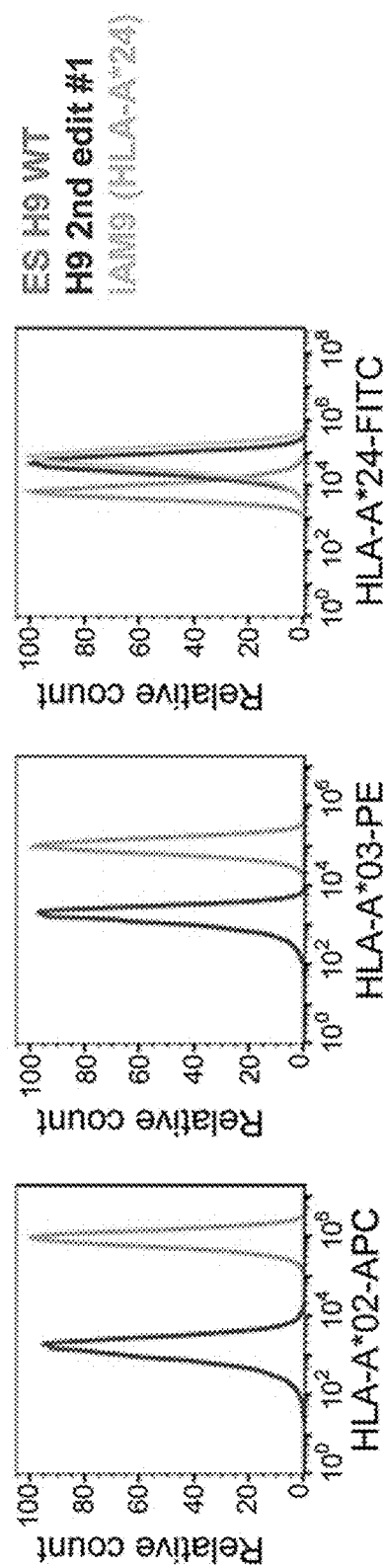
Figure 5A:
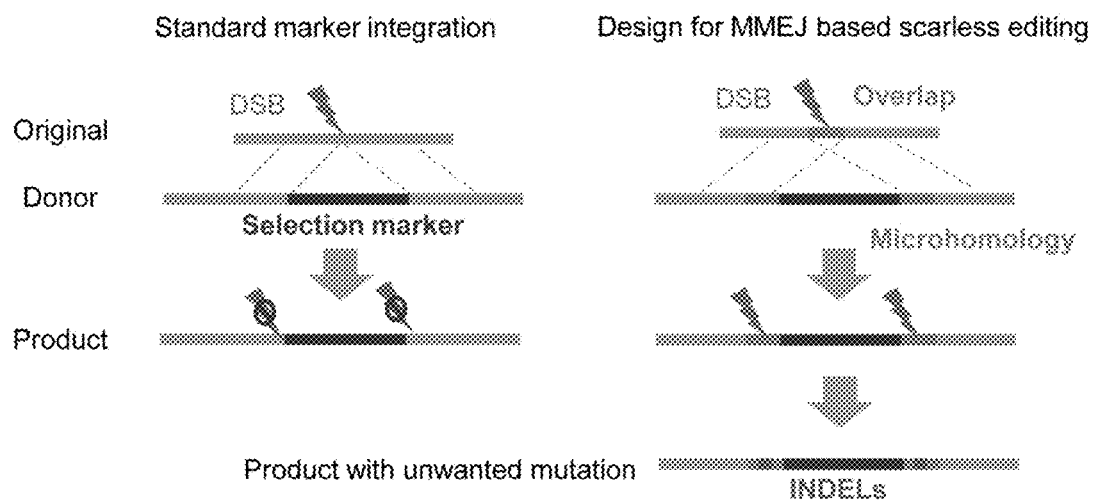
Figure 6B:
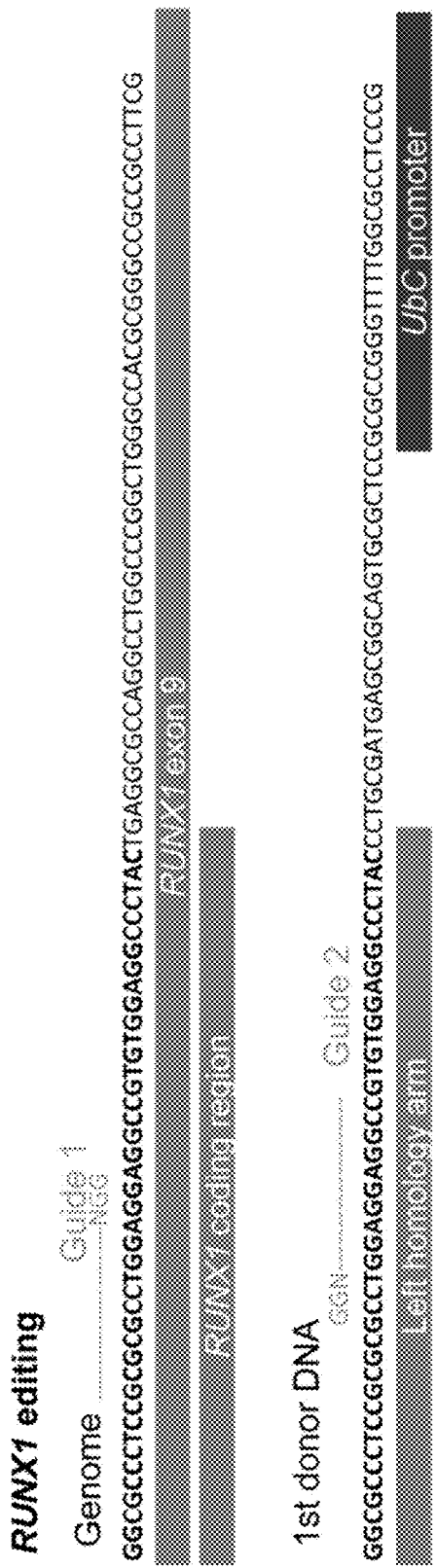

| Target/Purpose | | Sequence | FIG. |
|---|---|---|---|
| Detection of marker-integrated TBX1 | Forward | GAGGATTGGGAAGACAATAGCAGG (SEQ ID NO: 11) | FIG. 2D |
| | Reverse | GCCTCCGACCGGGCGCTTTG (SEQ ID NO: 12) | |
| Detection and sequencing of marker-free TBX1 | Forward | GGCCCAGTGACCCAGCCTCATCT (SEQ ID NO: 13) | FIGS. 2D, 2G, 2H |
| | Reverse | GCCTCCGACCGGGCGCTTTG (SEQ ID NO: 14) | FIGS. 6A, 6B |
| | Read | GCTGCAGGGCTCCAGCGGCTT (SEQ ID NO: 15) | |
| Detection of RUNX1 | Forward | GGGTGGCAGATTCTGGGTAG (SEQ ID NO: 16) | FIGS. 3B, 3F |
| | Reverse | CAGCCTGGTGAAAGCAACAC (SEQ ID NO: 17) | |
| Detection of GFI1 | Forward | AATGCCATGCTGGGCTATTG (SEQ ID NO: 24) | FIGS. 8B, 8C |
| | Reverse | CCAGCTTTCCCCCTACAGAC (SEQ ID NO: 25) | |
| Detection of B2M | Forward | ATGCAGCGCAATCTCCAGTGA (SEQ ID NO: 26) | FIGS. 4A, 4B, 4C |
| | Reverse | GTAGCTGCAGACAGTTCTCCAA (SEQ ID NO: 27) | |
| Detection of random integration 1 | Forward | AAGGATCAGGACGCTCGCTG (SEQ ID NO: 28) | FIG. 9 |
| | Reverse | GTCTCATGAGCGGATACATATTTGAATG (SEQ ID NO: 29) | |
| Detection of random integration 2 | Forward | CACCTCTGACTTGAGCGTCG (SEQ ID NO: 30) | FIG. 9 |
| | Reverse | GGAAATTGCATCGCATTGTCTGAGTAG (SEQ ID NO: 31) | |

TABLE 2

Off-target candidates predicted by COSMID tool.

| gRNA Sequence | Type | Mismatch | Chromosome | Location | Strand | Score |
|---|---|---|---|---|---|---|
| RUNX1 CCGTATGGAGTCCCTACTGAGG (SEQ ID NO: 20) | No indel | 2 | 13 | 109432648-109432669 | − | 1.01 |
| GFI1 A-GGGCTCAAATGAGGACCCAGG (SEQ ID NO: 21) | Del 19 | 1 | 20 | 42740270-42740291 | − | 2.94 |
| GFI1 ATGGGTTCAAATGAGCAACCTGG (SEQ ID NO: 22) | No indel | 2 | 17 | 1.6989632-16989654 | + | 4.21 |
| GFI1 ATGGGCTCAAATGAGC-CTCTGG (SEQ ID NO: 23) | Del 4 | 1 | 4 | 147500488-147500509 | − | 8.51 |

Mismatches and INDELs are underlined.

---

What is claimed is:

1. A method for scarless editing of genomic DNA of a cell, the method comprising:
   a) performing a first Cas9-mediated homology directed repair (HDR) step comprising:
      i) introducing a first donor polynucleotide into the cell, wherein the first donor polynucleotide comprises a first left homology arm and a first right homology arm for targeting the first donor polynucleotide to a target sequence in the genomic DNA of the cell, wherein the first left and right homology arms flank a sequence comprising an expression cassette encoding at least one selection marker and optionally an intended edit to the target sequence in the genomic DNA; and
      ii) introducing a first guide RNA (gRNA) and Cas9 into the cell, wherein the first guide RNA comprises a sequence complementary to the target sequence to be modified in the genomic DNA of the cell, such that the Cas9 forms a first complex with the first guide RNA, said guide RNA directing the first complex to the target sequence, wherein the Cas9 creates a double-stranded break (DSB) at the target sequence in the genomic DNA of the cell, wherein the sequence flanked by the first left and right homology arms in the first donor polynucleotide is integrated into the genomic DNA at the target sequence by Cas9-mediated HDR to produce a genetically modified cell;
   b) isolating the genetically modified cell based on positive selection for the at least one selection marker;
   c) performing a second Cas9-mediated homology directed repair (HDR) step comprising:
      i) introducing a second donor polynucleotide into the genetically modified cell of step (b), wherein the second donor polynucleotide comprises a second left homology arm and a second right homology arm for targeting the second donor polynucleotide to a target sequence in the genomic DNA of the genetically modified cell, wherein the second left and right homology arms flank a sequence which does not comprise the expression cassette encoding the at least one selection marker, and further comprises the intended edit when the sequence flanked by the first left and right homology arms in the first donor polynucleotide in step (a) does not comprise the intended edit;
      ii) introducing a second guide RNA (gRNA) and Cas9 nuclease into the genetically modified cell of step (b), wherein the Cas9 forms a second complex with the second guide RNA, said second guide RNA directing the second complex to the target sequence in the genomic DNA of the genetically modified cell, wherein the Cas9 creates a double-stranded break (DSB) at the target sequence in the genomic DNA, and the sequence flanked by the second left and right homology arms in the second donor polynucleotide is integrated into the genomic DNA at the target sequence by Cas9-mediated HDR, thereby replacing the expression cassette encoding the at least one selection marker from the genomic DNA by Cas9-mediated HDR to produce a genetically modified cell; and
   d) isolating the genetically modified cell comprising the intended edit based on negative selection for the at least one selection marker, wherein the expression cassette encoding the at least one selection marker is deleted.

2. The method of claim 1, wherein the sequence flanked by the first left and right homology arms in the first donor polynucleotide comprises an expression cassette encoding at least one selection marker and an intended edit to the target sequence in the genomic DNA, and the sequence flanked by the second left and right homology arms in the second donor polynucleotide does not comprise the intended edit.

3. The method of claim 1, wherein the intended edit introduces an insertion, deletion, or substitution into a gene in the genomic DNA of the cell.

4. The method of claim 1, wherein the positive selection comprises measuring florescence intensity of the at least one selection marker to determine if the genetically modified cell comprises a mono-allelic edit or a bi-allelic edit.

5. The method of claim 1, wherein the cell is from a eukaryotic, prokaryotic, or archaeon organism.

6. The method of claim 5, wherein the cell is a mammalian cell.

7. The method of claim 6, wherein the cell is a human cell.

8. The method of claim 1, wherein the cell is selected from the group consisting of a cell from a cell line, an immortalized cell, a cancerous cell, an embryonic stem cell, and an induced pluripotent stem cell.

9. The method according to claim 1, wherein the cell is in vitro or in vivo.

10. The method of claim 1, wherein said at least one selection marker is selected from the group consisting of a fluorescent marker, a cell surface marker, a drug resistance gene, a reporter gene, and a suicide gene.

11. The method of claim 1, wherein one or more of the first donor polynucleotide, the second donor polynucleotide, the first guide RNA, the second guide RNA, or the Cas9 are provided by a vector.

12. The method of claim 1, wherein the vector is a plasmid or viral vector.

13. The method of claim 11, wherein the first donor polynucleotide, the first guide RNA, and the Cas9 are provided by a single vector or multiple vectors.

14. The method of claim 11, wherein the second donor polynucleotide, the second guide RNA, and the Cas9 are provided by a single vector or multiple vectors.

15. The method of claim 1, wherein the first donor polynucleotide further comprises at least one expression cassette encoding a short hairpin RNA (shRNA) that targets the expression cassette encoding the at least one selection marker.

16. The method of claim 15, wherein the first donor polynucleotide comprises a pair of expression cassettes encoding the shRNA, wherein the first expression cassette of the pair is located 5' to the first left homology arm and the second expression cassette of the pair is located 3' to the first right homology arm.

17. The method of claim 15, wherein the shRNA reduces selection of clones expressing the selection marker that are randomly integrated into the genome.

18. The method of claim 1, wherein the double-stranded break does not affect the expression of said at least one selection marker.

19. The method of claim 2, wherein the intended edit is positioned within or near the expression cassette encoding the at least one selection marker.

20. The method of claim 1, wherein the sequence flanked by the first left and right homology arms in the first donor polynucleotide comprises an expression cassette encoding at least one selection marker and does not comprise an intended edit to the target sequence in the genomic DNA, and the sequence flanked by the second left and right homology arms in the second donor polynucleotide comprises the intended edit.

21. The method of claim 20, wherein the intended edit is a reporter gene for replacing the at least one selection marker in the genomic DNA of the genetically modified cell.

22. The method of claim 1, wherein the negative selection comprises measuring fluorescence intensity of the at least one selection marker to determine if the expression cassette encoding the at least one selection marker is deleted.

* * * * *